US012600801B2

(12) United States Patent
Price et al.

(10) Patent No.: US 12,600,801 B2
(45) Date of Patent: Apr. 14, 2026

(54) SINGLE-DOMAIN ANTIBODIES THAT BIND ROR1

(71) Applicant: Fred Hutchinson Cancer Center, Seattle, WA (US)

(72) Inventors: Jason Price, Seattle, WA (US); Colin E. Correnti, Seattle, WA (US); James M. Olson, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 413 days.

(21) Appl. No.: 18/350,617

(22) Filed: Jul. 11, 2023

(65) Prior Publication Data

US 2024/0092941 A1     Mar. 21, 2024

Related U.S. Application Data

(60) Provisional application No. 63/388,157, filed on Jul. 11, 2022.

(51) Int. Cl.
C07K 16/46 (2006.01)
C07K 16/30 (2006.01)

(52) U.S. Cl.
CPC ............ C07K 16/468 (2013.01); C07K 16/30 (2013.01); *C07K 2317/31* (2013.01); *C07K 2317/52* (2013.01); *C07K 2317/565* (2013.01); *C07K 2317/569* (2013.01)

(58) Field of Classification Search
CPC .. C07K 16/468; C07K 16/30; C07K 2317/31; C07K 2317/52; C07K 2317/565; C07K 2317/569; C07K 2317/77; C07K 16/2809; C07K 16/2803; C07K 2317/22; C07K 2317/24; C07K 2317/73
See application file for complete search history.

(56) References Cited

U.S. PATENT DOCUMENTS

| | | | |
|---|---|---|---|
| 5,929,212 A | 7/1999 | Jolliffe |
| 6,194,551 B1 | 2/2001 | Idusogie |
| 7,521,541 B2 | 4/2009 | Eigenbrot |
| 8,785,604 B2 | 7/2014 | Mary |
| 9,938,347 B2 | 4/2018 | Wang |
| 9,951,134 B2 | 4/2018 | Keyt |
| 10,400,038 B2 | 9/2019 | Keyt |
| 2002/0164328 A1 | 11/2002 | Shinkawa |
| 2003/0115614 A1 | 6/2003 | Kanda |
| 2003/0157108 A1 | 8/2003 | Presta |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2018/0118814 A1 | 5/2018 | Carroll |
| 2018/0118816 A1 | 5/2018 | Keyt |
| 2018/0265596 A1 | 9/2018 | Keyt |

| | | | |
|---|---|---|---|
| 2019/0100597 A1 | 4/2019 | Keyt |
| 2019/0185570 A1 | 6/2019 | Keyt |
| 2022/0033481 A1 | 2/2022 | Zhang et al. |
| 2022/0160766 A1 | 5/2022 | Ren et al. |
| 2024/0025996 A1 | 1/2024 | Price et al. |

FOREIGN PATENT DOCUMENTS

| | | |
|---|---|---|
| WO | WO1999051642 A1 | 10/1999 |
| WO | WO200061739 A1 | 10/2000 |
| WO | WO200129246 A1 | 4/2001 |
| WO | WO2002031140 A1 | 4/2002 |
| WO | WO2002051871 A2 | 7/2002 |
| WO | WO2003084570 A1 | 10/2003 |
| WO | WO2003085107 A1 | 10/2003 |
| WO | WO2003085119 A1 | 10/2003 |
| WO | WO2005035586 A1 | 4/2005 |
| WO | WO2005035778 A1 | 4/2005 |
| WO | WO2005053742 A1 | 6/2005 |
| WO | WO2008077546 A1 | 7/2008 |
| WO | WO2017127664 A1 | 7/2017 |
| WO | WO2018014001 A1 | 1/2018 |
| WO | WO2018017761 A1 | 1/2018 |
| WO | WO2018017763 A1 | 1/2018 |
| WO | WO2018017888 A1 | 1/2018 |
| WO | WO2018017889 A1 | 1/2018 |
| WO | WO2019165340 A1 | 8/2019 |

(Continued)

OTHER PUBLICATIONS

Adams, et al., "Extending the half-life of a fab fragment through generation of a humanized anti-human serum albumin Fv domain: An investigation into the correlation between affinity and serum half-life," MAbs., vol. 8, No. 7, 2016, pp. 1336-1346.
Bejcek, et al., "Development and characterization of three recombinant single chain antibody fragments (scFvs) directed against the CD19 antigen," Cancer Res., vol. 55, No. 11, 1995, pp. 2346-2351.
Braathen, et al., "The carboxyl-terminal domains of IgA and IgM direct isotype-specific polymerization and interaction with the polymeric immunoglobulin receptor," J. Biol. Chem., vol. 277, No. 45, 2002, pp. 42755-42762.

(Continued)

*Primary Examiner* — Julie Wu
*Assistant Examiner* — Sydney Van Druff
(74) *Attorney, Agent, or Firm* — C. Rachal Winger; Lee & Hayes PC

(57) ABSTRACT

Single-domain antibodies that bind receptor tyrosine kinase (ROR1) are described. The single-domain antibodies can be used for multiple purposes including in research, imaging, diagnosis, and treatment of ROR1-related conditions. The disclosed single-domain antibodies can be used as anti-cancer therapeutics such as antibody-drug conjugates, multi-domain binding molecules, or recombinant receptors or can be used as cancer imaging/diagnostic agents.

20 Claims, 21 Drawing Sheets

Specification includes a Sequence Listing.

(56)                References Cited

FOREIGN PATENT DOCUMENTS

WO        WO-2020198531 A2  *  10/2020   ............. A61K 40/11

OTHER PUBLICATIONS

Chen, et al., "Fusion protein linkers: property, design and functionality," Adv. Drug. Deliv. Rev., vol. 65, No. 10, 2013, pp. 1357-1369.
Doronina, et al., "Enhanced activity of monomethylauristatin F through monoclonal antibody delivery: effects of linker technology on efficacy and toxicity," Bioconjug Chem., vol. 17, No. 1, 2006, pp. 114-124.
Idusogie, et al., "Mapping of the C1q binding site on rituxan, a chimeric antibody with a human IgG1 Fc," J. Immunol., vol. 164, No. 8, 2000, pp. 4178-4178-4184.
Kanda, et al., "Comparison of cell lines for stable production of fucose-negative antibodies with enhanced ADCC," Biotechnol Bioeng., vol. 94, No. 4, 2006, pp. 680-688.
Mester, et, al., "Extended plasma half-life of albumin-binding domain fused human IgA upon pH-dependent albumin engagement of human FcRn in vitro and in vivo," MAbs., vol. 13, No. 1, 2021, 14 pages.
Okazaki, et al., "Fucose depletion from human IgG1 oligosaccharide enhances binding enthalpy and association rate between IgG1 and FcgammaRIIIa," J. Mol. Biol., vol. 336, No. 5, 2004, pp. 1239-1249.
Pezutto, et al., "CD19 monoclonal antibody HD37 inhibits anti-immunoglobulin-induced B cell activation and proliferation," J. Immunol., vol. 138, No. 9, 1987, pp. 2793-2799.
Ripka, et al., "Two Chinese hamster ovary glycosylation mutants affected in the conversion of GDP-mannose to GDP-fucose," Arch. Biocjhem. Biophys., vol. 249, No. 2, 1986, pp. 533-545.
Roovers, et al., "Efficient inhibition of EGFR signaling and of tumour growth by antagonistic anti-EFGR Nanobodies," Cancer Immunol Immunotehr., vol. 56, No. 3, 2007, pp. 303-317.
Saunders, et al., "Conceptual Approaches to Modulating Antibody Effector Functions and Circulation Half-Life," Front. Immunol., vol. 10, 2019, 20 pages.
Shen, et al., "A robust and versatile nanobody platform for drug delivery," bioRxiv, 2020, 41 pages.
Smith, et al., "Mouse model recapitulating human Fc? receptor structural and functional diversity," PNAS USA., vol. 109, No. 16, 2012, pp. 6181-6186.
Tijink, et al., "Improved tumor targeting of anti-epidermal growth factor receptor Nanobodies through albumin binding: taking advantage of modular Nanobody technology," Mol. Cancer. Ther., vol. 7, No. 8, 2008, pp. 2288-2297.
Yamane-Ohnuki, et al., "Establishment of FUT8 knockout Chinese hamster ovary cells: An ideal host cell line for producing completely defucosylated antibodies with enhanced antibody-dependent cellular cytotoxicity," Biotech. Bioeng., vol. 87, No. 5, 2004, pp. 614-622.
Search Report and Written Opinion for International Application No. PCT/US24/10077, Dated Jul. 9, 2024, 19 pages.

* cited by examiner

VHH-Fc Fusion

VHH

FIG. 1C

ROR1 / Nb11

ROR1 / Nb14

Ig — Ig-like domain
FZD — Frizzled domain
KRD — Kringle domain

TKD — Tyrosine kinase domain

Ser/Thr — Serine/Threonine-rich domain
PRD — Proline-rich domain

Superdex 200 Increase 10/300 GL

SEQUENCE LISTING

```
Sequence total quantity: 110
SEQ ID NO: 1            moltype = AA   length = 136
FEATURE                 Location/Qualifiers
source                  1..136
                        mol_type = protein
                        organism = Synthetic Construct
SEQUENCE: 1
METDTLLLWV LLLWVPGSTG QVKLVQSGGG LVQAGGSLRL SCAASGSIFS SASMGWYRQA   60
PGKPREQVAS ITRDGNTYYE DDVKGRFTIS RDNARSTGYL QMNSLTPEDT GVYYCNVYQL  120
GFYDKWGQGT QVIVSS                                                  136

SEQ ID NO: 2            moltype = AA   length = 136
FEATURE                 Location/Qualifiers
source                  1..136
                        mol_type = protein
                        organism = Synthetic Construct
```

```
SEQUENCE: 2
METDTLLLWV LLLWVPGSTG QVKLVQSGGG LVQTGGSLRL SCAASEITFD MYSMGWYREA    60
PGKARDAVAS ITNRGNTYYA DSVKGRFTIS RDNAKKTMYL QMNSLKPEDT AVYYCNVYRT   120
GFSDYWGQGT QVTVSS                                                    136

SEQ ID NO: 3              moltype = AA   length = 136
FEATURE                   Location/Qualifiers
source                    1..136
                          mol_type = protein
                          organism = Synthetic Construct
SEQUENCE: 3
METDTLLLWV LLLWVPGSTG QVQLVQSGGG LVQPGGSLRL SCAASGITFD MYSMGWYREA    60
PGKGLEAVAS ITNRGNTYYA DSVKGRFTIS RDNAKNTLYL QMNSLRAEDT AVYYCAVYRT   120
GFSDYWGQGT LVTVSS                                                    136

SEQ ID NO: 4              moltype = AA   length = 136
FEATURE                   Location/Qualifiers
source                    1..136
                          mol_type = protein
                          organism = Construct
SEQUENCE: 4
METDTLLLWV LLLWVPGSTG QVQLVQSGGG LVQTGGSLRL SCAASGITFD MYSMGWFRQA    60
PGKGLDAVAS ITNRGNTYYA DSVKGRFTIS RDNAKNTLYL QMNSLRAEDT AVYYCNVYRT   120
GFSDYWGQGT LVTVSS                                                    136

SEQ ID NO: 5              moltype = AA   length = 136
FEATURE                   Location/Qualifiers
source                    1..136
                          mol_type = protein
                          organism = Synthetic Construct
SEQUENCE: 5
METDTLLLWV LLLWVPGSTG QVKLVQSGGG LVQTGGSLRL SCAASGITFD MYSMGWYRQA    60
PGKGLEAVAS ITNRGNTYYA DSVKGRFTIS RDNAKNTLYL QMNSLRPEDT AVYYCNVYRT   120
GFSDYWGQGT LVTVSS                                                    136

SEQ ID NO: 6              moltype = AA   length = 8
FEATURE                   Location/Qualifiers
source                    1..8
                          mol_type = protein
                          organism = Synthetic Construct
SEQUENCE: 6
GSIFSSAS                                                               8

SEQ ID NO: 7              moltype = AA   length = 7
FEATURE                   Location/Qualifiers
source                    1..7
                          mol_type = protein
                          organism = Synthetic Construct
SEQUENCE: 7
ITRDGNT                                                               7

SEQ ID NO: 8              moltype = AA   length = 10
FEATURE                   Location/Qualifiers
source                    1..10
                          mol_type = protein
                          organism = Synthetic Construct
SEQUENCE: 8
NVYQLGFYDK                                                           10

SEQ ID NO: 9              moltype = AA   length = 5
FEATURE                   Location/Qualifiers
source                    1..5
                          mol_type = protein
                          organism = Synthetic Construct
SEQUENCE: 9
SASMG                                                                 5

SEQ ID NO: 10             moltype = AA   length = 16
FEATURE                   Location/Qualifiers
source                    1..16
                          mol_type = protein
                          organism = Synthetic Construct
SEQUENCE: 10
SITRDGNTYY EDDVKG                                                    16

SEQ ID NO: 11             moltype = AA   length = 8
FEATURE                   Location/Qualifiers
source                    1..8
                          mol_type = protein
```

-continued

```
                        organism = Synthetic Construct
SEQUENCE: 11
YQLGFYDK                                                              8

SEQ ID NO: 12           moltype = AA   length = 7
FEATURE                 Location/Qualifiers
source                  1..7
                        mol_type = protein
                        organism = Synthetic Construct
SEQUENCE: 12
GSIFSSA                                                               7

SEQ ID NO: 13           moltype = AA   length = 5
FEATURE                 Location/Qualifiers
source                  1..5
                        mol_type = protein
                        organism = Synthetic Construct
SEQUENCE: 13
TRDGN                                                                 5

SEQ ID NO: 14           moltype = AA   length = 13
FEATURE                 Location/Qualifiers
source                  1..13
                        mol_type = protein
                        organism = Synthetic Construct
SEQUENCE: 14
AASGSIFSSA SMG                                                        13

SEQ ID NO: 15           moltype = AA   length = 9
FEATURE                 Location/Qualifiers
source                  1..9
                        mol_type = protein
                        organism = Synthetic Construct
SEQUENCE: 15
SITRDGNTY                                                             9

SEQ ID NO: 16           moltype = AA   length = 6
FEATURE                 Location/Qualifiers
source                  1..6
                        mol_type = protein
                        organism = Synthetic Construct
SEQUENCE: 16
SSASMG                                                                6

SEQ ID NO: 17           moltype = AA   length = 12
FEATURE                 Location/Qualifiers
source                  1..12
                        mol_type = protein
                        organism = Synthetic Construct
SEQUENCE: 17
QVASITRDGN TY                                                         12

SEQ ID NO: 18           moltype = AA   length = 9
FEATURE                 Location/Qualifiers
source                  1..9
                        mol_type = protein
                        organism = Synthetic Construct
SEQUENCE: 18
NVYQLGFYD                                                             9

SEQ ID NO: 19           moltype = AA   length = 8
FEATURE                 Location/Qualifiers
source                  1..8
                        mol_type = protein
                        organism = Synthetic Construct
SEQUENCE: 19
EITFDMYS                                                              8

SEQ ID NO: 20           moltype = AA   length = 7
FEATURE                 Location/Qualifiers
source                  1..7
                        mol_type = protein
                        organism = Synthetic Construct
SEQUENCE: 20
ITNRGNT                                                               7

SEQ ID NO: 21           moltype = AA   length = 10
FEATURE                 Location/Qualifiers
source                  1..10
```

```
                              mol_type = protein
                              organism = Synthetic Construct
SEQUENCE: 21
NVYRTGFSDY                                                          10

SEQ ID NO: 22              moltype = AA   length = 5
FEATURE                    Location/Qualifiers
source                     1..5
                           mol_type = protein
                           organism = Synthetic Construct
SEQUENCE: 22
MYSMG                                                               5

SEQ ID NO: 23              moltype = AA   length = 16
FEATURE                    Location/Qualifiers
source                     1..16
                           mol_type = protein
                           organism = Synthetic Construct
SEQUENCE: 23
SITNRGNTYY ADSVKG                                                   16

SEQ ID NO: 24              moltype = AA   length = 8
FEATURE                    Location/Qualifiers
source                     1..8
                           mol_type = protein
                           organism = Synthetic Construct
SEQUENCE: 24
YRTGFSDY                                                            8

SEQ ID NO: 25              moltype = AA   length = 7
FEATURE                    Location/Qualifiers
source                     1..7
                           mol_type = protein
                           organism = Synthetic Construct
SEQUENCE: 25
EITFDMY                                                             7

SEQ ID NO: 26              moltype = AA   length = 5
FEATURE                    Location/Qualifiers
source                     1..5
                           mol_type = protein
                           organism = Synthetic Construct
SEQUENCE: 26
TNRGN                                                               5

SEQ ID NO: 27              moltype = AA   length = 13
FEATURE                    Location/Qualifiers
source                     1..13
                           mol_type = protein
                           organism = Synthetic Construct
SEQUENCE: 27
AASEITFDMY SMG                                                      13

SEQ ID NO: 28              moltype = AA   length = 9
FEATURE                    Location/Qualifiers
source                     1..9
                           mol_type = protein
                           organism = Synthetic Construct
SEQUENCE: 28
SITNRGNTY                                                           9

SEQ ID NO: 29              moltype = AA   length = 6
FEATURE                    Location/Qualifiers
source                     1..6
                           mol_type = protein
                           organism = Synthetic Construct
SEQUENCE: 29
DMYSMG                                                              6

SEQ ID NO: 30              moltype = AA   length = 12
FEATURE                    Location/Qualifiers
source                     1..12
                           mol_type = protein
                           organism = Synthetic Construct
SEQUENCE: 30
AVASITNRGN TY                                                       12

SEQ ID NO: 31              moltype = AA   length = 9
FEATURE                    Location/Qualifiers
```

-continued

```
source                    1..9
                          mol_type = protein
                          organism = Synthetic Construct
SEQUENCE: 31
NVYRTGFSD                                                      9

SEQ ID NO: 32             moltype = AA   length = 8
FEATURE                   Location/Qualifiers
source                    1..8
                          mol_type = protein
                          organism = Synthetic Construct
SEQUENCE: 32
GITFDMYS                                                       8

SEQ ID NO: 33             moltype = AA   length = 10
FEATURE                   Location/Qualifiers
source                    1..10
                          mol_type = protein
                          organism = Synthetic Construct
SEQUENCE: 33
AVYRTGFSDY                                                     10

SEQ ID NO: 34             moltype = AA   length = 5
FEATURE                   Location/Qualifiers
source                    1..5
                          mol_type = protein
                          organism = Synthetic Construct
SEQUENCE: 34
DMYSM                                                          5

SEQ ID NO: 35             moltype = AA   length = 7
FEATURE                   Location/Qualifiers
source                    1..7
                          mol_type = protein
                          organism = Synthetic Construct
SEQUENCE: 35
GITFDMY                                                        7

SEQ ID NO: 36             moltype = AA   length = 13
FEATURE                   Location/Qualifiers
source                    1..13
                          mol_type = protein
                          organism = Synthetic Construct
SEQUENCE: 36
AASGITFDMY SMG                                                 13

SEQ ID NO: 37             moltype = AA   length = 9
FEATURE                   Location/Qualifiers
source                    1..9
                          mol_type = protein
                          organism = Synthetic Construct
SEQUENCE: 37
AVYRTGFSD                                                      9

SEQ ID NO: 38             moltype = AA   length = 224
FEATURE                   Location/Qualifiers
source                    1..224
                          mol_type = protein
                          organism = Homo sapiens
SEQUENCE: 38
HTCPPCPAPE FFGGPSVFFF PPKPKDTFMI SRTPEVTCVV VDVSHEDPEV KFNWYVDGVE   60
VHNAKTKPRE EQYNSTYRVV SVETVFHQDW ENGKEYKCKV SNKAFPVPIE KTISKAKGQP  120
REPQVYTLPP SREEMTKNQV SLTCLVKGFY PSDIAVEWES NGQPENNYKT TPPVLDSDGP  180
FFLYSKLTVD KSRWQQGNVF SCSVMHEALH NHYTQKSLSL SPGK                  224

SEQ ID NO: 39             moltype = AA   length = 217
FEATURE                   Location/Qualifiers
source                    1..217
                          mol_type = protein
                          organism = Homo sapiens
SEQUENCE: 39
PAPPVAGPSV FLFPPKPKDT LMISRTPEVT CVVVDVSHED PEVQFNWYVD GVEVHNAKTK   60
PREEQFNSTF RVVSVLTVVH QDWLNGKEYK CKVSNKGLPA PIEKTISKTK GQPREPQVYT  120
LPPSREEMTK NQVSLTCLVK GFYPSDIAVE WESNGQPENN YKTTPPMLDS DGSFFLYSKL  180
TVDKSRWQQG NVFSCSVMHE ALHNHYTQKS LSLSPGK                          217

SEQ ID NO: 40             moltype = AA   length = 218
FEATURE                   Location/Qualifiers
source                    1..218
```

```
                           mol_type = protein
                           organism = Homo sapiens
SEQUENCE: 40
PAPELLGGPS VFLFPPKPKD TLMISRTPEV TCVVVDVSHE DPEVQFKWYV DGVEVHNAKT    60
KPREEQFNST FRVVSVLTVL HQDWLNGKEY KCKVSNKALP APIEKTISKT KGQPREPQVY   120
TLPPSREEMT KNQVSLTCLV KGFYPSDIAV EWESSGQPEN NYNTTPPMLD SDGSFFLYSK   180
LTVDKSRWQQ GNIFSCSVMH EALHNRFTQK SLSLSPGK                          218

SEQ ID NO: 41              moltype = AA   length = 218
FEATURE                    Location/Qualifiers
source                     1..218
                           mol_type = protein
                           organism = Homo sapiens
SEQUENCE: 41
PAPEFLGGPS VFLFPPKPKD TLMISRTPEV TCVVVDVSQE DPEVQFNWYV DGVEVHNAKT    60
KPREEQFNST YRVVSVLTVL HQDWLNGKEY KCKVSNKGLP SSIEKTISKA KGQPREPQVY   120
TLPPSQEEMT KNQVSLTCLV KGFYPSDIAV EWESNGQPEN NYKTTPPVLD SDGSFFLYSR   180
LTVDKSRWQE GNVFSCSVMH EALHNHYTQK SLSLSLGK                          218

SEQ ID NO: 42              moltype = AA   length = 353
FEATURE                    Location/Qualifiers
source                     1..353
                           mol_type = protein
                           organism = Homo sapiens
SEQUENCE: 42
ASPTSPKVFP LSLCSTQPDG NVVIACLVQG FFPQEPLSVT WSESGQGVTA RNFPPSQDAS    60
GDLYTTSSQL TLPATQCLAG KSVTCHVKHY TNPSQDVTVP CPVPSTPPTP SPSTPPTPSP   120
SCCHPRLSLH RPALEDLLLG SEANLTCTLT GLRDASGVTF TWTPSSGKSA VQGPPERDLC   180
GCYSVSSVLP GCAEPWNHGK TFTCTAAYPE SKTPLTATLS KSGNTFRPEV HLLPPPSEEL   240
ALNELVTLTC LARGFSPKDV LVRWLQGSQE LPREKYLTWA SRQEPSQGTT TFAVTSILRV   300
AAEDWKKGDT FSCMVGHEAL PLAFTQKTID RLAGKPTHVN VSVVMAEVDG TCY          353

SEQ ID NO: 43              moltype = AA   length = 340
FEATURE                    Location/Qualifiers
source                     1..340
                           mol_type = protein
                           organism = Homo sapiens
SEQUENCE: 43
ASPTSPKVFP LSLDSTPQDG NVVVACLVQG FFPQEPLSVT WSESGQNVTA RNFPPSQDAS    60
GDLYTTSSQL TLPATQCPDG KSVTCHVKHY TNPSQDVTVP CPVPPPPPCC HPRLSLHRPA   120
LEDLLLGSEA NLTCTLTGLR DASGATFTWT PSSGKSAVQG PPERDLCGCY SVSSVLPGCA   180
QPWNHGETFT CTAAHPELKT PLTANITKSG NTFRPEVHLL PPPSEELALN ELVTLTCLAR   240
GFSPKDVLVR WLQGSQELPR EKYLTWASRQ EPSQGTTTFA VTSILRVAAE DWKKGDTFSC   300
MVGHEALPLA FTQKTIDRLA GKPTHVNVSV VMAEVDGTCY                         340

SEQ ID NO: 44              moltype = AA   length = 764
FEATURE                    Location/Qualifiers
source                     1..764
                           mol_type = protein
                           organism = Homo sapiens
SEQUENCE: 44
MLLFVLTCLL AVFPAISTKS PIFGPEEVNS VEGNSVSITC YYPPTSVNRH TRKYWCRQGA    60
RGGCITLISS EGYVSSKYAG RANLTNFPEN GTFVVNIAQL SQDDSGRYKC GLGINSRGLS   120
FDVSLEVSQG PGLLNDTKVY TVDLGRTVTI NCPFKTENAQ KRKSLYKQIG LYPVLVIDSS   180
GYVNPNYTGR IRLDIQGTGQ LLFSVVINQL RLSDAGQYLC QAGDDSNSNK KNADLQVLKP   240
EPELVYEDLR GSVTFHCALG PEVANVAKFL CRQSSGENCD VVVNTLGKRA PAFEGRILLN   300
PQDKDGSFSV VITGLRKEDA GRYLCGAHSD GQLQEGSPIQ AWQLFVNEES TIPRSPTVVK   360
GVAGGSVAVL CPYNRKESKS IKYWCLWEGA QNGRCPLLVD SEGWVKAQYE GRLSLLEEPG   420
NGTFTVILNQ LTSRDAGFYW CLTNGDTLWR TTVEIKIIEG EPNLKVPGNV TAVLGETLKV   480
PCHFPCKFSS YEKYWCKWNN TGCQALPSQD EGPSKAFVNC DENSRLVSLT LNLVTRADEG   540
WYWCGVKQGH FYGETAAVYV AVEERKAAGS RDVSLAKADA APDEKVLDSG FREIENKAIQ   600
DPRLFAEEKA VADTRDQADG SRASVDSGSS EEQGGSSRAL VSTLVPLGLV LAVGAVAVGV   660
ARARHRKNVD RVSIRSYRTD ISMSDFENSR EFGANDNMGA SSITQETSLG GKEEFVATTE   720
STTETKEPKK AKRSSKEEAE MAYKDFLLQS STVAAEAQDG PQEA                    764

SEQ ID NO: 45              moltype = AA   length = 585
FEATURE                    Location/Qualifiers
source                     1..585
                           mol_type = protein
                           organism = Homo sapiens
SEQUENCE: 45
KSPIFGPEEV NSVEGNSVSI TCYYPPTSVN RHTRKYWCRQ GARGGCITLI SSEGYVSSKY    60
AGRANLTNFP ENGTFVVNIA QLSQDDSGRY KCGLGINSRG LSFDVSLEVS QGPGLLNDTK   120
VYTVDLGRTV TINCPFKTEN AQKRKSLYKQ IGLYPVLVID SSGYVNPNYT GRIRLDIQGT   180
GQLLFSVVIN QLRLSDAGQY LCQAGDDSNS NKKNADLQVL KPEPELVYED LRGSVTFHCA   240
LGPEVANVAK FLCRQSSGEN CDVVVNTLGK RAPAFEGRIL LNPQDKDGSF SVVITGLRKE   300
DAGRYLCGAH SDGQLQEGSP IQAWQLFVNE ESTIPRSPTV VKGVAGGSVA VLCPYNRKES   360
KSIKYWCLWE GAQNGRCPLL VDSEGWVKAQ YEGRLSLLEE PGNGTFTVIL NQLTSRDAGF   420
YWCLTNGDTL WRTTVEIKII EGEPNLKVPG NVTAVLGETL KVPCHFPCKF SSYEKYWCKW   480
```

```
NNTGCQALPS QDEGPSKAFV NCDENSRLVS LTLNLVTRAD EGWYWCGVKQ GHFYGETAAV    540
YVAVEERKAA GSRDVSLAKA DAAPDEKVLD SGFREIENKA IQDPR                    585

SEQ ID NO: 46              moltype = AA  length = 137
FEATURE                    Location/Qualifiers
source                     1..137
                           mol_type = protein
                           organism = Homo sapiens
SEQUENCE: 46
QEDERIVLVD NKCKCARITS RIIRSSEDPN EDIVERNIRI IVPLNNRENI SDPTSPLRTR    60
FVYHLSDLCK KCDPTEVELD NQIVTATQSN ICDEDSATET CYTYDRNKCY TAVVPLVYGG    120
ETKMVETALT PDACYPD                                                  137

SEQ ID NO: 47              moltype = AA  length = 5
FEATURE                    Location/Qualifiers
source                     1..5
                           mol_type = protein
                           organism = Synthetic Construct
SEQUENCE: 47
GGGGS                                                               5

SEQ ID NO: 48              moltype = AA  length = 9
FEATURE                    Location/Qualifiers
source                     1..9
                           mol_type = protein
                           organism = Synthetic Construct
SEQUENCE: 48
GGGSGGGGS                                                           9

SEQ ID NO: 49              moltype = AA  length = 7
FEATURE                    Location/Qualifiers
source                     1..7
                           mol_type = protein
                           organism = Synthetic Construct
SEQUENCE: 49
GGGSGGS                                                             7

SEQ ID NO: 50              moltype = AA  length = 9
FEATURE                    Location/Qualifiers
source                     1..9
                           mol_type = protein
                           organism = Synthetic Construct
SEQUENCE: 50
GGGSGGGGS                                                           9

SEQ ID NO: 51              moltype = AA  length = 20
FEATURE                    Location/Qualifiers
source                     1..20
                           mol_type = protein
                           organism = Synthetic Construct
SEQUENCE: 51
GGGGSGGGGS GGGGSGGGGS                                               20

SEQ ID NO: 52              moltype = AA  length = 15
FEATURE                    Location/Qualifiers
source                     1..15
                           mol_type = protein
                           organism = Synthetic Construct
SEQUENCE: 52
GGGGSGGGGS GGGGS                                                    15

SEQ ID NO: 53              moltype = AA  length = 10
FEATURE                    Location/Qualifiers
source                     1..10
                           mol_type = protein
                           organism = Synthetic Construct
SEQUENCE: 53
GGGGSGGGGS                                                          10

SEQ ID NO: 54              moltype = AA  length = 5
FEATURE                    Location/Qualifiers
source                     1..5
                           mol_type = protein
                           organism = Synthetic Construct
SEQUENCE: 54
GGGGS                                                               5

SEQ ID NO: 55              moltype = AA  length = 8
FEATURE                    Location/Qualifiers
```

```
source                  1..8
                        mol_type = protein
                        organism = Synthetic Construct
SEQUENCE: 55
GGGSGGGS                                                               8

SEQ ID NO: 56           moltype = AA  length = 4
FEATURE                 Location/Qualifiers
source                  1..4
                        mol_type = protein
                        organism = Synthetic Construct
SEQUENCE: 56
GGGS                                                                   4

SEQ ID NO: 57           moltype = AA  length = 6
FEATURE                 Location/Qualifiers
source                  1..6
                        mol_type = protein
                        organism = Synthetic Construct
SEQUENCE: 57
GGSGGS                                                                 6

SEQ ID NO: 58           moltype = AA  length = 11
FEATURE                 Location/Qualifiers
source                  1..11
                        mol_type = protein
                        organism = Synthetic Construct
SEQUENCE: 58
GGSGGGSGGS G                                                          11

SEQ ID NO: 59           moltype = AA  length = 10
FEATURE                 Location/Qualifiers
source                  1..10
                        mol_type = protein
                        organism = Synthetic Construct
SEQUENCE: 59
GGSGGGSGSG                                                            10

SEQ ID NO: 60           moltype = AA  length = 8
FEATURE                 Location/Qualifiers
source                  1..8
                        mol_type = protein
                        organism = Synthetic Construct
SEQUENCE: 60
GGSGGGSG                                                               8

SEQ ID NO: 61           moltype = AA  length = 112
FEATURE                 Location/Qualifiers
source                  1..112
                        mol_type = protein
                        organism = Synthetic Construct
SEQUENCE: 61
DIQLTQSPSS LSASVGDRVT ITCKASQSVD YDGDSYLNWY QQIPGKAPKL LIYDASNLVS     60
GIPPRFSGSG SGTDYTFTIS SLQPEDIATY HCQQSTEDPW TFGGGTKLQI KR             112

SEQ ID NO: 62           moltype = AA  length = 124
FEATURE                 Location/Qualifiers
source                  1..124
                        mol_type = protein
                        organism = Synthetic Construct
SEQUENCE: 62
QVQLQQSGAE VKKPGSSVKV SCKASGYAFS SYWMNWVRQR PGQGLEWIGQ IWPGDGDTNY     60
NGKFKGRATI TADESTNTAY MELSSLRSED TAFYSCARRE TTTVGRYYYA MDYWGQGTTV     120
TVSS                                                                  124

SEQ ID NO: 63           moltype = AA  length = 5
FEATURE                 Location/Qualifiers
source                  1..5
                        mol_type = protein
                        organism = Synthetic Construct
SEQUENCE: 63
DYYMH                                                                  5

SEQ ID NO: 64           moltype = AA  length = 7
FEATURE                 Location/Qualifiers
source                  1..7
                        mol_type = protein
                        organism = Synthetic Construct
SEQUENCE: 64
```

-continued

```
SRLHSGV                                                          7

SEQ ID NO: 65        moltype = AA  length = 9
FEATURE              Location/Qualifiers
source               1..9
                     mol_type = protein
                     organism = Synthetic Construct

SEQUENCE: 65
GNTLPYTFG                                                        9

SEQ ID NO: 66        moltype = AA  length = 5
FEATURE              Location/Qualifiers
source               1..5
                     mol_type = protein
                     organism = Synthetic Construct

SEQUENCE: 66
DYGVS                                                            5

SEQ ID NO: 67        moltype = AA  length = 16
FEATURE              Location/Qualifiers
source               1..16
                     mol_type = protein
                     organism = Synthetic Construct

SEQUENCE: 67
VTWGSETTYY NSALKS                                                16

SEQ ID NO: 68        moltype = AA  length = 7
FEATURE              Location/Qualifiers
source               1..7
                     mol_type = protein
                     organism = Synthetic Construct

SEQUENCE: 68
YAMDYWG                                                          7

SEQ ID NO: 69        moltype = AA  length = 15
FEATURE              Location/Qualifiers
source               1..15
                     mol_type = protein
                     organism = Synthetic Construct

SEQUENCE: 69
KASQSVDYDG DSYLN                                                 15

SEQ ID NO: 70        moltype = AA  length = 7
FEATURE              Location/Qualifiers
source               1..7
                     mol_type = protein
                     organism = Synthetic Construct

SEQUENCE: 70
DASNLVS                                                          7

SEQ ID NO: 71        moltype = AA  length = 9
FEATURE              Location/Qualifiers
source               1..9
                     mol_type = protein
                     organism = Synthetic Construct

SEQUENCE: 71
QQSTEDPWT                                                        9

SEQ ID NO: 72        moltype = AA  length = 5
FEATURE              Location/Qualifiers
source               1..5
                     mol_type = protein
                     organism = Synthetic Construct

SEQUENCE: 72
SYWMN                                                            5

SEQ ID NO: 73        moltype = AA  length = 17
FEATURE              Location/Qualifiers
source               1..17
                     mol_type = protein
                     organism = Synthetic Construct

SEQUENCE: 73
QIWPGDGDTN YNGKFKG                                               17

SEQ ID NO: 74        moltype = AA  length = 15
FEATURE              Location/Qualifiers
source               1..15
                     mol_type = protein
                     organism = Synthetic Construct
```

-continued

```
SEQUENCE: 74
RETTTVGRYY YAMDY                                                   15

SEQ ID NO: 75          moltype = AA   length = 52
FEATURE                Location/Qualifiers
source                 1..52
                       mol_type = protein
                       organism = Synthetic Construct
SEQUENCE: 75
DITGAALLEA KEAAINELKQ YGISDYYVTL INKAKTVEGV NALKAEILSA LP          52

SEQ ID NO: 76          moltype = AA   length = 45
FEATURE                Location/Qualifiers
source                 1..45
                       mol_type = protein
                       organism = Synthetic Construct
SEQUENCE: 76
LKEAKEKAIE ELKKAGITSD YYFDLINKAK TVEGVNALKD EILKA                 45

SEQ ID NO: 77          moltype = AA   length = 107
FEATURE                Location/Qualifiers
source                 1..107
                       mol_type = protein
                       organism = Synthetic Construct
SEQUENCE: 77
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINR               107

SEQ ID NO: 78          moltype = AA   length = 192
FEATURE                Location/Qualifiers
source                 1..192
                       mol_type = protein
                       organism = Synthetic Construct
SEQUENCE: 78
QVQLQQSGAE LARPGASVKM SCKASGYTFT RYTMHWVKQR PGQGLEWIGY INPSRGYTNY  60
NQKFKDKATL TTDKSSSTAY MQLSSLTSED SAVYYCARYY DDHYCLDYWG QGTTLTVSSA  120
KTTAPSVYPL APVCGDTTGS SVTLGCLVKG YFPEPVTLTW NSGSLSSGVH TFPAVLQSDL  180
YTLSSSVTVT SS                                                     192

SEQ ID NO: 79          moltype = AA   length = 10
FEATURE                Location/Qualifiers
source                 1..10
                       mol_type = protein
                       organism = Synthetic Construct
SEQUENCE: 79
SASSSVSYMN                                                         10

SEQ ID NO: 80          moltype = AA   length = 7
FEATURE                Location/Qualifiers
source                 1..7
                       mol_type = protein
                       organism = Synthetic Construct
SEQUENCE: 80
DTSKLAS                                                            7

SEQ ID NO: 81          moltype = AA   length = 10
FEATURE                Location/Qualifiers
source                 1..10
                       mol_type = protein
                       organism = Synthetic Construct
SEQUENCE: 81
QQWSSNPFTF                                                         10

SEQ ID NO: 82          moltype = AA   length = 5
FEATURE                Location/Qualifiers
source                 1..5
                       mol_type = protein
                       organism = Synthetic Construct
SEQUENCE: 82
RYTMH                                                              5

SEQ ID NO: 83          moltype = AA   length = 17
FEATURE                Location/Qualifiers
source                 1..17
                       mol_type = protein
                       organism = Synthetic Construct
SEQUENCE: 83
YINPSRGYTN YNQKFKD                                                 17
```

-continued

```
SEQ ID NO: 84            moltype = AA  length = 8
FEATURE                  Location/Qualifiers
source                   1..8
                         mol_type = protein
                         organism = Synthetic Construct
SEQUENCE: 84
YYDDHYCL                                                              8

SEQ ID NO: 85            moltype = AA  length = 108
FEATURE                  Location/Qualifiers
source                   1..108
                         mol_type = protein
                         organism = Synthetic Construct
SEQUENCE: 85
DIQMTQSPSS LSASVGDRVT ITCKTNENIY SNLAWYQQKD GKSPQLLIYA ATHLVEGVPS     60
RFSGSGSGTQ YSLTISSLQP EDFGNYYCQH FWGTPXTFGG GTKLEIKR                 108

SEQ ID NO: 86            moltype = AA  length = 120
FEATURE                  Location/Qualifiers
source                   1..120
                         mol_type = protein
                         organism = Synthetic Construct
SEQUENCE: 86
VQLQQSGAEL KKPGASVKVS CKASGYTFTE YIIHWIKLRS GQGLEWIGWF YPGSNDIQYN     60
AQFKGKATLT ADKSSSTVYM ELTGLTPEDS AVYFCARRDD FSGYDALPYW GQGTLVTVSA    120

SEQ ID NO: 87            moltype = AA  length = 11
FEATURE                  Location/Qualifiers
source                   1..11
                         mol_type = protein
                         organism = Synthetic Construct
SEQUENCE: 87
HASQNIYVWL N                                                         11

SEQ ID NO: 88            moltype = AA  length = 7
FEATURE                  Location/Qualifiers
source                   1..7
                         mol_type = protein
                         organism = Synthetic Construct
SEQUENCE: 88
KASNLHT                                                               7

SEQ ID NO: 89            moltype = AA  length = 9
FEATURE                  Location/Qualifiers
source                   1..9
                         mol_type = protein
                         organism = Synthetic Construct
SEQUENCE: 89
QQGQTYPYT                                                             9

SEQ ID NO: 90            moltype = AA  length = 5
FEATURE                  Location/Qualifiers
source                   1..5
                         mol_type = protein
                         organism = Synthetic Construct
SEQUENCE: 90
SYYIH                                                                 5

SEQ ID NO: 91            moltype = AA  length = 17
FEATURE                  Location/Qualifiers
source                   1..17
                         mol_type = protein
                         organism = Synthetic Construct
SEQUENCE: 91
CIYPGNVNTN YNEKFKD                                                   17

SEQ ID NO: 92            moltype = AA  length = 11
FEATURE                  Location/Qualifiers
source                   1..11
                         mol_type = protein
                         organism = Synthetic Construct
SEQUENCE: 92
SHYGLDWNFD V                                                         11

SEQ ID NO: 93            moltype = AA  length = 7
FEATURE                  Location/Qualifiers
source                   1..7
                         mol_type = protein
                         organism = Synthetic Construct
```

```
SEQUENCE: 93
RASQSVS                                                                              7

SEQ ID NO: 94          moltype = AA  length = 6
FEATURE                Location/Qualifiers
source                 1..6
                       mol_type = protein
                       organism = Synthetic Construct
SEQUENCE: 94
ASNRAT                                                                               6

SEQ ID NO: 95          moltype = AA  length = 10
FEATURE                Location/Qualifiers
source                 1..10
                       mol_type = protein
                       organism = Synthetic Construct
SEQUENCE: 95
QRSNWPPALT                                                                          10

SEQ ID NO: 96          moltype = AA  length = 4
FEATURE                Location/Qualifiers
source                 1..4
                       mol_type = protein
                       organism = Synthetic Construct
SEQUENCE: 96
YYWS                                                                                 4

SEQ ID NO: 97          moltype = AA  length = 12
FEATURE                Location/Qualifiers
source                 1..12
                       mol_type = protein
                       organism = Synthetic Construct
SEQUENCE: 97
YGPGNYDWYF DL                                                                       12

SEQ ID NO: 98          moltype = AA  length = 6
FEATURE                Location/Qualifiers
source                 1..6
                       mol_type = protein
                       organism = Synthetic Construct
SEQUENCE: 98
HHHHHH                                                                               6

SEQ ID NO: 99          moltype = AA  length = 7
FEATURE                Location/Qualifiers
source                 1..7
                       mol_type = protein
                       organism = Synthetic Construct
SEQUENCE: 99
DYKDDDD                                                                              7

SEQ ID NO: 100         moltype = AA  length = 8
FEATURE                Location/Qualifiers
source                 1..8
                       mol_type = protein
                       organism = Synthetic Construct
SEQUENCE: 100
DLYDDDDK                                                                             8

SEQ ID NO: 101         moltype = AA  length = 15
FEATURE                Location/Qualifiers
source                 1..15
                       mol_type = protein
                       organism = Synthetic Construct
SEQUENCE: 101
GLNDIFEAQK IEWHE                                                                    15

SEQ ID NO: 102         moltype = AA  length = 26
FEATURE                Location/Qualifiers
source                 1..26
                       mol_type = protein
                       organism = Synthetic Construct
SEQUENCE: 102
KRRWKKNFIA VSAANRFKKI SSSGAL                                                        26

SEQ ID NO: 103         moltype = AA  length = 6
FEATURE                Location/Qualifiers
source                 1..6
                       mol_type = protein
```

-continued

```
                          organism = Synthetic Construct
SEQUENCE: 103
EEEEEE                                                                      6

SEQ ID NO: 104           moltype = AA   length = 9
FEATURE                  Location/Qualifiers
source                   1..9
                         mol_type = protein
                         organism = Synthetic Construct
SEQUENCE: 104
YPYDVPDYA                                                                    9

SEQ ID NO: 105           moltype = AA   length = 10
FEATURE                  Location/Qualifiers
source                   1..10
                         mol_type = protein
                         organism = Synthetic Construct
SEQUENCE: 105
EQKLISEEDL                                                                  10

SEQ ID NO: 106           moltype = AA   length = 8
FEATURE                  Location/Qualifiers
source                   1..8
                         mol_type = protein
                         organism = Synthetic Construct
SEQUENCE: 106
WRHPQFGG                                                                     8

SEQ ID NO: 107           moltype = AA   length = 8
FEATURE                  Location/Qualifiers
source                   1..8
                         mol_type = protein
                         organism = Synthetic Construct
SEQUENCE: 107
WSHPQFEK                                                                     8

SEQ ID NO: 108           moltype = AA   length = 13
FEATURE                  Location/Qualifiers
source                   1..13
                         mol_type = protein
                         organism = Synthetic Construct
SEQUENCE: 108
SLAELLNAGL GGS                                                              13

SEQ ID NO: 109           moltype = AA   length = 8
FEATURE                  Location/Qualifiers
source                   1..8
                         mol_type = protein
                         organism = Synthetic Construct
SEQUENCE: 109
TQDPSRVG                                                                     8

SEQ ID NO: 110           moltype = AA   length = 14
FEATURE                  Location/Qualifiers
source                   1..14
                         mol_type = protein
                         organism = Synthetic Construct
SEQUENCE: 110
GKPIPNPLLG LDST                                                             14
```

SINGLE-DOMAIN ANTIBODIES THAT BIND ROR1

CROSS REFERENCE TO RELATED APPLICATION

This application claims priority to U.S. Provisional Patent Application No. 63/388,157 filed Jul. 11, 2022, the entire contents of which are incorporated by reference herein.

REFERENCE TO SEQUENCE LISTING

The Sequence Listing associated with this application is provided in XML format in lieu of a paper copy and is hereby incorporated by reference into the specification. The name of the file containing the Sequence Listing is 2XD6064.xml. The file is 99 KB, was created on Jul. 11, 2023, and is being submitted electronically via Patent Center.

FIELD OF THE DISCLOSURE

The current disclosure describes single-domain antibodies that bind receptor tyrosine kinase (ROR1). The single-domain antibodies can be used for multiple purposes including in research, treatment, imaging, and diagnosis of ROR1-related conditions.

BACKGROUND OF THE DISCLOSURE

The receptor tyrosine kinase (ROR1) is an oncofetal antigen that is overexpressed by a wide variety of cancer cells yet is minimally expressed by normal tissues. For example, ROR1 is highly expressed in B-cell chronic lymphocytic leukemia (CLL), mantle cell lymphoma (MCL), and in some epithelial cancers. Based on high expression of ROR1 by cancer cells and minimal ROR1 expression in normal tissues, ROR1 is a good cancer cell-specific antigen to target with therapeutics. For example, T cells expressing a chimeric antigen receptor (CAR) have been designed to target ROR1-expressing cancers (Hudecek et al., Blood 116: 4532-41, 2010).

Beyond CAR, ROR1 can serve as a therapeutic target for other receptor binding proteins such as conventional human antibodies. Traditional conventional antibodies, however, have large molecular weights and difficulty penetrating into tissues. Further, the production cycle of conventional antibodies is long.

Naturally occurring single-domain antibodies were first discovered by Muyldermans et al. at the Free University of Brussels in 1989. Unlike conventional antibodies that have 2 heavy chains and 2 light chains, single-domain antibodies have only 2 heavy chains and retain the antigen binding domain called the VHH region but lack the CH1 region. Single-domain antibodies generally have a molecular weight of 15 kDa, and a nanometer molecular size, providing unique characteristics when compared to conventional antibodies. Some of these characteristics include increased stability, increased water solubility, simpler humanization strategies, and increased penetration into tissues.

SUMMARY OF THE DISCLOSURE

The current disclosure provides novel single-domain antibodies that bind receptor tyrosine kinase (ROR1). The single-domain antibodies can be used for multiple purposes including in research, treatment, imaging, and diagnosis of ROR1-related conditions. For example, the disclosed single-domain antibodies can be used as anti-cancer therapeutics such as antibody drug conjugates and as immune targeting reagents (e.g., multi-domain binding molecules or recombinant receptors) and can also be used as cancer imaging/diagnostic agents.

In particular embodiments, a single-domain antibody that binds ROR1 includes Nb11 WT (SEQ ID NO: 1). In particular embodiments, a single-domain antibody that binds ROR1 includes Nb14 WT (SEQ ID NO: 2). In particular embodiments, a single-domain antibody that binds ROR1 includes huNb14 Lo1 (SEQ ID NO: 3). In particular embodiments, a single-domain antibody that binds ROR1 includes huNb14 Mid1 (SEQ ID NO: 4). In particular embodiments, a single-domain antibody that binds ROR1 includes huNb14 Hi2 (SEQ ID NO: 5).

BRIEF DESCRIPTION OF THE FIGURES

Some of the drawings submitted herewith may be better understood in color. Applicant considers the color versions of the drawings as part of the original submission and reserves the right to present color images of the drawings in later proceedings.

Figure 1C:
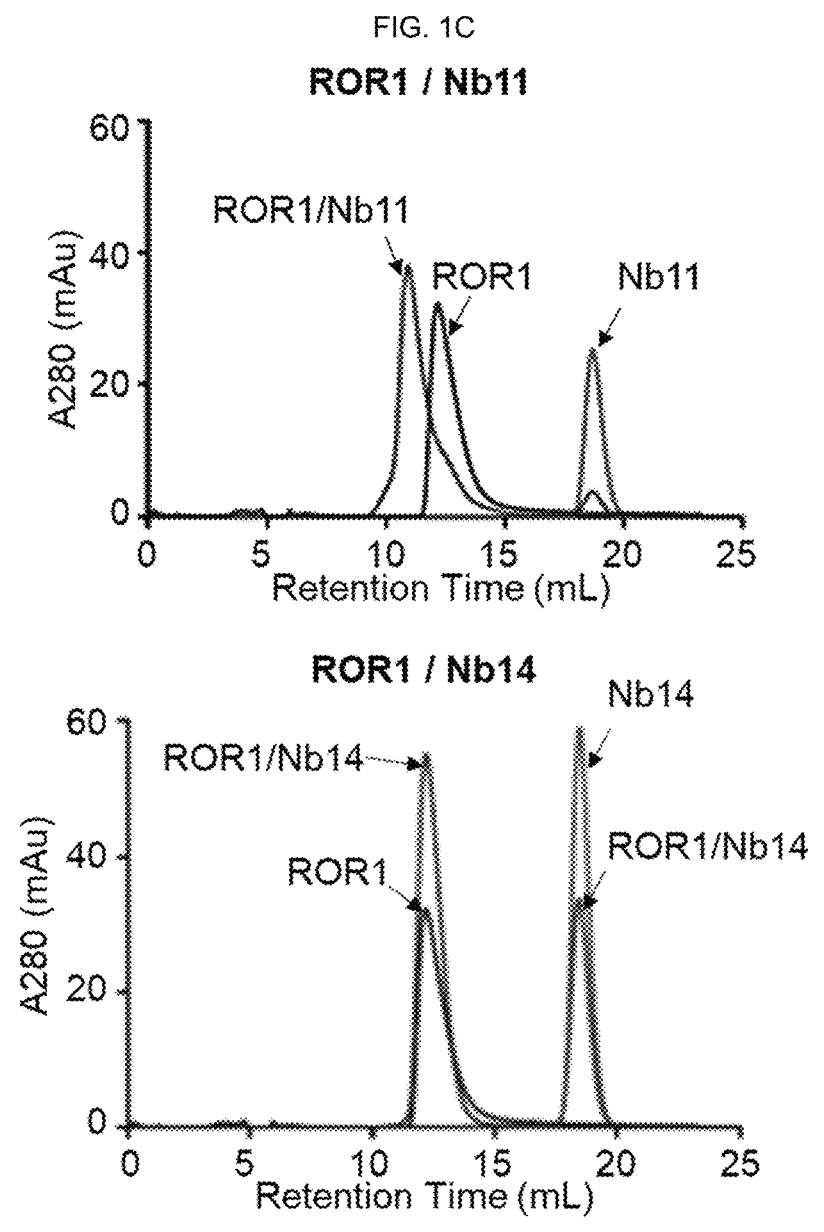

FIGS. 1A-1D. ROR1 targeting single-domain antibodies, Nb11 and Nb14, specifically bind to soluble and endogenously expressed ROR1 with Kd=2 nM. (1A) Schematic of a single-domain antibody or VHH and a VHH-Fc fusion antibody (also referred to as heavy chain only antibody HcAb). (1B) Gel showing expression of VHH-Fc and VHH with expression controls. (1C) Anti-ROR1 nanobodies complex with soluble ROR1 ectodomain by size exclusion chromatography (SEC). (1D) Anti-ROR1 Nb-Fc fusions stain cancer cell lines with the same pattern as mAb 2A2.

DETAILED DESCRIPTION

Figure 1A:
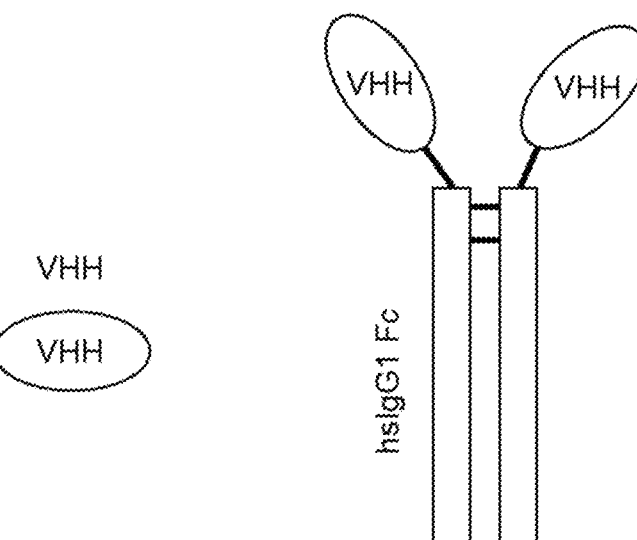
Figure 1B:
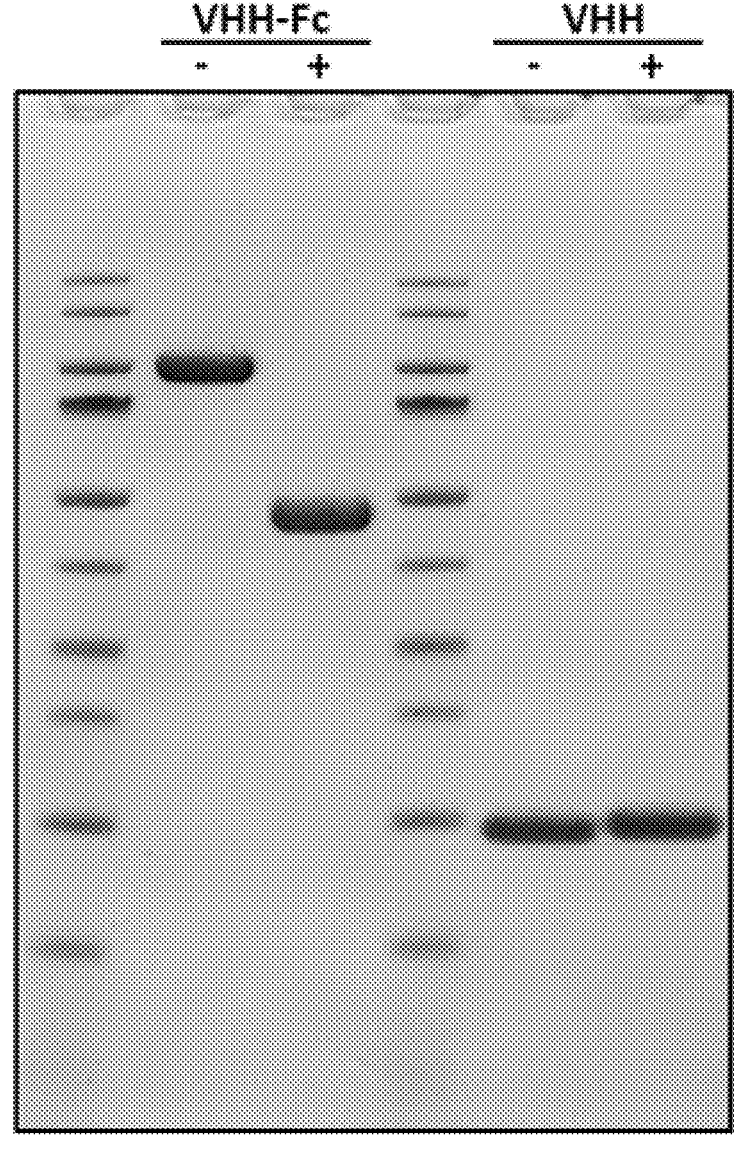
Figure 1D:
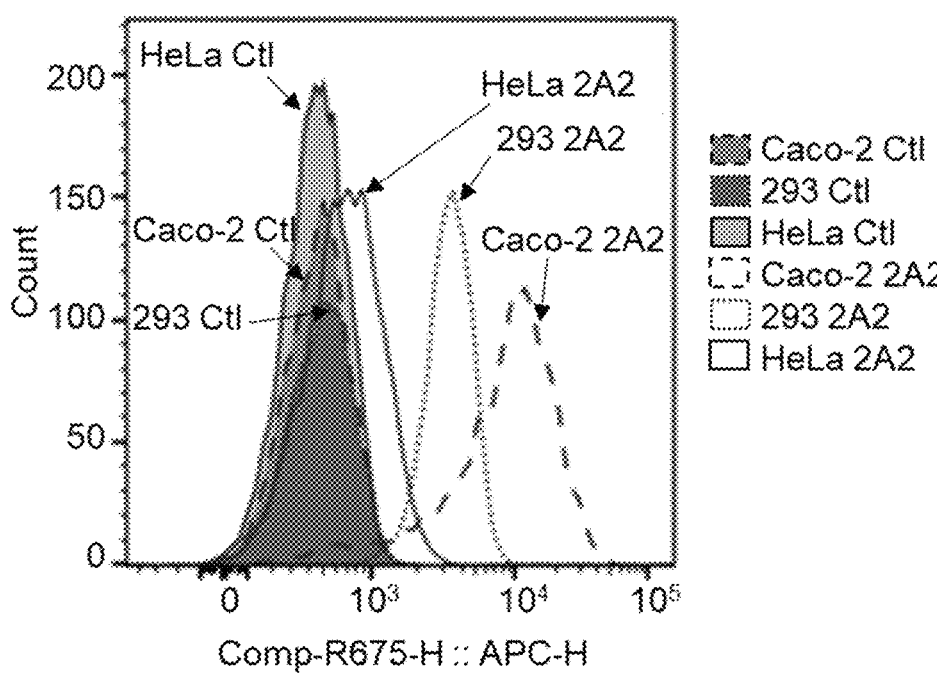
Figure 1D:
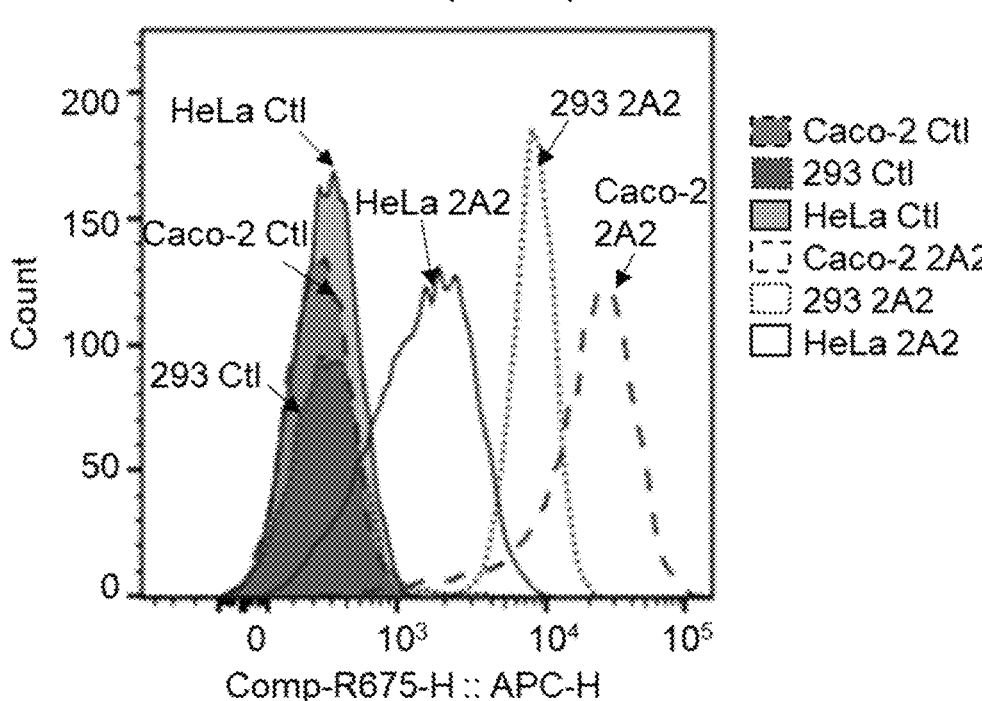
Figure 1D:
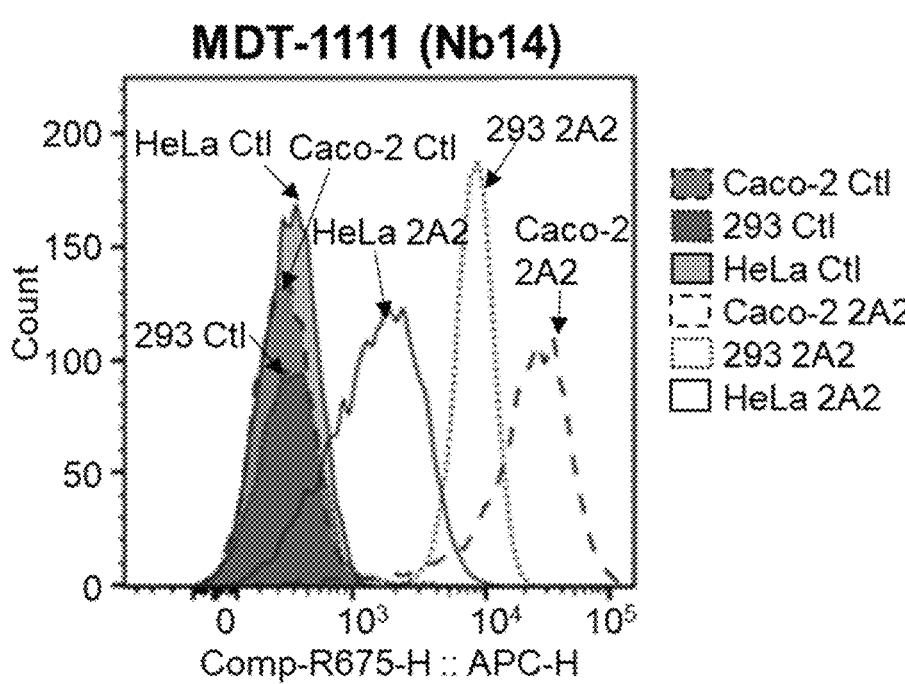
Figure 2A:
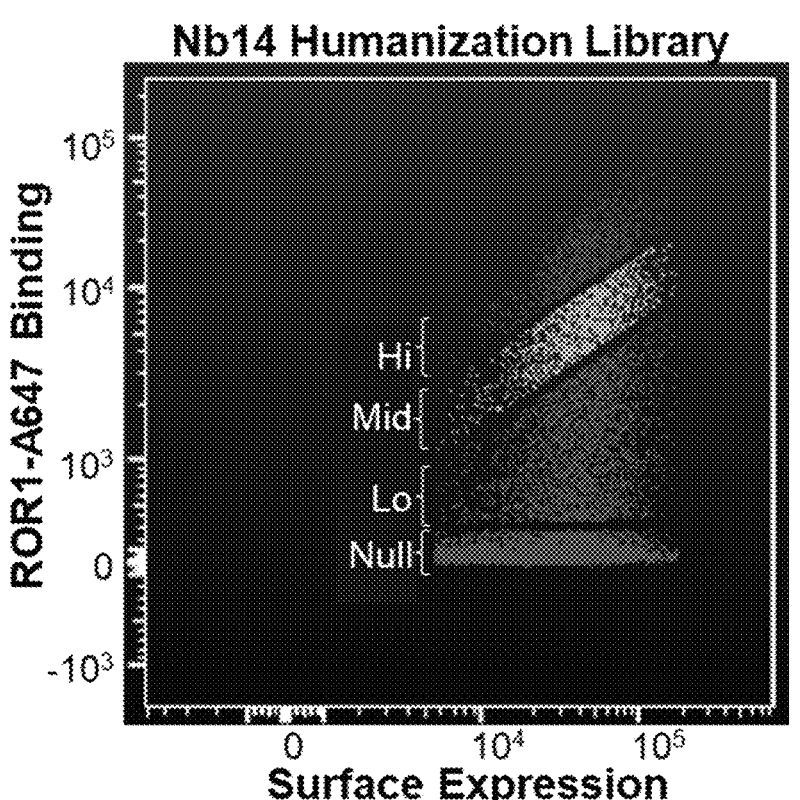
FIGS. 2A-2D. Humanized and affinity tune variants. (2A) Surface expression compared to ROR1-A647 binding for huNb14 Lo1, huNb14 Mid1, and huNb14 Hi2. (2B) Landscape of affinities. (2C) Humanized variants validated with surface display. (2D) Dissociation constants determined by plotting response (RU) over time for huNb14 Lo1, huNb14 Mid1, and huNb14 Hi2. Kd determined by Carterra.
Figure 2B:
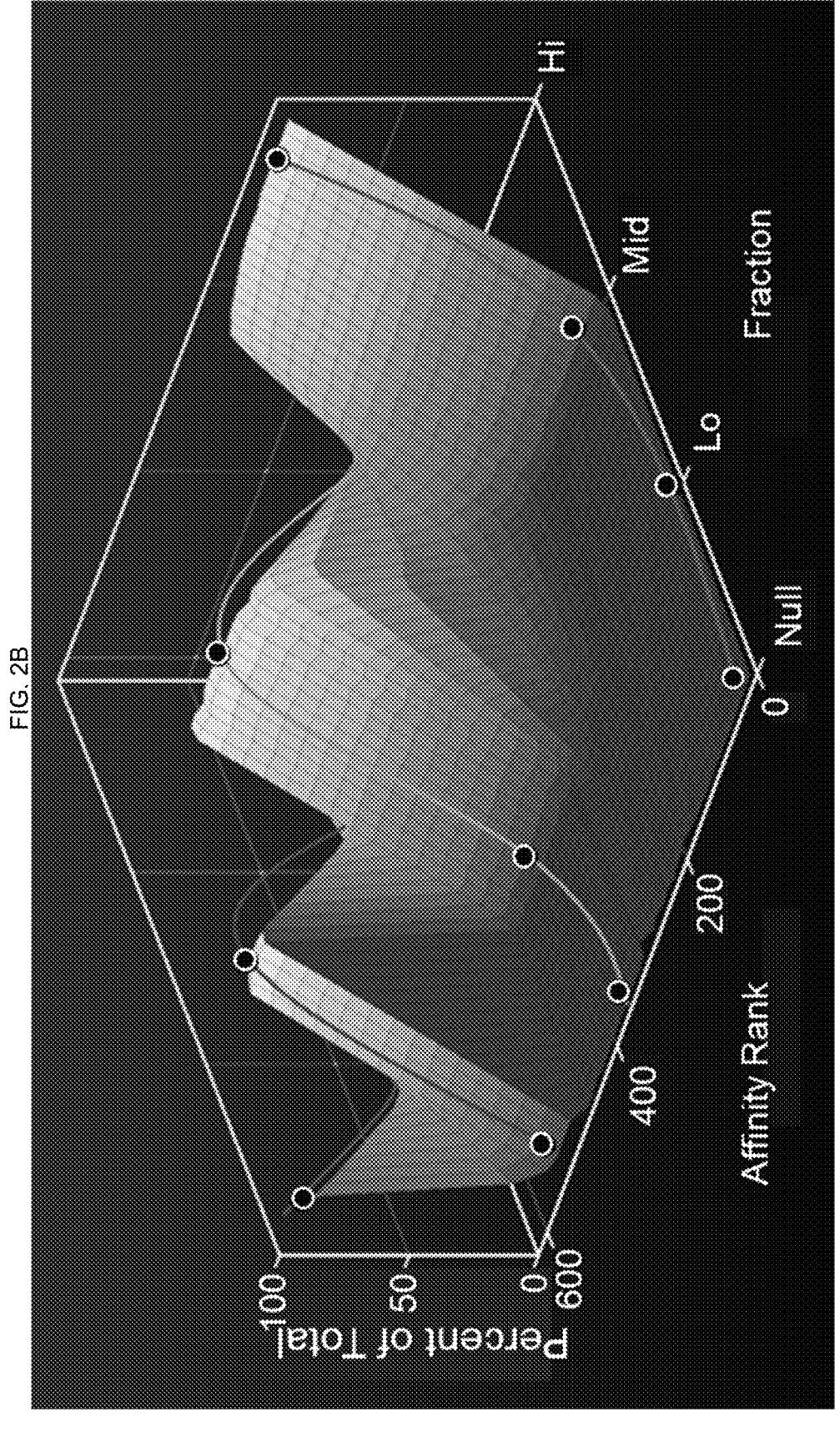
Figure 2C:
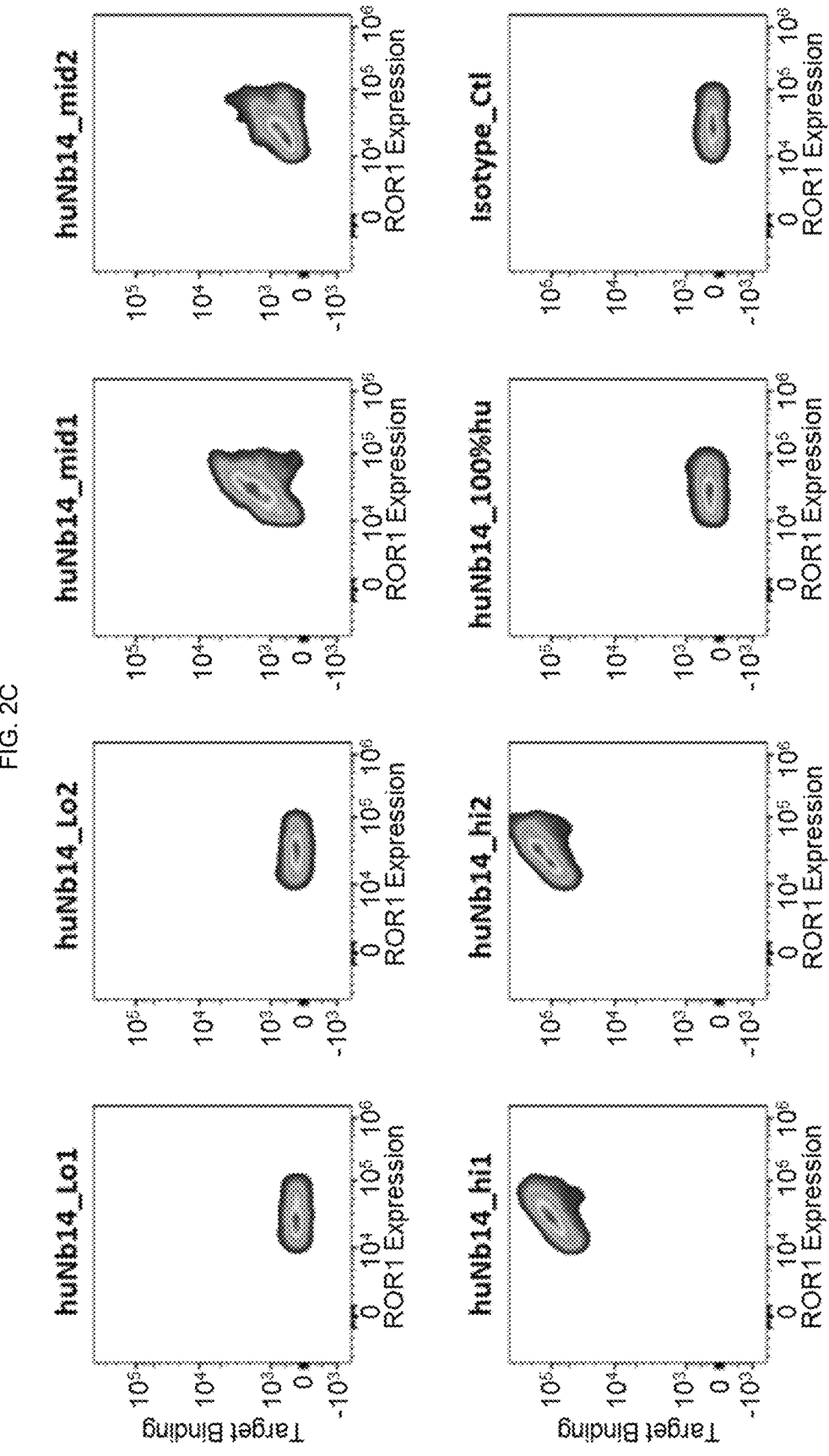
Figure 2D:
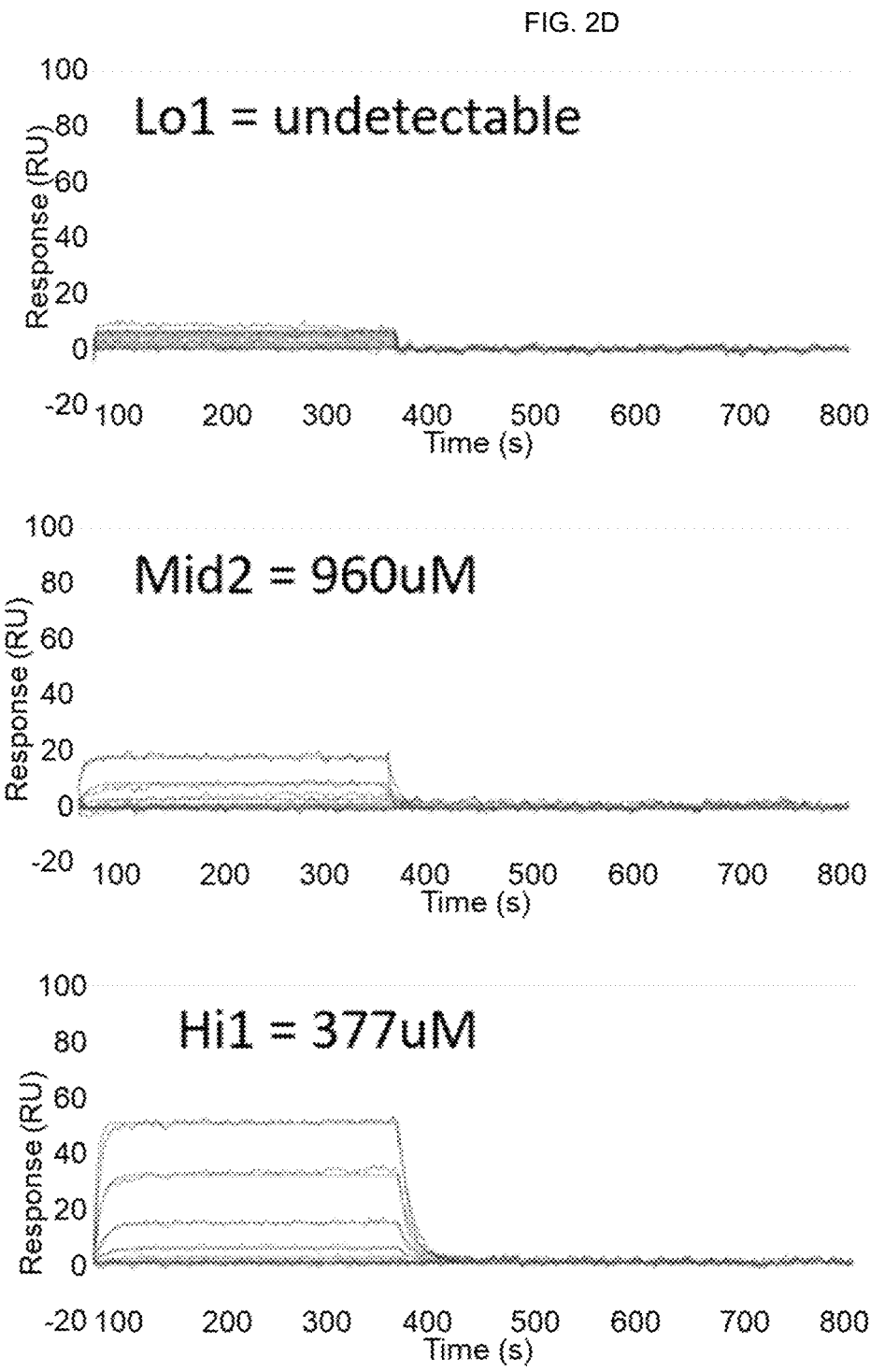
Figure 3:
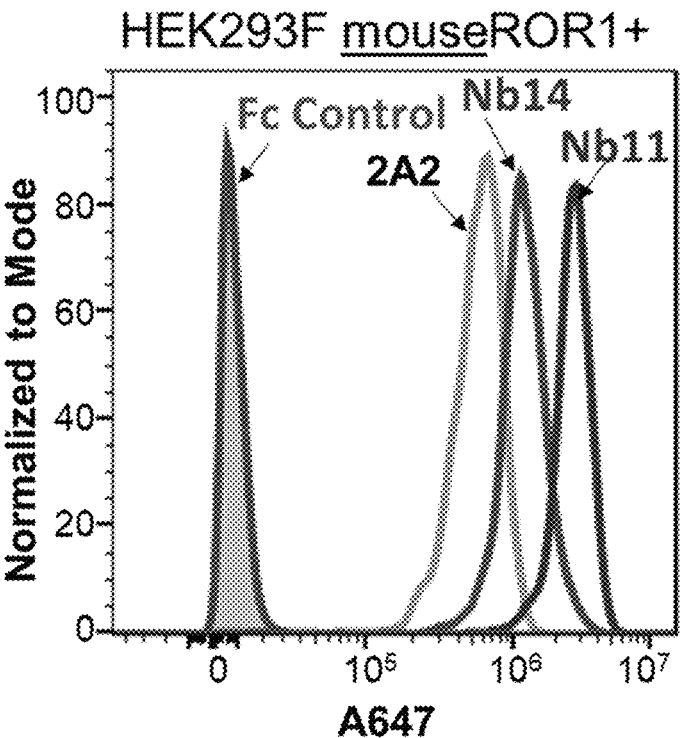
FIG. 3. Nb11 and Nb14 cross-react with mouse and cyno ROR1.
Figures 3, 4A:
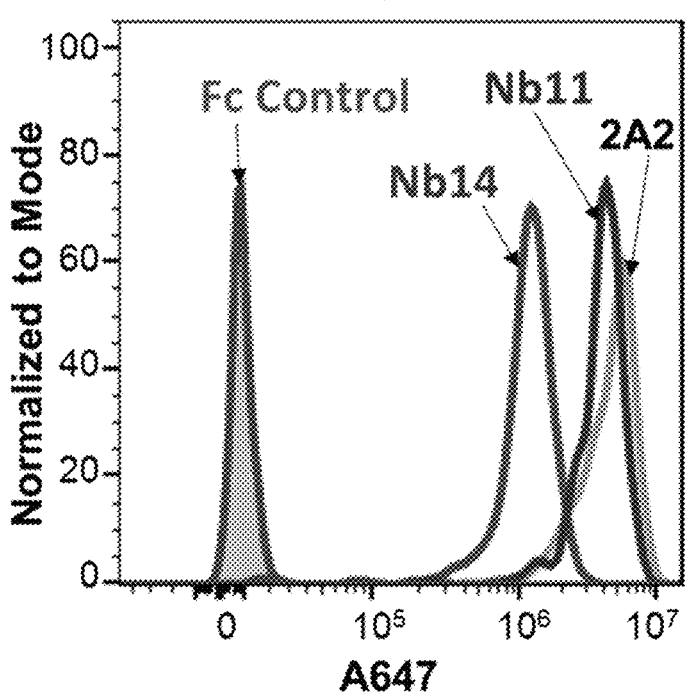
FIGS. 4A-4D. Nb11 and Nb14 target the ROR1 kringle domain. (4A) Schematic of ROR1 domains including Ig-like domain, Frizzled domain, Kringle domain, Tyrosine kinase domain, Ser/Thr-rich domains, and Proline-rich domain. (4B) Expression gel for Ig, FRZ, Nb-Fc, and Kringle. (4C) mAU as a function of retention time according to Superdex 200 SEC for the Nb11 complex, free Nb11, and the free Kringle fragment (top panel) as well as the Nb14 complex, free Nb14, and the free Kringle fragment (bottom panel). (4D) Expression gel for the Kringle fragment and Nb11 and Nb14 in reduced (R) and nonreduced (NR) forms.
Figure 4B:
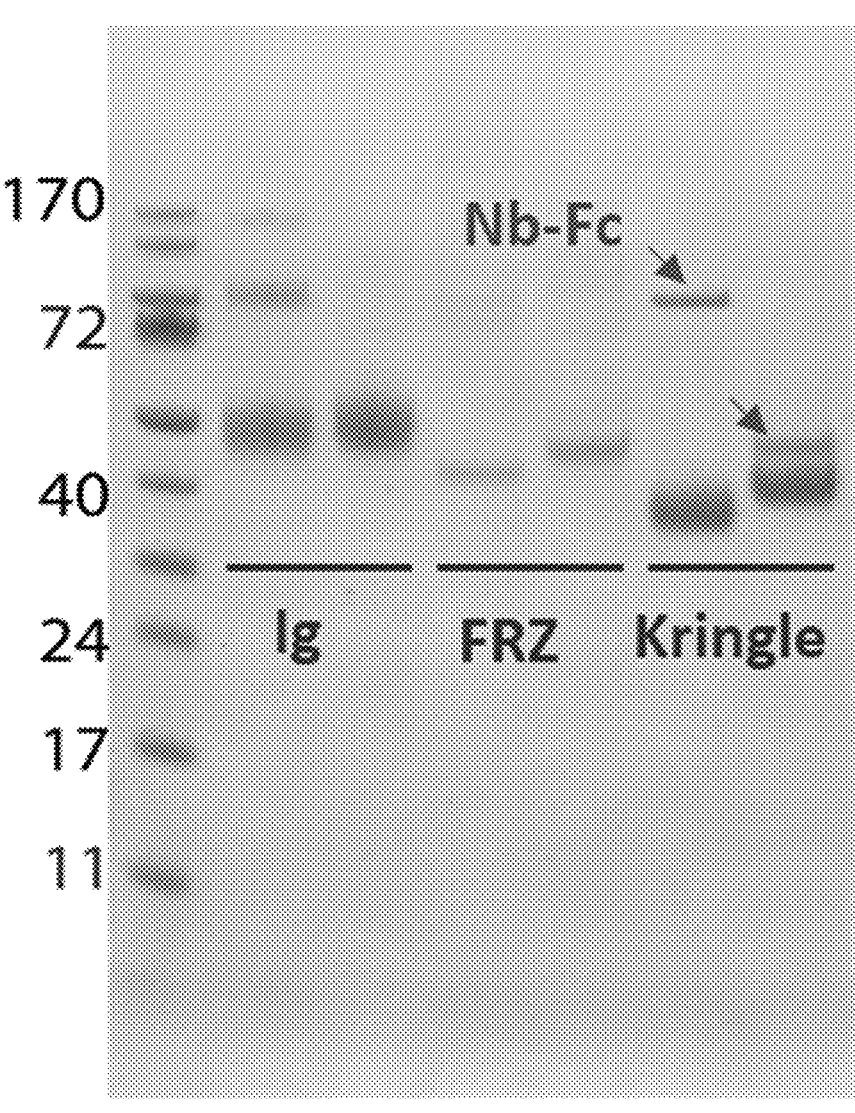
Figure 4C:
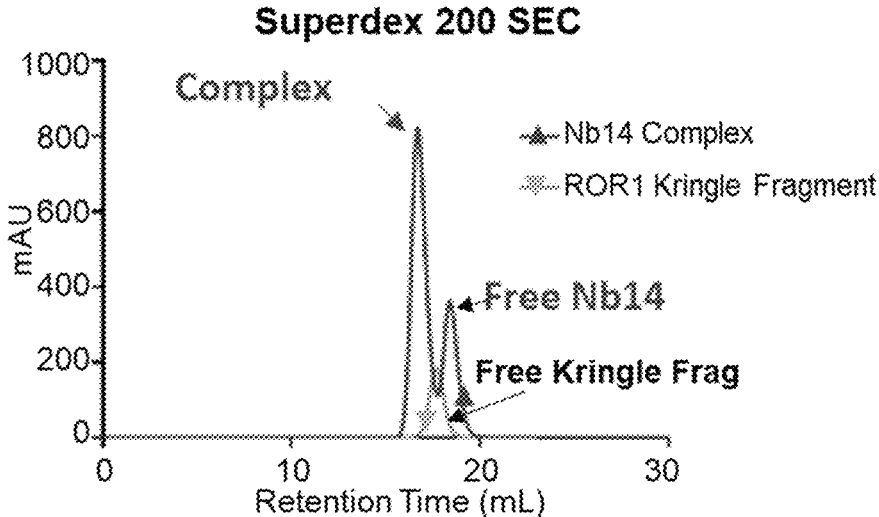
Figure 4D:
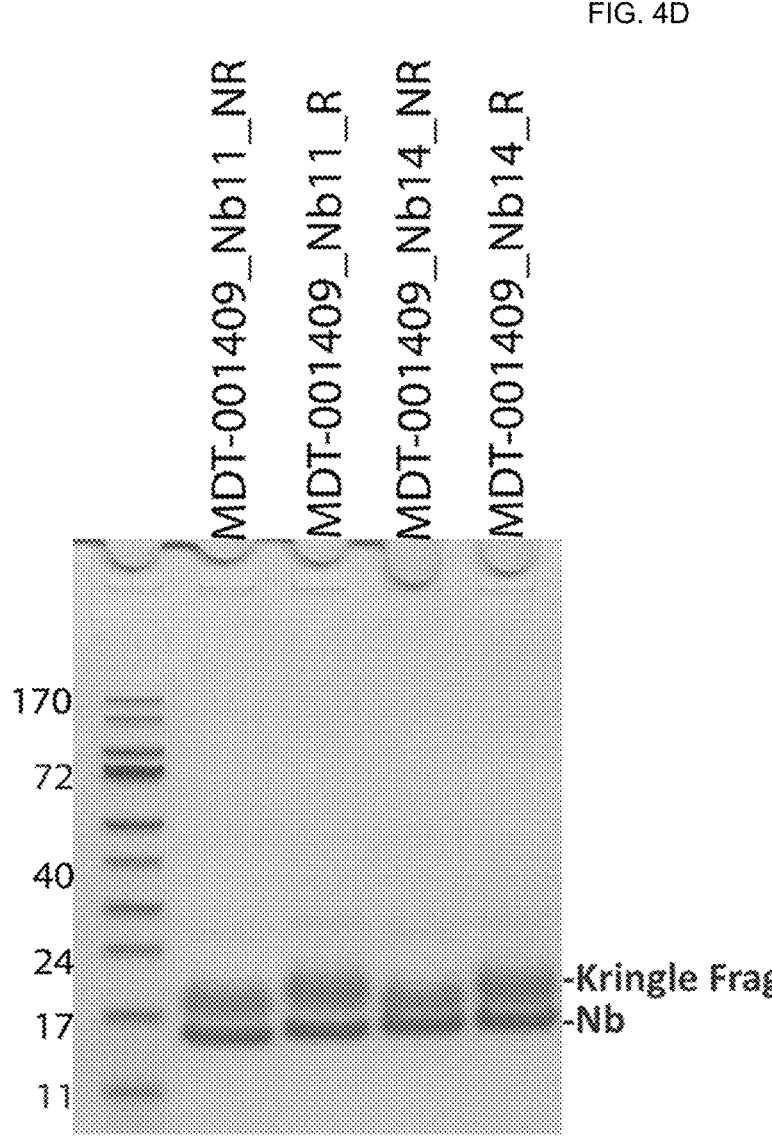
Figure 5A:
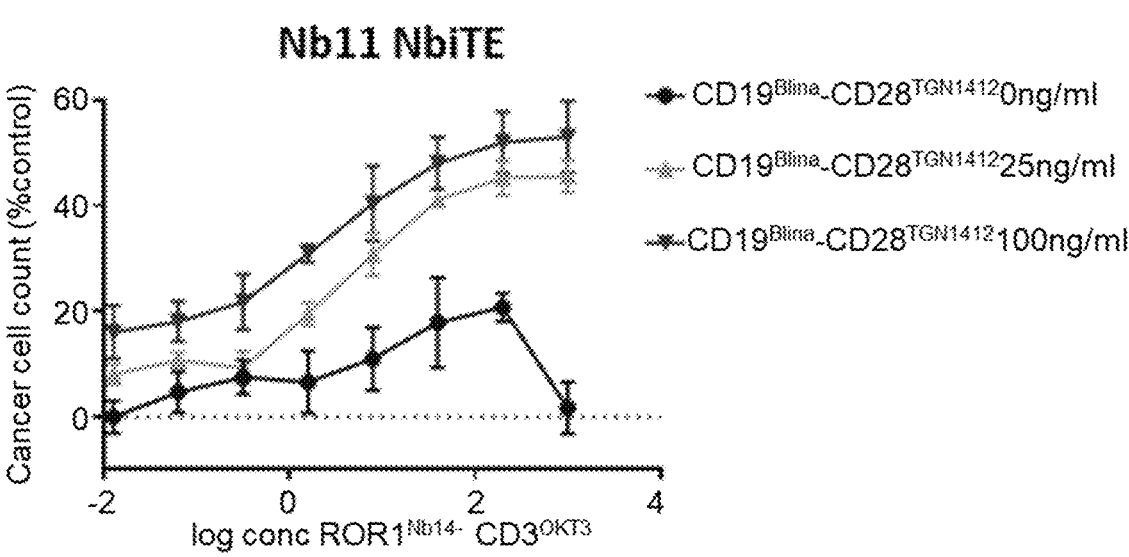
FIGS. 5A, 5B. Therapeutic Designs. (5A) Bispecific T cell engager format for Nb11 and Nb14 T-cell killing assay (48 hrs) compared to ROR1 targeted scFv (R12) bispecific T cell engager. (5B) Schematic depicting different formats of bispecific T cell engagers.
Figure 5A:
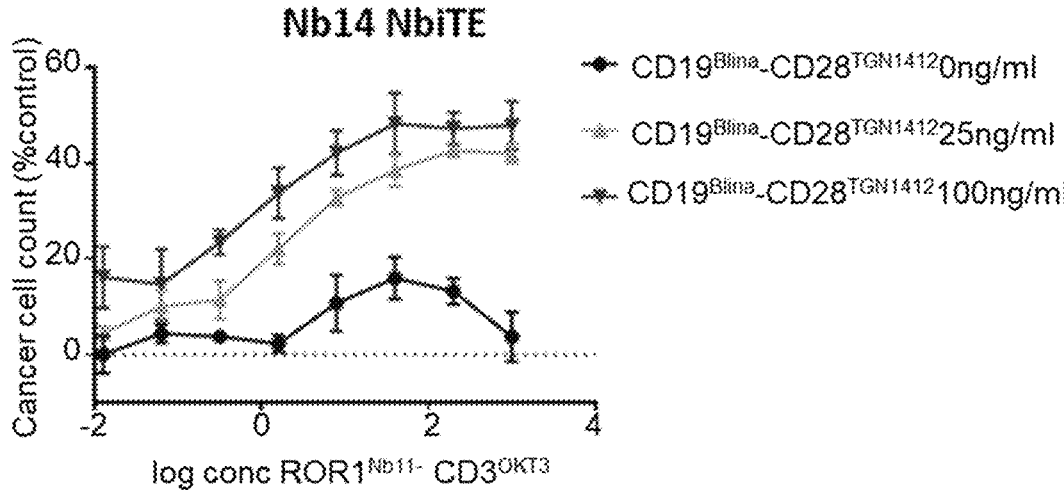
Figure 5A:
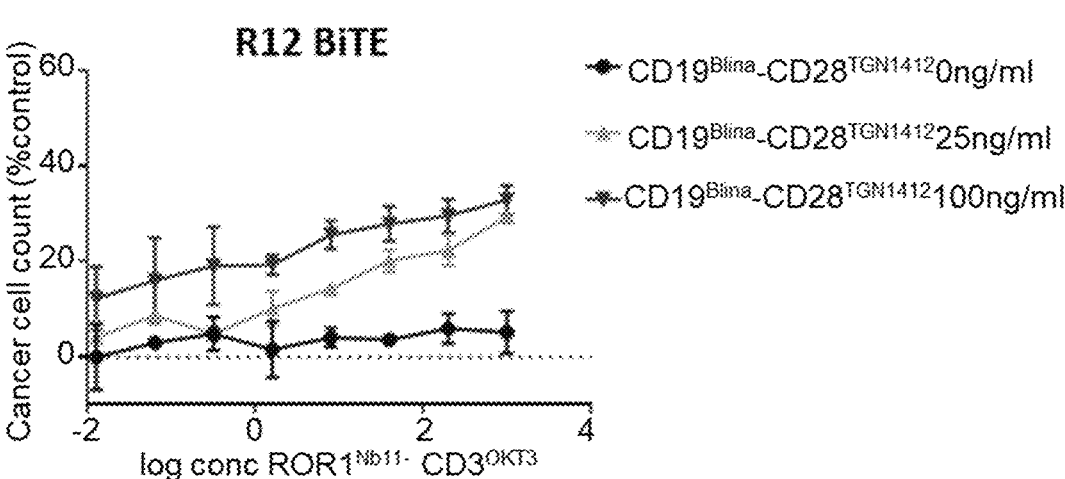
Figure 5B:
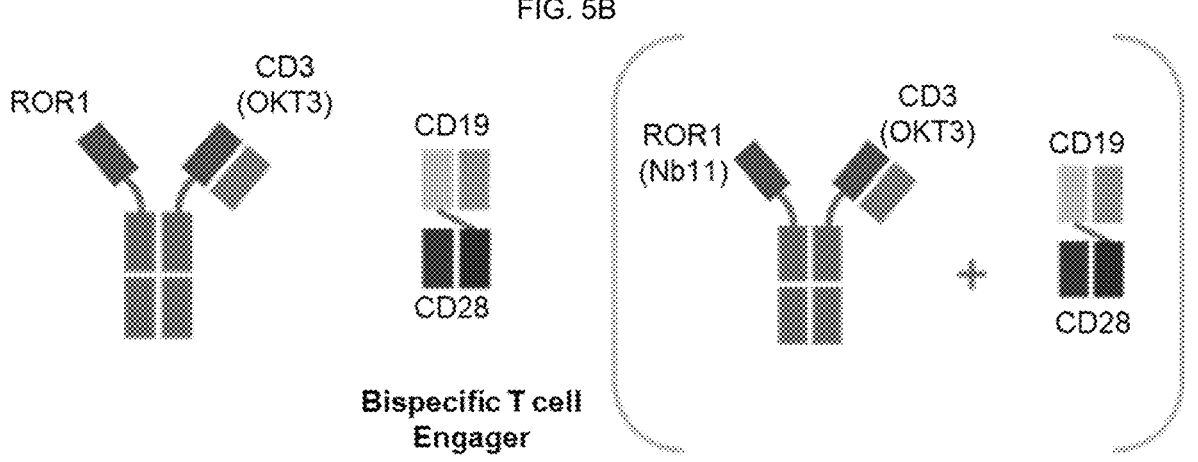
Figure 6:
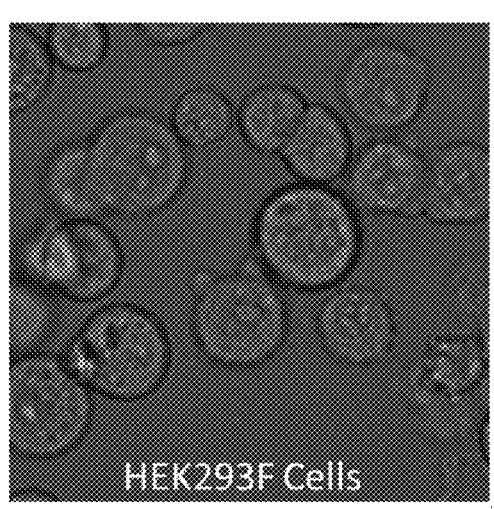
FIG. 6. Theranostics. Mixture of wildtype (WT) and ROR1-eGFP overexpressing HEK293F cells incubated and then washed with Nb14-streptavidin-A647 conjugates.
Figure 6:
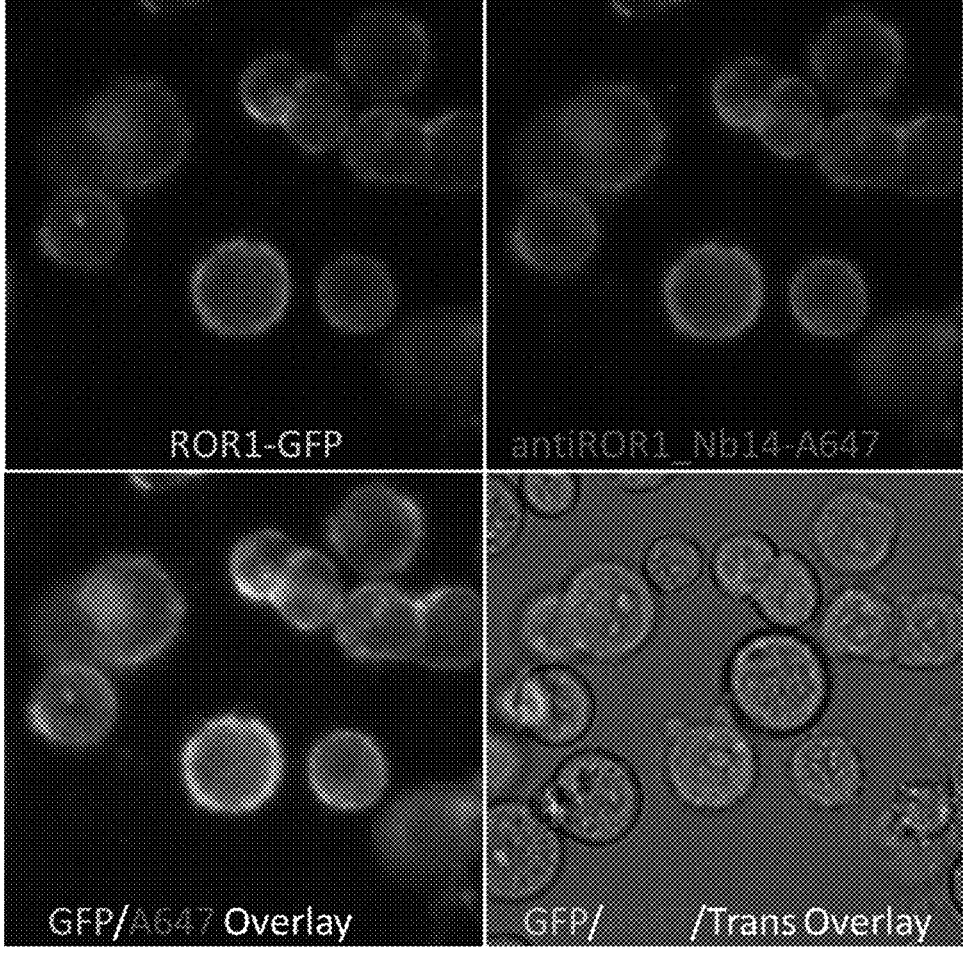

The current disclosure describes novel single-domain antibodies that bind receptor tyrosine kinase (ROR1). The single-domain antibodies can be used for multiple purposes including in research, imaging, diagnosis, and treatment of ROR1-related conditions. For example, these single-domain antibodies can be useful as cancer diagnostic/imaging agents and as anti-cancer therapeutics such as antibody drug conjugates and immune targeting reagents (e.g., multi-domain binding molecules or recombinant receptors).

In particular embodiments, a single-domain antibody that binds ROR1 includes Nb11 WT (SEQ ID NO: 1). In particular embodiments, a single-domain antibody that binds ROR1 includes Nb14 WT (SEQ ID NO: 2). In particular embodiments, a single-domain antibody that binds ROR1 includes huNb14 Lo1 (SEQ ID NO: 3). In particular embodiments, a single-domain antibody that binds ROR1 includes huNb14 Mid1 (SEQ ID NO: 4). In particular embodiments, a single-domain antibody that binds ROR1 includes huNb14 Hi2 (SEQ ID NO: 5). huNb14 Hi2 has higher binding affinity than huNb14 Mid1 which has higher binding affinity than huNb14 Lo1. The single-domain antibodies disclosed herein are not linked to an IgM Fc region or a multimerizing fragment thereof.

Aspects of the current disclosure are now described in more supporting detail as follows: (i) Conventional Human Antibodies & Associated Terminology; (ii) Single-Domain Antibodies; (iii) Heavy Chain Only Antibodies (HcAb); (iv) Multi-Domain Binding Molecules; (v) Antibody Conjugates; (vi) Recombinant Receptors; (vii) Compositions and Formulations; (viii) Methods of Use; (ix) Reference Levels Derived from Control Populations; (x) Kits; (xi) Exemplary Embodiments; and (xii) Closing Paragraphs. These headings are provided for organizational purposes only and do not limit the scope or interpretation of the disclosure.

(i) Conventional Human Antibodies & Associated Terminology. Unless otherwise indicated, a "conventional human antibody" includes a tetramer structure with two full-length heavy chains and two full-length light chains. The amino-terminal portion of each chain includes a variable region that is responsible for antigen recognition and epitope binding. The variable regions exhibit the same general structure of relatively conserved framework regions (FR) joined by three hyper variable regions, also called complementarity determining regions (CDRs). The CDRs from the two chains of each pair are aligned by the framework regions, which enables binding to a specific epitope. From N-terminal to C-terminal, both light and heavy chain variable regions include the domains FR1, CDR1, FR2, CDR2, FR3, CDR3 and FR4.

The assignment of amino acids to each domain can be in accordance with Kabat numbering (Kabat et al. (1991), "Sequences of Proteins of Immunological Interest," 5th Ed. Public Health Service, National Institutes of Health, Bethesda, Md. ("Kabat" numbering scheme)); Chothia (Al-Lazikani et al., (1997) JMB 273, 927-948 ("Chothia" numbering scheme)), Martin (Abinandan et al., *Mol Immunol.* 45:3832-3839 (2008), "Analysis and improvements to Kabat and structurally correct numbering of antibody variable domains"), Gelfand, Contact (MacCallum et al., J. Mol. Biol. 262:732-745 (1996), "Antibody-antigen interactions: Contact analysis and binding site topography," J. Mol. Biol. 262, 732-745." (Contact numbering scheme)), IMGT (Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme)), AHo (Honegger A and Plückthun A, "Yet another numbering scheme for immunoglobulin variable domains: an automatic modeling and analysis tool," J Mol Biol, 2001 Jun. 8; 309(3):657-70, (AHo numbering scheme)), North (North et al., *J Mol Biol.* 406(2):228-256 (2011), "A new clustering of antibody CDR loop conformations"), or other numbering schemes.

Definitive delineation of a CDR and identification of residues including the binding site of an antibody can be accomplished by solving the structure of the antibody and/or solving the structure of the antibody-epitope complex. In particular embodiments, this can be accomplished by methods such as X-ray crystallography and cryoelectron microscopy. Alternatively, CDRs are determined by comparison to known antibodies (linear sequence) and without resorting to solving a crystal structure. To determine residues involved in binding, a co-crystal structure of the Fab (antibody fragment) bound to the target can optionally be determined. Software programs, such as ABodyBuilder can also be used.

The carboxy-terminal portion of each chain defines a constant region (the Fc region), which is responsible for effector function of the antibody. Examples of effector functions include: Clq binding and complement dependent cytotoxicity (CDC); antibody-dependent cell-mediated cytotoxicity (ADCC); phagocytosis; down regulation of cell surface receptors (e.g., B-cell receptors); and B-cell activation. A portion of an Fc region is a fragment of an Fc region. The fragment can include 10% of an Fc region, 20% of an Fc region, 30% of an Fc region, 40% of an Fc region, 50% of an Fc region, 60% of an Fc region, 70% of an Fc region, 80% of an Fc region, 90% of an Fc region, or 95% of an Fc region. A portion of an Fc region can also include a characterized segment of an Fc region, such as a CH2 region or a CH3 region.

Within full-length light and heavy chains, the variable and constant regions are joined by a "J" region of amino acids, with the heavy chain also including a "D" region of amino acids. See, e.g., Fundamental Immunology, Ch. 7 (Paul, W., ed., 2nd ed. Raven Press, N.Y. (1989)).

Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, IgG1, IgG2, IgG3, and IgG4. IgM has subclasses including IgM1 and IgM2. IgA is similarly subdivided into subclasses including IgA1 and IgA2. IgG causes opsonization and cellular cytotoxicity and crosses the placenta, IgA functions on the mucosal surface, IgM is most effective in complement fixation, and IgE mediates degranulation of mast cells and basophils. The function of IgD is still not well understood. Resting B cells, which are immunocompetent but not yet activated, express IgM and IgD. Once activated and committed to secrete antibodies these B cells can express any of the five isotypes. The heavy chain isotypes of IgG, IgA, IgM, IgD and IgE are respectively designated the $\gamma$, $\alpha$, $\mu$, $\delta$, and $\epsilon$ chains.

Antibodies bind epitopes on antigens. The term antigen refers to a molecule or a portion of a molecule capable of being bound by an antibody. An epitope is a region of an antigen that is bound by the variable region of an antibody. Epitope determinants can include chemically active surface groupings of molecules such as amino acids, sugar side chains, phosphoryl or sulfonyl groups, and can have specific three-dimensional structural characteristics, and/or specific charge characteristics. When the antigen is a protein or peptide, the epitope includes specific amino acids within that protein or peptide that contact the variable region of an antibody.

In particular embodiments, an epitope denotes the binding site on the antigen (e.g., ROR1) bound by a corresponding variable region of an antibody. The variable region either binds to a linear epitope (e.g., an epitope including a stretch of 5 to 12 consecutive amino acids), or the variable region binds to a three-dimensional structure formed by the spatial arrangement of several short stretches of the protein target. Three-dimensional epitopes recognized by a variable region, e.g., by the epitope recognition site or paratope of an antibody or antibody fragment, can be thought of as three-dimensional surface features of an epitope molecule. These features fit precisely (in)to the corresponding binding site of the variable region and thereby binding between the variable region and its target protein (more generally, antigen) is facilitated. In particular embodiments, an epitope can be considered to have two levels: (i) the "covered patch" which can be thought of as the shadow an antibody variable region would cast on the antigen to which it binds; and (ii) the individual participating side chains and backbone residues that facilitate binding. Binding is then due to the aggregate of ionic interactions, hydrogen bonds, and hydrophobic interactions. For information regarding binding values and methods to measure the same, see the Closing Paragraphs section of this disclosure.

A monoclonal antibody refers to an antibody obtained from a population of substantially homogeneous antibodies, i.e., the individual antibodies including the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies and is not to be construed as requiring production of the antibody by any particular method. For example, monoclonal antibodies can be made by a variety of techniques, including the hybridoma method, recombinant DNA methods, phage-display methods, and methods utilizing transgenic animals containing all or part of the human immunoglobulin loci.

A "human antibody" is one which includes an amino acid sequence which corresponds to that of an antibody produced by a human or a human cell or derived from a non-human source that utilizes human antibody repertoires or other human antibody-encoding sequences.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. The subgroup of sequences can be a subgroup as in Kabat et al., Sequences of Proteins of Immunological Interest, Fifth Edition, NIH Publication 91-3242, Bethesda Md. (1991), vols. 1-3. In particular embodiments, for the $V_L$, the subgroup is subgroup kappa I as in Kabat et al. (supra). In particular embodiments, for the $V_H$, the subgroup is subgroup Ill as in Kabat et al. (supra).

A "humanized" antibody refers to a chimeric antibody including amino acid residues from non-human CDRs and amino acid residues from human FRs. In particular embodiments, a humanized antibody will include substantially all of at least one, and typically two, variable domains, in which all or substantially all of the CDRs correspond to those of a non-human antibody, and all or substantially all of the FRs correspond to those of a human antibody. A humanized antibody optionally may include at least a portion of an antibody constant region derived from a human antibody. A "humanized form" of an antibody, e.g., a non-human antibody, refers to an antibody that has undergone humanization.

Humanized antibodies and methods of making them are reviewed, e.g., in Almagro and Fransson, Front. Biosci. 13:1619-1633, 2008, and are further described, e.g., in Riechmann et al., Nature 332:323-329, 1988; Queen et al., Proc. Nat'l Acad. Sci. USA 86:10029-10033, 1989; U.S. Pat. Nos. 5,821,337, 7,527,791, 6,982,321, and 7,087,409; Kashmiri et al., Methods 36:25-34, 2005 (describing SDR (a-CDR) grafting); Padlan, Mol. Immunol. 28:489-498,1991 (describing "resurfacing"); Dall'Acqua et al., Methods 36:43-60,2005 (describing "FR shuffling"); and Osbourn et al., Methods 36:61-68, 2005 and Klimka et al., Br. J. Cancer, 83:252-260, 2000 (describing the "guided selection" approach to FR shuffling). EP-B-0239400 provides additional description of "CDR-grafting", in which one or more CDR sequences of a first antibody is/are placed within a framework of sequences not of that antibody, for instance of another antibody.

Human framework regions that may be used for humanization include: framework regions selected using the "best-fit" method (see, e.g., Sims et al. J. Immunol. 151:2296, 1993); framework regions derived from the consensus sequence of human antibodies of a particular subgroup of light or heavy chain variable regions (see, e.g., Carter et al., Proc. Nati. Acad. Sci. USA, 89:4285, 1992; and Presta et al., J. Immunol., 151:2623, 1993); human mature (somatically mutated) framework regions or human germline framework regions (see, e.g., Almagro and Fransson, Front. Biosci. 13:1619-1633, 2008); and framework regions derived from screening FR libraries (see, e.g., Baca et al., J. Biol. Chem. 272:10678-10684, 1997; and Rosok et al., J. Biol. Chem. 271:22611-22618, 1996).

(ii) Single-Domain Antibodies. In particular embodiments, single-domain antibodies are the antigen binding fragment of heavy chain only antibodies. Single-domain antibodies are also referred to as VHH antibodies or nanobodies. One of ordinary skill in the art will recognize portions of the discussion related to "conventional human antibodies" that equally apply to single-domain antibodies, and those portions that only apply to conventional human antibodies (e.g., discussion of light chains, which has relevance to examples of various multi-domain binding molecules described herein). Single-domain antibodies are often more stable than scFv and Fab constructs and are more easily introduced into alternative scaffolds as they do not require heavy light chain pairings and long linker sequences.

In particular embodiments, a single-domain antibody that binds ROR1 is Nb11 WT. In particular embodiments, Nb11 WT includes the sequence:

(SEQ ID NO: 1)
METDTLLLWVLLLWVPGSTGQVKLVQSGGGLVQAGGSLRLSCAASGSIFS

SASMGWYRQAPGKPREQVASITRDGNTYYEDDVKGRFTISRDNARSTGYL

QMNSLTPEDTGVYYCNVYQLGFYDKWGQGTQVIVSS.

In particular embodiments, a single-domain antibody that binds ROR1 is Nb14 WT. In particular embodiments, Nb14 WT includes the sequence:

(SEQ ID NO: 2)
METDTLLLWVLLLWVPGSTGQVKLVQSGGGLVQTGGSLRLSCAASEITFD

MYSMGWYREAPGKARDAVASITNRGNTYYADSVKGRFTISRDNAKKTMYL

QMNSLKPEDTAVYYCNVYRTGFSDYWGQGTQVTVSS.

In particular embodiments, a single-domain antibody that binds ROR1 is huNb14 Lo1. In particular embodiments, huNb14 Lo1 includes the sequence:

(SEQ ID NO: 3)
METDTLLLWVLLLWVPGSTGQVQLVQSGGGLVQPGGSLRLSCAASGITFD

MYSMGWYREAPGKGLEAVASITNRGNTYYADSVKGRFTISRDNAKNTLYL

QMNSLRAEDTAVYYCAVYRTGFSDYWGQGTLVTVSS.

In particular embodiments, a single-domain antibody that binds ROR1 is huNb14 Mid1. In particular embodiments, huNb14 Mid1 includes the sequence:

(SEQ ID NO: 4)
METDTLLLWVLLLWVPGSTGQVQLVQSGGGLVQTGGSLRLSCAASGITFD

MYSMGWFRQAPGKGLDAVASITNRGNTYYADSVKGRFTISRDNAKNTLYL

QMNSLRAEDTAVYYCNVYRTGFSDYWGQGTLVTVSS.

In particular embodiments, a single-domain antibody that binds ROR1 is huNb14 Hi2. In particular embodiments, huNb14 Hi2 includes the sequence:

(SEQ ID NO: 5)
METDTLLLWVLLLWVPGSTGQVKLVQSGGGLVQTGGSLRLSCAASGITFD

MYSMGWYRQAPGKGLEAVASITNRGNTYYADSVKGRFTISRDNAKNTLYL

QMNSLRPEDTAVYYCNVYRTGFSDYWGQGTLVTVSS.

Referring to single-domain antibodies disclosed herein, the following CDR sets are provided:

TABLE 1

CDRs of single-domain antibodies.

| Antibody Name | CDR Definition | CDR | Sequence | SEQ ID NO: |
|---|---|---|---|---|
| Nb11 WT | IMGT | CDR1 | GSIFSSAS | 6 |
| | | CDR2 | ITRDGNT | 7 |
| | | CDR3 | NVYQLGFYDK | 8 |
| | Kabat | CDR1 | SASMG | 9 |
| | | CDR2 | SITRDGNTYYEDDVKG | 10 |
| | | CDR3 | YQLGFYDK | 11 |
| | Chothia | CDR1 | GSIFSSA | 12 |
| | | CDR2 | TRDGN | 13 |
| | | CDR3 | YQLGFYDK | 11 |
| | North | CDR1 | AASGSIFSSASMG | 14 |
| | | CDR2 | SITRDGNTY | 15 |
| | | CDR3 | NVYQLGFYDK | 8 |
| | Contact | CDR1 | SSASMG | 16 |
| | | CDR2 | QVASITRDGNTY | 17 |
| | | CDR3 | NVYQLGFYD | 18 |
| Nb14 WT | IMGT | CDR1 | EITFDMYS | 19 |
| | | CDR2 | ITNRGNT | 20 |
| | | CDR3 | NVYRTGFSDY | 21 |
| | Kabat | CDR1 | MYSMG | 22 |
| | | CDR2 | SITNRGNTYYADSVKG | 23 |
| | | CDR3 | YRTGFSDY | 24 |
| | Chothia | CDR1 | EITFDMY | 25 |
| | | CDR2 | TNRGN | 26 |
| | | CDR3 | YRTGFSDY | 24 |
| | North | CDR1 | AASEITFDMYSMG | 27 |
| | | CDR2 | SITNRGNTY | 28 |
| | | CDR3 | NVYRTGFSDY | 21 |
| | Contact | CDR1 | DMYSMG | 29 |
| | | CDR2 | AVASITNRGNTY | 30 |
| | | CDR3 | NVYRTGFSD | 31 |
| huNb14 Lo1 | IMGT | CDR1 | GITFDMYS | 32 |
| | | CDR2 | ITNRGNT | 20 |
| | | CDR3 | AVYRTGFSDY | 33 |

TABLE 1-continued

CDRs of single-domain antibodies.

| Antibody Name | CDR Definition | CDR | Sequence | SEQ ID NO: |
|---|---|---|---|---|
| | Kabat | CDR1 | DMYSM | 34 |
| | | CDR2 | SITNRGNTYYADSVKG | 23 |
| | | CDR3 | YRTGFSDY | 24 |
| | Chothia | CDR1 | GITFDMY | 35 |
| | | CDR2 | TNRGN | 26 |
| | | CDR3 | AVYRTGFSDY | 33 |
| | North | CDR1 | AASGITFDMYSMG | 36 |
| | | CDR2 | SITNRGNTY | 28 |
| | | CDR3 | AVYRTGFSDY | 33 |
| | Contact | CDR1 | DMYSMG | 29 |
| | | CDR2 | AVASITNRGNTY | 30 |
| | | CDR3 | AVYRTGFSD | 37 |
| huNb14 Mid1 | IMGT | CDR1 | GITFDMYS | 32 |
| | | CDR2 | ITNRGNT | 20 |
| | | CDR3 | NVYRTGFSDY | 21 |
| | Kabat | CDR1 | DMYSM | 34 |
| | | CDR2 | SITNRGNTYYADSVKG | 23 |
| | | CDR3 | YRTGFSDY | 24 |
| | Chothia | CDR1 | GITFDMY | 35 |
| | | CDR2 | TNRGN | 26 |
| | | CDR3 | YRTGFSDY | 24 |
| | North | CDR1 | AASGITFDMYSMG | 36 |
| | | CDR2 | SITNRGNTY | 28 |
| | | CDR3 | NVYRTGFSDY | 21 |
| | Contact | CDR1 | DMYSMG | 29 |
| | | CDR2 | AVASITNRGNTY | 30 |
| | | CDR3 | NVYRTGFSD | 31 |
| huNb14 Hi2 | IMGT | CDR1 | GITFDMYS | 32 |
| | | CDR2 | ITNRGNT | 20 |
| | | CDR3 | NVYRTGFSDY | 21 |
| | Kabat | CDR1 | DMYSM | 34 |
| | | CDR2 | SITNRGNTYYADSVKG | 23 |
| | | CDR3 | YRTGFSDY | 24 |
| | Chothia | CDR1 | GITFDMY | 35 |
| | | CDR2 | TNRGN | 26 |
| | | CDR3 | YRTGFSDY | 24 |

TABLE 1-continued

CDRs of single-domain antibodies.

| Antibody Name | CDR Definition | CDR | Sequence | SEQ ID NO: |
|---|---|---|---|---|
| | North | CDR1 | AASGITFDMYSMG | 36 |
| | | CDR2 | SITNRGNTY | 28 |
| | | CDR3 | NVYRTGFSDY | 21 |
| | Contact | CDR1 | DMYSMG | 29 |
| | | CDR2 | AVASITNRGNTY | 30 |
| | | CDR3 | NVYRTGFSD | 31 |

In certain examples, single-domain antibodies are used in their single-domain form, as provided in the sequences above (including functional variants).

(iii) Heavy Chain Only Antibodies (HcAb). When linked to a non-IgM Fc fragment, a single-domain antibody disclosed herein can be referred to as a heavy chain only antibody (HcAb). Certain examples of HcAb include single-domain antibodies linked to a human Fc region selected from IgG, IgA, IgD and IgE. In particular embodiments, the single-domain antibodies include anti-ROR1 single-domain antibodies. In particular embodiments, the single-domain antibodies include Nb11 WT, Nb14 WT, huNb14 Lo1, huNb14 Mid1, or huNb14 Hi2.

As one example, the Fc portion of human IgG1 includes the sequence:

```
                                    (SEQ ID NO: 38)
THTCPPCPAPEFFGGPSVFFFPPKPKDTFMISRTPEVTCVVVDVSHEDPE

VKFNWYVDGVEVHNAKTKPREEQYNSTYRVVSVETVFHQDWENGKEYKCK

VSNKAFPVPIEKTISKAKGQPREPQVYTLPPSREEMTKNQVSLTCLVKGF

YPSDIAVEWESNGQPENNYKTTPPVLDSDGPFFLYSKLTVDKSRWQQGNV

FSCSVMHEALHNHYTQKSLSLSPGK.
```

The human IgG2 Fc region includes the amino acid sequence: PAPPVAGPSVFLFPPKPKDTLMISRTPE-VTCVVVDVSHEDPE-VQFNWYVDGVEVHNAKTKPRE EQFN-STFRVVSVLTVVHQDWLNGKEYKCKVSNK GLPAPIEKTISKTKGQPREPQVYTLPPSRE EMT-KNQVSLTCLVKGFYPSDIAVEWESNGQPEN-NYKTTPPMLDSDGSFFLYSKLTVDKSRWQ QGNVFSCSVMHEALHNHYTQKSLSLSPGK (SEQ ID NO: 39) Referring to SEQ ID NO: 39, the human CH2 region extends from amino acid 10 to amino acid 107 and the human CH3 region extends from amino acid 116 to amino acid 212.

The human IgG3 Fc region includes the amino acid sequence: PAPELLGGPSVFLFPPKPKDTLMISRTPE-VTCVVVDVSHEDPEVQFKWYVDGVEVHNAKTKPR EEQFNSTFRVVSVLTVLHQDWLNGKEYKCKVSNKA-LPAPIEKTISKTKGQPREPQVYTLPPSRE EMT-KNQVSLTCLVKGFYPSDIAVEWESSGQPENNYN-TTPPMLDSDGSFFLYSKLTVDKSRWQ QGNIFSCSVMHEALHNRFTQKSLSLSPGK (SEQ ID NO: 40). Referring to SEQ ID NO: 40, the human CH2 region extends from amino acid 11 to amino acid 108 and the human CH3 region extends from amino acid 117 to amino acid 212.

The human IgG4 Fc region includes the amino acid sequence: PAPEFLGGPSVFLFPPKPKDTLMISRTPE-VTCVVVDVSQEDPEVQFNWYVDGVEVHNAKTKPR EEQFNSTYRVVSVLTVLHQDWLN GKEYKCKVSNKGLPSSIEKTISKAKGQPREPQVYT LPPSQ EEMTKNQVSLTCLVKGFYPSDIAVEWESNGQ-PENNYKTTPPVLDSDGSFFLYSRLTVDKSRW QEGNVFSCSVMHEALHNHYTQKSLSLSLGK (SEQ ID NO: 41). Referring to SEQ ID NO: 41, the human CH2 region extends from amino acid 1 to amino acid 111 and the human CH3 region extends from amino acid 112 to amino acid 218.

Particular embodiments include immunoglobulin constant region domains that allow the binding portion of molecules provided herein to readily multimerize into dimers. Basic immunoglobulin structures in vertebrate systems are described above and well understood. (See, e.g., Harlow et al., Antibodies: A Laboratory Manual, Cold Spring Harbor Laboratory Press, 2nd ed. 1988).

IgA antibodies, have emerged as promising drug candidates in the fields of, e.g., immuno-oncology and infectious diseases allowing for improved specificity, improved avidity, and the ability to bind to multiple binding targets. See, e.g., U.S. Pat. Nos. 9,951,134, 10,400,038, and 9,938,347, U.S. Patent Application Publication Nos. US20190100597A1, US20180118814A1, US20180118816A1, US20190185570A1, and US20180265596A1, and PCT Publication Nos. WO 2018/017888, WO 2018/017763, WO 2018/017889, WO 2018/017761, and WO 2019/165340.

Immunoglobulin A (IgA), as the major class of antibody present in the mucosal secretions of most mammals, represents a key first line of defense against invasion by inhaled and ingested pathogens. IgA is also found at significant concentrations in the serum of many species, where it functions as a second line of defense mediating elimination of pathogens that have breached the mucosal surface. Receptors specific for the Fc region of IgA, FcaR, are key mediators of IgA effector function. Native IgA is a tetrameric protein including two identical light chains (K or A) and two identical heavy chains. IgA, similarly to IgG, contains three constant domains (CA1-CA3), with a hinge region between the CA1 and CA2 domains. The main difference between IgA1 and IgA2 resides in the hinge region that lies between the two Fab arms and the Fc region. IgA1 has an extended hinge region due to the insertion of a duplicated stretch of amino acids, which is absent in IgA2. Both forms of IgA have the capacity to form dimers, in which two monomer units, are arranged in an end-to-end configuration stabilized by disulfide bridges and incorporation of a J-chain.

IgAs possess an 18-amino acid extension in the C terminus called the "tail-piece" (tp). The IgA tp is highly conserved among various animal species. The conserved penultimate cysteine residue in the IgA tp has been demonstrated to be involved in multimerization by forming a disulfide bond between heavy chains to permit formation of a multimer. The tp contain an N-linked carbohydrate addition site, the presence of which is required for dimer formation in IgA.

The human IgA1 constant region typically includes the amino acid sequence: ASPTSPKVFPLSLCSTQPDGNV-VIACLVQGFFPQEPLSVTWSESGQGVTARNFPPSQ-DASGDL YTTSSQLTLPATQCLAGKSVTCHVKHYTNP- SQDVTVPCPVPSTPPTPSPSTPPTPSPSCCHPR LSLHRPALEDLLLGSEANLTCTLTGLR-DASGVTFTWTPSSGKSAVQGPPERDLCGCYSVSSVL PGCAEPWNHGKTFTCTAAYPESKTPLTATL-SKSGNTFRPEVHLLPPPSEELALNELVTLTCLAR GFSPKDVLVRWLQGSQELPREKYLTWASRQEP-SQGTTTFAVTSILRVAAEDWKKGDTFSCMV GHEAL-PLAFTQKTIDRLAGKPTHVNVSVVMAEVDGTCY (SEQ ID NO: 42). Referring to this SEQ ID NO: 42, the human CA1 domain extends from amino acid 6 to amino acid 98; the human IgA1 hinge region extends from amino acid 102 to amino acid 124, the human CA2 domain extends from amino acid 125 to amino acid 219, the human CA3 domain extends from amino acid 228 to amino acid 330, and the tp extends from amino acid 331 to amino acid 352.

The human IgA2 constant region typically includes the amino acid sequence ASPTSPKVFPLSLDSTPQDGNVV-VACLVQGFFPQEPLSVTWSESGQNVTARNFPPSQ-DASGD LYTTSSQLTLPATQCPDGKSVTCHVKHYTNP-SQDVTVPCPVPPPPPCCHPRLSLHRPALEDLL LGSEANLTCTLTGLRDASGATFTWTPSSGKSAVQGP-PERDLCGCYSVSSVLPGCAQPWNHG ETFTCTAAHPELKTPLTANITKSGNTFRPEVHLLPPP-SEELALNELVTLTCLARGFSPKDVLVRW LQGSQEL-PREKYLTWASRQEPSQGTTTFAVTSILRVAAE-DWKKGDTFSCMVGHEALPLAFTQK TIDRLAGKPTHVNVSVVMAEVDGTCY (SEQ ID NO: 43). Referring to this SEQ ID NO: 43, the human CA1 domain extends from amino acid 6 to amino acid 98, the human IgA2 hinge region extends from amino acid 102 to amino acid 111, the human CA2 domain extends from amino acid 113 to amino acid 206, the human CA3 domain extends from amino acid 215 to amino acid 317, and the tp extends from amino acid 318 to amino acid 340.

As indicated, two IgA binding units can form a complex with two additional polypeptide chains, the J chain (e.g., SEQ ID NO: 46, the mature human J chain) and the secretory component to form a bivalent secretory IgA (sIgA)-derived binding molecule. An exemplary precursor secretory component includes the sequence: MLLFVLTCL-LAVFPAISTKSPIFGPEEVNSVEGNSVSIT-CYYPPTSVNRHTRKYWCRQGARGGC ITLISS-EGYVSSKYAGRANLTNFPENGTFV VNIAQLSQDDSGRYKCGLGINSRGLSFDVSLEVS QGPGLLNDTKVYTVDLGRTVTINCPFK-TENAQKRKSLYKQIGLYPVLVIDSSGYVNPNYT-GRIRL DIQGTGQLLFSVVINQLRLSDAGQYL-CQAGDDSNSNKKNADLQVLKPEPEL VYEDLRGSVTFH CALGPEVANVAKFLCRQSS-GENCDVVVNTLGKRAPAFEGRILLNPQDKDGSFSV-VITGLRKED AGRYLCGAHSDGQLQEGSPIQAWQL FVNEESTIPRSPTVVKGVAGGSVAVLCPYNRKESKSIK YWCLWEGAQNGRCPLLVD-SEGWVKAQYEGRLSLLEEPGNGTFTVILNQLT-SRDAGFYWCLTN GDTLWRTTVEIKIIEGEPNLKVPGN VTAVLGETLKVPCHFPCKFSSYEKYWCK-WNNTGCQALP SQDEGPSKAFVNCDEN-SRLVSLTLNLVTRADEGWYWCGVKQGHFY-GETAAVYVAVEERKAA GSRDVSLAKADAAPDEKVLDSGFREIENKAIQDPRL-FAEEKAVADTRDQADGSRASVDSGSSE EQGGSSRALVSTLVPLGLVLAVGAVAVGVARAR-HRKNVDRVSIRSYRTDISMSDFENSREFGA NDNM-GASSITQETSLGGKEEFVATTESTTETKEPKKAKRSS-KEEAEMAYKDFLLQSSTVAAEA QDGPQEA (SEQ ID NO: 44). An exemplary mature secretory component includes KSPIFGPEEVNSVEGNSVSIT-
CYYPPTSVNRHTRKYWCRQGARGGCITLISS-
EGYVSSKYAGR ANLTNFPENGTFVVNIAQLSQDDS-
GRYKCGLGINSRGLSFDVSLEVSQGP
GLLNDTKVYTVDL GRTVTINCPFK-
TENAQKRKSLYKQIGLYPVLVIDSSGYVNPNYT-
GRIRLDIQGTGQLLFSVVINQL RLSDAGQYL-
CQAGDDSNSNKKNADLQVLKP
EPELVYEDLRGSVTFHCALGPEVANVAKFLCR QSS-
GENCDVVVNTLGKRAPAFEGRILLNPQDKDGSFSV-
VITGLRKEDAGRYLCGAHSDGQLQE
GSPIQAWQLFVNEESTIPRSPTVVKGVAGGSVA-
VLCPYNRKESKSIKYWCLWEGAQNGRCPLL
VDSEGWVKAQYEGRLSLLEEPGNGTFTVILNQLT-
SRDAGFYWCLTNGDTLWRTTVEIKIIEGEP
NLKVPGNVTAVLGETLKVPCHFPCKFSSYEKYWCK-
WNNTGCQALPSQDEGPSKAFVNCDEN
SRLVSLTLNLVTRADEGWYWCGVKQGHFY-
GETAAVYVAVEERKAAGSRDVSLAKADAAPDEK
VLDSGFREIENKAIQDPR (SEQ ID NO: 45). The assem-
bly of two IgA binding units into a dimeric IgA-derived
binding molecule is thought to involve the CA3 and tp
domains. See, e.g., Braathen, R., el al., J. Biol. Chem.
277:42755-42762 (2002). Accordingly, a multimerizing
dimeric IgA-derived binding molecule provided in this
disclosure typically includes IgA constant regions that
include at least the CA3 and tp domains.

An engineered IgA heavy chain constant region can
additionally include a CA2 domain or a fragment thereof, an
IgA hinge region or fragment thereof, a CA1 domain or a
fragment thereof, and/or other IgA (or other immunoglobu-
lin, e.g., IgG) heavy chain domains, including, e.g., an IgG
hinge region. In certain embodiments, a binding molecule as
provided herein can include a complete IgA heavy chain
constant domain (e.g., SEQ ID NO: 42 or SEQ ID NO: 43),
or a variant, derivative, or analog thereof.

In particular embodiments, the IgA heavy chain constant
regions can include amino acids 125 to 353 of SEQ ID NO:
42 or amino acids 113 to 340 of SEQ ID NO: 43. In
particular embodiments, the IgA heavy chain constant
regions can each further include an IgA or IgG hinge region
situated N-terminal to the IgA CA2 domains. For example,
the IgA heavy chain constant regions can include amino
acids 102 to 353 of SEQ ID NO: 42 or amino acids 102 to
340 of SEQ ID NO: 43. In particular embodiments, the IgA
heavy chain constant regions can each further include an
IgA CA1 domain situated N-terminal to the IgA hinge
region.

Each of the strategies discussed above can be used to
create IgA antibody-based dimers.

The mature human J-chain includes the amino acid
sequence:

(SEQ ID NO: 46)
QEDERIVLVDNKCKCARITSRIIRSSEDPNEDIVERNIRIIVPLNNRENI

SDPTSPLRTRFVYHLSDLCKKCDPTEVELDNQIVTATQSNICDEDSATET

CYTYDRNKCYTAVVPLVYGGETKMVETALTPDACYPD.

The term "J-chain" as used herein refers to the J-chain of
native sequence IgA antibodies of any animal species. When
specified, it can also refer to any functional fragment
thereof, derivative thereof, and/or variant thereof, including
a mature human J-chain amino acid sequence provided
herein as SEQ ID NO: 46. A functional fragment, derivative, and/or variant of a J-chain has at least 90% sequence identity
to the reference J-chain and retains the multimerizing func-
tion of the reference J-chain.

Particular embodiments include a heterologous polypep-
tide (e.g., a single-domain antibody binding domain) fused
to the J-chain or functional fragment thereof via a peptide
linker, e.g., a peptide linker including at least 5 amino acids,
but no more than 25 amino acids. In certain aspects, the
peptide linker includes (GGGGS)n (SEQ ID NO: 47)
wherein n is 1-5.

A single-domain antibody binding domain can be intro-
duced into the J-chain at any location that allows the binding
of the binding domain to its binding target without interfer-
ing with J-chain function or the function of an associated
IgA or hybrid IgG antibody. Insertion locations include at or
near the C-terminus, at or near the N-terminus or at an
internal location that, based on the three-dimensional struc-
ture of the J-chain, is accessible. In certain aspects, the
antigen-binding domain can be introduced into the mature
human J-chain of SEQ ID NO: 46 between cysteine residues
92 and 101 of SEQ ID NO: 46. In a further aspect, the
antigen-binding domain can be introduced into the human
J-chain of SEQ ID NO: 46 at or near a glycosylation site. In
a further aspect, the antigen-binding domain can be intro-
duced into the human J-chain of SEQ ID NO: 46 within 10
amino acid residues from the C-terminus, or within 10
amino acids from the N-terminus.

In particular embodiments, the single-domain antibody is
introduced into the native human J-chain sequence of SEQ
ID NO: 46 by chemical or chemo-enzymatic derivatization.
In particular embodiments, the single-domain antibody is
introduced into the native human J-chain sequence of SEQ
ID NO: 46 by a chemical linker. In some embodiments, the
chemical linker is a cleavable or non-cleavable linker. In
particular embodiments, the cleavable linker is a chemically
labile linker or an enzyme-labile linker. In some embodi-
ments, the linker is selected from the group including
N-succinimidyl-3-(2-pyridyldithio) propionate (SPDP), suc-
cinimidyl-4-(N-maleimidomethyl) cyclohexane-1-carboxy-
late (SMCC), N-succinimidyl-4-(2-pyridylthio) pentanoate
(SPP), iminothiolane (IT), afunctional derivatives of imi-
doesters, active esters, aldehydes, bis-azido compounds,
bis-diazonium derivatives, diisocyanates, and bis-active
fluorine compounds. In particular embodiments, the modi-
fied J-chain is modified by insertion of an enzyme recogni-
tion site, and by post-translationally attaching a binding
moiety at the enzyme recognition site through a peptide or
non-peptide linker.

In certain aspects the modified J-chain can include the
formula $X[L_n]J$ or $J[L_n]X$, where J includes a mature native
J-chain or functional fragment thereof, X includes a heter-
ologous binding domain, and $[L_n]$ is a linker sequence
including n amino acids, where n is a positive integer from
1 to 100, 1 to 50, or 1 to 25. In certain aspects N is 5, 10,
15, or 20.

J-chains from the following species can also be used in
certain embodiments: Pan troglodytes, *Pongo abelii, Calli-
thrix jacchus, Macaca mulatta, Papio Anubis, Saimiri
boliviensis, Tupaia chinensis, Tursiops truncatus, Orcinus
orca, Loxodonta Africana, Leptonychotes weddellii, Cera-
totherium simum, Felis catus, Canis familiaris, Ailuropoda
melanoleuca, Mustela furo, Equus caballus, Cavia porcel-
lus, Camelus ferus, Capra hircus, Chinchilla lanigera,
Mesocricetus auratus, Ovis aries, Myotis lucifugus, Pan-
tholops hodgsonii, Bos taurus, Mus musculus, Rattus nor-
vegicus, Echinops telfairi, Oryctolagus cuniculus, Monodel-
phis domestica, Alligator mississippiensis, Chrysemys picta,*

*Sarcophilus harrisii, Ornithorhynchus anatinus, Melopsittacus undulatus, Anas platyrhynchos, Gallus gallus, Meleagris gallopavo, Falco peregrinus, Zonotrichia albicollis,* and *Pteropus alecto.*

When HcAbs are utilized additional modifications to Fc regions can be incorporated. In particular embodiments, one or more amino acid modifications may be introduced into the Fc region of an HcAb, thereby generating an Fc region variant. The Fc region variant may include a human Fc region sequence (e.g., a human IgG1, IgG2, IgG3 or IgG4 Fc region) including an amino acid modification (e.g., a substitution) at one or more amino acid positions. Numerous Fc variants are described below that provide administration benefits.

In particular embodiments, variants have been modified from a reference sequence to produce an administration benefit. Exemplary administration benefits can include (1) reduced susceptibility to proteolysis, (2) reduced susceptibility to oxidation, (3) altered binding affinity for forming protein complexes, (4) altered binding affinities, (5) reduced immunogenicity; and/or (6) extended half-live.

In particular embodiments, the Fc portion of an antibody (e.g., an HcAb) can be mutated to increase its affinity for Fc receptors. Exemplary mutations that increase the affinity for Fc receptors include: G236A/S239D/A330L/I332E (GAS-DALIE). Smith et al., Proceedings of the National Academy of Sciences of the United States of America, 109(16), 6181-6186, 2012. In particular embodiments, a antibody variant includes an Fc region with one or more amino acid substitutions which improve ADCC, e.g., substitutions at positions 298, 333, and/or 334 of the Fc region (EU numbering of residues). In particular embodiments, alterations are made in the Fc region that result in altered Clq binding and/or Complement Dependent Cytotoxicity (CDC), e.g., as described in U.S. Pat. No. 6,194,551, WO 99/51642, and Idusogie et al., J. Immunol. 164: 4178-4184, 2000.

In particular embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further below. In particular embodiments, residue 5400 (EU numbering) of the heavy chain Fc region is selected. Cysteine engineered antibodies may be generated as described, e.g., in U.S. Pat. No. 7,521,541.

Antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at position 297 in the Fc region (Eu numbering of Fc region residues); however, Asn297 may also be located ±3 amino acids upstream or downstream of position 297, i.e., between positions 294 and 300, due to minor sequence variations in antibodies. Such fucosylation variants may have improved ADCC function. See, e.g., WO2000/61739; WO 2001/

29246; WO2002/031140; US2002/0164328; WO2003/085119; WO2003/084570; US2003/0115614; US2003/0157108; US2004/0093621; US2004/0110704; US2004/0132140; US2004/0110282; US2004/0109865; WO2005/035586; WO2005/035778; WO2005/053742; Okazaki et al. J. Mol. Biol. 336:1239-1249 (2004); and Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545, 1986, and knockout cell lines, such as alpha-1,6-fucosyltransferase gene, FUT8, knockout CHO cells (see, e.g., Yamane-Ohnuki et al., Biotech. Bioeng. 87: 614, 2004; Kanda et al., Biotechnol. Bioeng., 94(4):680-688, 2006; and WO2003/085107).

In particular embodiments, modified antibodies include those wherein one or more amino acids have been replaced with a non-amino acid component, or where the amino acid has been conjugated to a functional group or a functional group has been otherwise associated with an amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. Amino acid(s) can be modified, for example, co-translationally or post-translationally during recombinant production (e.g., N-linked glycosylation at N-X-S/T motifs during expression in mammalian cells) or modified by synthetic means. The modified amino acid can be within the sequence or at the terminal end of a sequence. Modifications also include nitrited constructs.

In particular embodiments, variants include glycosylation variants wherein the number and/or type of glycosylation site has been altered compared to the amino acid sequences of a reference sequence. In particular embodiments, glycosylation variants include a greater or a lesser number of N-linked glycosylation sites than the reference sequence. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (e.g., those that are naturally occurring) are eliminated and one or more new N-linked sites are created. Additional antibody variants include cysteine variants wherein one or more cysteine residues are deleted from or substituted for another amino acid (e.g., serine) as compared to the reference sequence. These cysteine variants can be useful when antibody must be refolded into a biologically active conformation such as after the isolation of insoluble inclusion bodies. These cysteine variants generally have fewer cysteine residues than the reference sequence, and typically have an even number to minimize interactions resulting from unpaired cysteines.

PEGylation particularly is a process by which polyethylene glycol (PEG) polymer chains are covalently conjugated to other molecules such as proteins. Several methods of PEGylating proteins have been reported in the literature. For example, N-hydroxy succinimide (NHS)-PEG was used to PEGylate the free amine groups of lysine residues and N-terminus of proteins; PEGs bearing aldehyde groups have been used to PEGylate the amino-termini of proteins in the presence of a reducing reagent; PEGs with maleimide functional groups have been used for selectively PEGylating the free thiol groups of cysteine residues in proteins; and site-specific PEGylation of acetyl-phenylalanine residues can be performed.

Covalent attachment of proteins to PEG has proven to be a useful method to increase the half-lives of proteins in the body (Abuchowski, A. et al., Cancer Biochem. Biophys., 1984, 7:175-186; Hershfield, M. S. et al., N. Engl. J. Medicine, 1987, 316:589-596; and Meyers, F. J. et al., Clin. Pharmacol. Ther., 49:307-313, 1991). The attachment of PEG to proteins not only protects the molecules against enzymatic degradation, but also reduces their clearance rate from the body. The size of PEG attached to a protein has significant impact on the half-life of the protein. The ability of PEGylation to decrease clearance is generally not a function of how many PEG groups are attached to the protein, but the overall molecular weight of the altered protein. Usually the larger the PEG is, the longer the in vivo half-life of the attached protein. In addition, PEGylation can also decrease protein aggregation (Suzuki et al., Biochem. Bioph. Acta 788:248, 1984), alter protein immunogenicity (Abuchowski et al., J. Biol. Chem. 252: 3582, 1977), and increase protein solubility as described, for example, in PCT Publication No. WO 92/16221).

Several sizes of PEGs are commercially available (Nektar Advanced PEGylation Catalog 2005-2006; and NOF DDS Catalogue Ver 7.1), which are suitable for producing proteins with targeted circulating half-lives. A variety of active PEGs have been used including mPEG succinimidyl succinate, mPEG succinimidyl carbonate, and PEG aldehydes, such as mPEG-propionaldehyde.

In particular embodiments, the antibody can be fused or coupled to an Fc polypeptide that includes amino acid alterations that extend the in vivo half-life of an antibody that contains the altered Fc polypeptide as compared to the half-life of a similar antibody containing the same Fc polypeptide without the amino acid alterations. In particular embodiments, Fc polypeptide amino acid alterations can include M252Y, T252L, T253S, S254T, T254F, T256E, T256N, E294delta, T307P, A379V, S383N, M428L, N434S, N434A, N434Y, and/or R435H. These mutations are described in more detail in Stapleton et al., (*Nat. Comm.* (2011)2:599); Shields et al., (*J. Biol. Chem.* (2001) 276: 6591-604); Monnet et al., (*Mabs* (2014) 6:422-36); Bas et al., (*J. Immunol.* (2019) 202:1582094); Zalevsky et al., (*Nature Biotechnology* 28, 157-159, 2010); and Dall'acqua et al., (*J. Immunol.* (2002) 169: 5171-80); Ghetie et al., (*Nat. Biotechnol.* (1997) 15:637-40). Other alterations that can be helpful are described in U.S. Pat. Nos. 7,083,784, 7,670,600, US Publication No. 2010/0234575, PCT/US2012/070146, and Zwolak, Scientific Reports 7: 15521, 2017. In particular embodiments, any substitution at one of the following amino acid positions in an Fc polypeptide can be considered an Fc alteration that extends half-life: 250, 251, 252, 253, 254, 256, 294, 259, 307, 308, 332, 378, 379, 380, 383,428, 430, 434, 435, 436. Each of these alterations or combinations of these alterations can be used to extend the half-life of an antibody described herein.

For additional information regarding Fc mutations that create administration benefits, see Saunders, Conceptual Approaches to Modulating Antibody Effector Functions and Circulation Half-Life, Frontiers in Immunology (2019) Vol. 10, Article 1296.

(iv) Multi-Domain Binding Molecules. Multi-domain binding molecules include at least two binding domains, wherein at least one binding domain includes an anti-ROR1 binding domain disclosed herein. In particular embodiments, a multi-domain binding molecule includes at least one, at least two, at least three, at least four binding domains that bind an epitope on ROR1. In particular embodiments, all of the binding domains of a multi-domain binding molecule bind ROR1. In particular embodiments, a multi-domain binding molecule includes at least two single-domain antibodies linked together. In particular embodiments, a multi-domain binding molecule includes at least one single-domain antibody linked to at least one conventional antibody. In particular embodiments, a multi-domain binding molecule includes at least one single-domain antibody linked to an antibody or fragment thereof. In particular embodiments, a multi-domain binding molecule includes at least one single-domain antibody described herein. In particular embodiments, a multi-domain binding molecule includes at least one HcAb described herein. In particular embodiments, an HcAb is a multi-domain binding molecule.

Multi-domain binding molecules include bispecific antibodies which bind at least two epitopes wherein at least one of the epitopes is located on ROR1. Multi-domain binding molecules include trispecific antibodies which binds at least 3 epitopes, wherein at least one of the epitopes is located on ROR1, and so on.

Bispecific antibodies can be prepared utilizing antibody fragments (for example, F(ab')$_2$ bispecific antibodies). For example, WO 1996/016673 describes a bispecific anti-ErbB2/anti-Fc gamma RIII antibody; U.S. Pat. No. 5,837, 234 describes a bispecific anti-ErbB2/anti-Fc gamma RI antibody; WO 1998/002463 describes a bispecific anti-ErbB2/Fc alpha antibody; and U.S. Pat. No. 5,821,337 describes a bispecific anti-ErbB2/anti-CD3 antibody.

Some additional exemplary bispecific antibodies have two heavy chains (each having three heavy chain CDRs, followed by (N-terminal to C-terminal) a CH1 domain, a hinge, a CH2 domain, and a CH3 domain), and two immunoglobulin light chains that confer antigen-binding specificity through association with each heavy chain. However, as indicated, additional architectures are envisioned, including bi-specific antibodies in which the light chain(s) associate with each heavy chain but do not (or minimally) contribute to antigen-binding specificity, or that can bind one or more of the epitopes bound by the heavy chain antigen-binding regions, or that can associate with each heavy chain and enable binding of one or both of the heavy chains to one or both epitopes.

Two single-domain antibodies can be linked through a linker to form a bispecific antibody. In particular embodiments, the two single-domain antibodies can bind the same epitope or different epitopes. Examples of linkers can be found in Chen et al., Adv Drug Deliv Rev. 2013 Oct. 15; 65(10): 1357-1369. Linkers can be flexible, rigid, or semi-rigid, depending on the desired functional domain presentation to a target.

Commonly used flexible linkers include a linker sequence with the amino acids glycine and serine (Gly-Ser linkers). In particular embodiments, the linker sequence includes sets of glycine and serine repeats such as from one to ten repeats of (Gly$_x$Ser$_y$)$_n$, wherein x and y are independently an integer from 0 to 10 provided that x and y are not both 0 and wherein n is an integer of 1, 2, 3, 4, 5, 6, 7, 8, 9 or 10). Particular examples include (Gly$_4$Ser)$_n$ (SEQ ID NO: 47), (Gly$_3$Ser)$_n$, (Gly$_4$Ser)$_n$ (SEQ ID NO: 48), (Gly$_3$Ser)$_n$(Gly$_2$Ser)$_n$ (SEQ ID NO: 49), and (Gly$_3$Ser)$_n$(Gly$_4$Ser)$_1$ (SEQ ID NO: 50). In particular embodiments, the linker is (Gly$_4$Ser)$_4$ (SEQ ID NO: 51), (Gly$_4$Ser)$_3$ (SEQ ID NO: 52), (Gly$_4$Ser)$_2$ (SEQ ID NO: 53), (Gly$_4$Ser)$_1$ (SEQ ID NO: 54), (Gly$_3$Ser)$_2$ (SEQ ID NO: 55), (Gly$_3$Ser)$_1$ (SEQ ID NO: 56), (Gly$_2$Ser)$_2$ (SEQ ID NO: 57) or (Gly$_2$Ser)$_1$, GGSGGGSGGSG (SEQ ID NO: 58), GGSGGGSGSG (SEQ ID NO: 59), or GGSGGGSG (SEQ ID NO: 60).

Linkers that include one or more antibody hinge regions and/or immunoglobulin heavy chain constant regions, such as CH3 alone or a CH2CH3 sequence can also be used.

In some situations, flexible linkers may be incapable of maintaining a distance or positioning of binding domains needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs).

Other forms of bispecific binding molecules include the single chain "Janusins" described in Traunecker et al. (Embo Journal, 10, 3655-3659, 1991).

Bispecific binding molecules with extended half-lives are described in, for example, U.S. Pat. No. 8,921,528 and US Patent Publication No. 2014/0308285.

In certain examples, a secondary binding domain binds CD19. CD19 binding domains can be derived from, for example, Blinatumomab; SJ25C1 (Bejcek et al. Cancer Res 2005, PMID 7538901); HD37 (Pezutto et al. JI 1987, PMID 2437199); and FMC63.

In particular embodiments, a CD19 binding domain includes a variable light chain region including the sequence DIQLTQSPSSLSASVGDRVTITCKASQSVDYDGD-SYLNWYQQIPGKAPKLLIYDASNLVSGIPPR FSGSGSGTDYTFTISSLQPEDIATYHCQQST-EDPWTFGGGTKLQIKR (SEQ ID NO: 61), and a variable heavy chain region including sequence

```
                                 (SEQ ID NO: 62)
QVQLQQSGAEVKKPGSSVKVSCKASGYAFSSYWMNWVRQRPGQGLEWIGQ

IWPGDGDTNYNGKFKGRATITADESTNTAYMELSSLRSEDTAFYSCARRE

TTTVGRYYYAMDYWGQGTTVTVSS.
```

In particular embodiments, a CD19 binding domain is human or humanized and includes a variable light chain including a CDRL1 sequence including DYYMH (SEQ ID NO: 63), a CDRL2 sequence including SRLHSGV (SEQ ID NO: 64), and a CDRL3 sequence including GNTLPYTFG (SEQ ID NO: 65), and a variable heavy chain including a CDRH1 sequence including DYGVS (SEQ ID NO: 66), a CDRH2 sequence including VTWGSETTYYNSALKS (SEQ ID NO: 67), and a CDRH3 sequence including YAMDYWG (SEQ ID NO: 68).

In particular embodiments, the binding domain is human or humanized and includes a variable light chain including a CDRL1 sequence including KASQSVDYDGDSYLN (SEQ ID NO: 69), a CDRL2 sequence including DASNLVS (SEQ ID NO: 70), and a CDRL3 sequence including QQST-EDPWT (SEQ ID NO: 71), and a variable heavy chain including a CDRH1 sequence including SYWMN (SEQ ID NO: 72), a CDRH2 sequence including QIWPGDGDTNYNGKFKG (SEQ ID NO: 73), and a CDRH3 sequence including RETTTVGRYYYAMDY (SEQ ID NO: 74).

Because albumin has an extended serum half-life, it can be of use in improving the pharmacokinetics of administered single-domain antibodies. In particular embodiments, single-domain antibodies can be linked to albumin. In other particular embodiments, single-domain antibodies can be linked to albumin-binding domains (ABDs). ABDs include, for example, albumin-binding peptides, antibodies, antibody fragments, single-domain antibodies, and designed ankyrin repeat proteins (DARPins).

In particular embodiments, multi-domain binding molecules with extended half-lives include multi-domain binding molecules wherein at least one binding domain binds albumin. In particular embodiments, the multi-domain binding molecule that binds albumin includes a binding domain that binds ROR1 linked to a binding domain that binds albumin. In particular embodiments, the multi-domain binding molecule that binds albumin includes a single-domain antibody that binds ROR1 linked to a single-domain antibody that binds albumin.

In particular embodiments, an albumin-binding domain has the sequence: DITGAALLEAKEAAINELKQYGIS-DYYVTLINKAKTVEGVNALKAEILSALP (SEQ ID NO: 75). In particular embodiments, an albumin-binding domain includes a variant of the sequence as set forth in SEQ ID NO: 75, wherein the variant sequence is modified by at least one amino acid substitution selected from the group including: E12D, T29H-K35D, and A45D.

In particular embodiments, an albumin-binding domain includes the sequence: LKEAKEKAIEELKK-AGITSDYYFDLINKAKTVEGVNALKDEILKA (SEQ ID NO: 76). In particular embodiments, an albumin-binding domain includes a variant of the sequence as set forth in SEQ ID NO: 76, wherein the variant sequence is modified by at least one amino acid substitution selected from the group including: Y21, Y22, L25, K30, T31, E33, G34, A37, L38, E41, 142 and A45.

Additional binding domains that bind albumin include CA645 as described in Adams et al., 2016 MAbs 8(7): 1336-1346 (see, e.g., Protein Data Bank accession codes 5FUZ and 5FUO); anti-HSA Nanobody™ (Ablynx, Ghent, Belgium), AlbudAb™ (GlaxoSmithKline, Brentford, United Kingdom), and other high-affinity albumin nanobody sequences as described in Shen et al., 2020 bioRxiv doi: doi.org/10.1101/2020.08.19.257725; Mester, et al., 2021 mAbs. 13:1; Tijink et al., 2008 Mol Cancer Ther (7) (8) 2288-2297; and Roovers et al., Cancer Immunol Immunother 2007; 56: 303-317.

In particular embodiments, binding domains disclosed herein can be used to create bi-tri, (or more) specific immune cell engaging molecules. Immune cell engaging molecules have at least one binding domain that binds a receptor on an immune cell and alters the activation state of the immune cell. Examples of multi-domain immune cell engaging molecules include those which bind both an immune cell (e.g., T-cell or NK-cells) activating epitope and ROR1, with the goal of bringing immune cells to ROR1-expressing cells to destroy them. See, for example, US 2008/0145362. Such molecules are referred to herein as immune-activating multi-specifics or I-AMS). BiTEs® (Amgen, Thousand Oaks, CA) or bispecific T cell engagers are a form of I-AMS. Immune cells that can be targeted for localized activation by I-AMS within the current disclosure include, for example, B-cells, T-cells, natural killer (NK) cells, and macrophages which are discussed in more detail herein.

I-AMS disclosed herein can target any T-cell activating epitope that upon binding induces T-cell activation. Examples of such T-cell activating epitopes are on T-cell markers including CD2, CD3, CD7, CD27, CD28, CD30, CD40, CD83, 4-1BB (CD137), OX40, lymphocyte function-associated antigen-1 (LFA-1), LIGHT, NKG2C, and B7-H3.

In particular embodiments, the CD3 binding domain (e.g., scFv) is derived from the OKT3 antibody (the same as the one utilized in blinatumomab), otelixizumab, teplizumab, visilizumab, 20G6-F3, 4B4-D7, 4E7-C9, 18F5-H10, or TR66. The OKT3 antibody is described in detail in U.S. Pat. No. 5,929,212.

In particular embodiments, the OKT3 binding domain includes a variable light chain of QIVLTQSPAIM-SASPGEKVTMTCSASSSVSYMNWYQQKSGTSPKR-WIYDTSKLASGVPAHFR GSGSGTSYSLTISGMEAE-DAATYYCQQWSSNPFTFGSGTKLEINR (SEQ ID NO: 77) and a variable heavy chain of

```
                                        (SEQ ID NO: 78)
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSAKTTAPSVYPLAPVCGDTTGSSVTLGCLVKG

YFPEPVTLTWNSGSLSSGVHTFPAVLQSDLYTLSSSVTVTSS.
```

In particular embodiments, the binding domain includes a variable light chain including a CDRL1 sequence including SASSSVSYMN (SEQ ID NO: 79), a CDRL2 sequence including DTSKLAS (SEQ ID NO: 80), a CDRL3 sequence including QQWSSNPFTF (SEQ ID NO: 81), a CDRH1 sequence including RYTMH (SEQ ID NO: 82), a CDRH2 sequence including YINPSRGYTNYNQKFKD (SEQ ID NO: 83), and a CDRH3 sequence including YYDDHYCL (SEQ ID NO: 84). In particular embodiments, the binding domain is human or humanized. For more information regarding binding domains that bind CD3, see U.S. Pat. No. 8,785,604, PCT/US 17/42264, and/or WO02051871.

In particular embodiments, a binding domain is "derived from" a reference antibody when the binding domain includes the CDRs of the reference antibody, according to a known numbering scheme (e.g., Kabat, Chothia, Martin, or others).

CD28 binds to B7-1 (CD80) and B7-2 (CD86) and is the most potent of the known co-stimulatory molecules (June et al., Immunol. Today 15:321, 1994; Linsley et al., Ann. Rev. Immunol. 11:191, 1993). In particular embodiments, the CD28 binding domain is derived from TGN1412, CD80, CD86 or the 9D7 antibody. Additional antibodies that bind CD28 include 9.3, KOLT-2, 15E8, 248.23.2, and EX5.3D10.

In particular embodiments, the binding domain that binds CD28 is derived from TGN-1412 and/or theralizumab. In particular embodiments, the binding domain includes a variable light chain of DIQMTQSPSSL-SASVGDRVTITCKTNENIYSNLAWYQQKDGK-SPQLLIYAATHLVEGVPSRFSG SGSGTQYS-LTISSLQPEDFGNYYCQHFWGTPXTFGGGTKLEI KR, wherein X=C, A, or N. (SEQ ID NO: 85) and a variable heavy chain of VQLQQSGAELKKPGASVKVSCK-ASGYTFTEYIIHWIKLRSGQGLEWIGWFYPG-SNDIQYNAQF KGKATLTADKSSSTVYMELTGLTPED-SAVYFCARRDDFSGYDALPYWGQGTLVTVSA (SEQ ID NO: 86). In particular embodiments, the binding domain includes a variable light chain including a CDRL1 sequence including HASQNIYVWLN (SEQ ID NO: 87), a CDRL2 sequence including KASNLHT (SEQ ID NO: 88), a CDRL3 sequence including QQGQTYPYT (SEQ ID NO: 89), a CDRH1 sequence including SYYIH (SEQ ID NO: 90), a CDRH2 sequence including CIYPGNVNTNYNEKFKD (SEQ ID NO: 91), and a CDRH3 sequence including SHY-GLDWNFDV (SEQ ID NO: 92). In particular embodiments, the binding domain is human or humanized. For more information regarding binding domains that bind CD28, see U.S. Pat. No. 8,785,604 and/or WO02051871.

Activated T-cells express 4-1BB (CD137). In particular embodiments, the 4-1BB binding domain includes a variable light chain including a CDRL1 sequence including RASQSVS (SEQ ID NO: 93), a CDRL2 sequence including ASNRAT (SEQ ID NO: 94), and a CDRL3 sequence including QRSNWPPALT (SEQ ID NO: 95) and a variable heavy chain including a CDRH1 sequence including YYWS (SEQ ID NO: 96), a CDRH2 sequence including INH, and a CDRH3 sequence including YGPGNYDWYFDL (SEQ ID NO: 97).

Particular embodiments disclosed herein including binding domains that bind epitopes on CD8. In particular embodiments, the CD8 binding domain (e.g., scFv) is derived from the OKT8 antibody.

In particular embodiments natural killer cells (also known as NK-cells, K-cells, and killer cells) are targeted for localized activation by I-AMS. NK cells can induce apoptosis or cell lysis by releasing granules that disrupt cellular membranes and can secrete cytokines to recruit other immune cells.

Examples of commercially available antibodies that bind to an NK cell receptor and induce and/or enhance activation of NK cells include: 5C6 and 1D11, which bind and activate NKG2D (available from BioLegend® San Diego, CA); mAb 33, which binds and activates KIR2DL4 (available from BioLegend®); P44-8, which binds and activates NKp44 (available from BioLegend®); SK1, which binds and activates CD8; and 3G8 which binds and activates CD16.

Binding domains of I-AMS and other engineered formats described herein may be joined through a linker. As indicated previously, a linker is an amino acid sequence which can provide flexibility and room for conformational movement between the binding domains of a I-AM. Any appropriate linker may be used.

(v) Antibody Conjugates. An antibody conjugate includes a single-domain, an HcAb including a single-domain antibody, or a multi-domain binding molecule including a single-domain antibody disclosed herein linked to another molecule, other than an additional binding domain. Examples of antibody conjugates include antibody immunotoxins, antibody-drug conjugates (ADCs), antibody radioisotope conjugates, antibody detectable label conjugates, and antibody-particle conjugates.

Antibody Immunotoxins. In particular embodiments, the single-domain antibody can be formed as an antibody immunotoxin. Antibody immunotoxins include a single-domain antibody or HcAb disclosed herein conjugated to one or more cytotoxins (e.g., protein toxins, enzymatically active toxins of bacterial, fungal, plant, or animal origin, or fragments thereof). A toxin can be any agent that is detrimental to cells. Frequently used plant toxins are divided into two classes: (1) holotoxins (or class II ribosome inactivating proteins), such as ricin, abrin, mistletoe lectin, and modeccin, and (2) hemitoxins (class I ribosome inactivating proteins), such as pokeweed antiviral protein (PAP), saporin, Bryodin 1, bouganin, and gelonin. Commonly used bacterial toxins include diphtheria toxin (DT) and *Pseudomonas* exotoxin (PE). Kreitman, Current Pharmaceutical Biotechnology 2:313-325 (2001). The toxin may be obtained from essentially any source and can be a synthetic or a natural product.

Immunotoxins with multiple (e.g., four) cytotoxins per binding domain can be prepared by partial reduction of the binding domain with an excess of a reducing reagent such as dithiothreitol (DTT) or tris(2-carboxyethyl)phosphine (TCEP) at 37° C. for 30 min, then the buffer can be exchanged by elution through SEPHADEX G-25 resin with 1 mM DTPA (diethylene triamine penta-acetic acid) in Dulbecco's phosphate-buffered saline (DPBS). The eluent can be diluted with further DPBS, and the thiol concentration of the binding domain can be measured using 5,5'-dithiobis(2-nitrobenzoic acid) [Ellman's reagent]. An excess, for example 5-fold, of the linker-cytotoxin conjugate can be added at 4° C. for 1 hr, and the conjugation reaction can be quenched by addition of a substantial excess, for example 20-fold, of cysteine. The resulting immunotoxin mixture can be purified on SEPHADEX G-25 equilibrated in PBS to remove unreacted linker-cytotoxin conjugate, desalted if desired, and purified by size-exclusion chromatography. The resulting immunotoxin can then be sterile filtered, for example, through a 0.2 μm filter, and can be lyophilized if desired for storage.

Antibody-drug conjugates allow for the targeted delivery of a drug moiety to a cell expressing and displaying portions of ROR1 proteins and, in particular embodiments intracellular accumulation therein, where systemic administration of unconjugated drugs may result in unacceptable levels of toxicity to normal cells (Polakis P. (2005) Current Opinion in Pharmacology 5:382-387).

In particular embodiments, antibody-drug conjugates refer to targeted molecules which combine properties of both antibodies and cytotoxic drugs (e.g., chemotherapeutic drugs) by targeting potent cytotoxic drugs to antigen-expressing cells (Teicher, B. A. (2009) Current Cancer Drug Targets 9:982-1004), thereby enhancing the therapeutic index by maximizing efficacy and minimizing off-target toxicity (Carter, P. J. and Senter P. D. (2008) The Cancer Jour. 14(3):154-169; Chari, R. V. (2008) Acc. Chem. Res. 41:98-107). See also Kamath & Iyer (Pharm Res. 32(11): 3470-3479, 2015), which describes considerations for the development of antibody-drug conjugates.

The drug moiety (D) of an antibody-drug conjugate may include any compound, moiety or group that has a cytotoxic or cytostatic effect. Drug moieties may impart their cytotoxic and cytostatic effects by mechanisms including tubulin binding, DNA binding or intercalation, and inhibition of RNA polymerase, protein synthesis, and/or topoisomerase. Exemplary drugs include actinomycin D, anthracycline, auristatin, calicheamicin, camptothecin, CC1065, colchicin, cytochalasin B, daunorubicin, 1-dehydrotestosterone, dihydroxy anthracinedione, dolastatin, doxorubicin, duocarmycin, elinafide, emetine, ethidium bromide, etoposide, gramicidin D, glucocorticoids, lidocaine, maytansinoid (including monomethyl auristatin E [MMAE]; vedotin), mithramycin, mitomycin, mitoxantrone, nemorubicin, PNU-159682, procaine, propranolol, puromycin, pyrrolobenzodiazepine (PBD), taxane, taxol, tenoposide, tetracaine, trichothecene, vinblastine, vinca alkaloid, vincristine, and stereoisomers, isosteres, analogs, and derivatives thereof that have cytotoxic activity.

The drug may be obtained from essentially any source; it may be synthetic or a natural product isolated from a selected source, e.g., a plant, bacterial, insect, mammalian or fungal source. The drug may also be a synthetically modified natural product or an analogue of a natural product.

In particular embodiments, the antibody-drug conjugates include an antibody conjugated, i.e., covalently attached, to the drug moiety. In particular embodiments, the single-domain antibody or HcAb is covalently attached to the drug moiety through a linker. A linker can include any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid-based linker. The antibody-drug conjugate selectively delivers an effective dose of a drug to cells (e.g., cancer cells) whereby greater selectivity, i.e. a lower efficacious dose, may be achieved while increasing the therapeutic index ("therapeutic window").

To prepare antibody-drug conjugates, linker-cytotoxin conjugates can be made by conventional methods analogous to those described by Doronina et al. (Bioconjugate Chem. 17: 114-124, 2006). Antibody-drug conjugates with multiple (e.g., four) drugs per antibody can be prepared by partial reduction of the antibody with an excess of a reducing reagent such as dithiothreitol (DTT) or tris(2-carboxyethyl) phosphine (TCEP) at 37° C. for 30 min, then the buffer can be exchanged by elution through SEPHADEX G-25 resin with 1 mM DTPA in Dulbecco's phosphate-buffered saline (DPBS). The eluent can be diluted with further DPBS, and the thiol concentration of the antibody can be measured using 5,5'-dithiobis(2-nitrobenzoic acid) [Ellman's reagent]. An excess, for example 5-fold, of the linker-cytotoxin conjugate can be added at 4° C. for 1 hr, and the conjugation reaction can be quenched by addition of a substantial excess, for example 20-fold, of cysteine. The resulting ADC mixture can be purified on SEPHADEX G-25 equilibrated in PBS to remove unreacted linker-cytotoxin conjugate, desalted if desired, and purified by size-exclusion chromatography. The resulting ADC can then be sterile filtered, for example, through a 0.2 μm filter, and can be lyophilized if desired for storage. Methods used to produce immunotoxins can similarly be used to prepare antibody-drug conjugates.

Antibody-radioisotope conjugates include a single-domain antibody or HcAb linked to a radioisotope for use in nuclear medicine. Nuclear medicine refers to the diagnosis and/or treatment of conditions by administering radioactive isotopes (radioisotopes or radionuclides) to a subject. Therapeutic nuclear medicine is often referred to as radiation therapy or radioimmunotherapy (RIT).

In certain examples, the single-domain antibody or HcAb is linked to a radioisotope through siderocalin. Siderocalin (Scn), also known as Lipocalin-2 or neutrophil gelatinase-associated lipocalin (NGAL), is a member of the lipocalin family of proteins that binds siderophores, a type of small chelator, with very high affinity (in the sub-nanomolar range). Siderophores secreted by microbes can steal iron from host organisms by binding tightly to iron and delivering the iron to the microbe. Scn secreted by host organisms can prevent iron-pirating by microbes, by sequestering siderophores and preventing their delivery back to the microbe. Therefore, high affinity binding to chelators is a natural function of Scn.

Scn also has an exceptionally stable protein structure, and therefore is an ideal binding partner for fusion proteins, as the stability of the Scn domain can impart stability on the whole fusion protein. Additionally, Scn naturally contains a secretion signal, so Scn can be a useful fusion partner for of a variety of peptides, proteins, and protein domains, including when extracellular expression is desired. Further, Scn possesses a single N-linked glycosylation site, which is involved in correct processing in the ER before secretion. Another advantage is that human Scn can be used, reducing stimulation of immune responses against it in human diagnostic and/or therapeutic uses. Making minimal (e.g., 3 or less or 2 or less) mutations to the Scn can also minimize the likelihood of immune response stimulation. For all of these reasons, Scn can be chosen as a chelator binding protein for embodiments disclosed herein.

In particular embodiments, Scn refers to a natural Scn sequence that retains its natural specificity for its chelator binding partners, such as carboxymycobactin and enterochelin. Retaining natural specificity means that there is no statistically significant difference in binding affinity when assessed under comparable conditions. In particular embodiments, Scn particularly refers to the human ortholog of Scn (SWISS-PROT Data Bank Accession Number P80188), which has 178 amino acids and a molecular weight of 20,547 Da (or P80188 with the first 20 amino acids deleted). In particular embodiments, Scn can refer to the ortholog expressed by another species, such as the mouse ortholog (SWISS-PROT Data Bank Accession Number P11672 with the first 20 amino acids deleted), or the rat ortholog (SWISS-PROT Data Bank Accession Number P30152 with the first 20 amino acids deleted). For additional orthologs, see Correnti & Strong, (2013) "Iron Sequestration in Immunity" In Metals in Cells, Encyclopedia of Inorganic and Bioinorganic Chemistry. (Culcotta & Scott, eds.) John Wiley & Sons, pp. 349-59.

Examples of radioactive isotopes that can be conjugated to single-domain antibodies or HcAb of the present disclosure include iodine-131, arsenic-72, arsenic-74, iodine-131, indium-111, yttrium-90, and lutetium-177, as well as alpha-emitting radionuclides such as astatine-211, actinium-225, bismuth-212 or bismuth-213. Methods for preparing radioimmunoconjugates are established in the art. Examples of radioimmunoconjugates are commercially available, including Zevalin™ (DEC Pharmaceuticals), and similar methods can be used to prepare radioimmunoconjugates using the antibodies of the disclosure.

Examples of radionuclides that are useful for radiation therapy include $^{225}$Ac and $^{227}$Th. $^{225}$Ac is a radionuclide with the half-life of ten days. As $^{225}$Ac decays the daughter isotopes $^{221}$Fr, $^{213}$Bi, and $^{209}$Pb are formed. $^{227}$Th has a half-life of 19 days and forms the daughter isotope $^{223}$Ra.

Additional examples of useful radioisotopes include $^{228}$Ac, $^{111}$Ag, $^{124}$Am, $^{74}$As, $^{211}$At, $^{209}$At, $^{194}$Au, $^{128}$Ba, $^{7}$Be, $^{206}$Bi, $^{245}$Bk, $^{246}$Bk, $^{76}$Br, $^{11}$C, $^{14}$C, $^{47}$Ca, $^{254}$Cf, $^{242}$Cm, $^{51}$Cr, $^{67}$Cu, $^{153}$Dy, $^{157}$Dy, $^{159}$Dy, $^{165}$Dy, $^{166}$Dy, $^{171}$Er, $^{250}$Es, $^{254}$Es, $^{147}$Eu, $^{157}$Eu, $^{52}$Fe, $^{59}$Fe, $^{251}$Fm, $^{252}$Fm, $^{253}$Fm, $^{66}$Ga, $^{72}$Ga, $^{146}$Gd, $^{153}$Gd, $^{68}$Ge, $^{3}$H, $^{170}$Hf, $^{171}$Hf, $^{193}$Hg, $^{193}$mHg, $^{160}$mHo, $^{130}$I, $^{131}$I, $^{135}$I, $^{114}$mIn, $^{185}$Ir, $^{42}$K, $^{43}$K, $^{76}$Kr, $^{79}$Kr, $^{81}$mKr, $^{132}$La, $^{262}$Lr, $^{169}$Lu, $^{174}$mLu, $^{176}$mLu, $^{257}$Md, $^{260}$Md, $^{28}$Mg, $^{52}$Mn, $^{90}$Mo, $^{24}$Na, $^{95}$Nb, $^{138}$Nd, $^{57}$Ni, $^{66}$Ni, $^{234}$Np, $^{15}$O, $^{182}$Os, $^{189}$mOs, $^{191}$Os, $^{32}$P, $^{201}$Pb, $^{101}$Pd, $^{143}$Pr, $^{191}$Pt, $^{243}$Pu, $^{225}$Ra, $^{81}$Rb, $^{188}$Re, $^{105}$Rh, $^{211}$Rn, $^{103}$Ru, $^{35}$S, $^{44}$Sc, $^{72}$Se, $^{153}$Sm, $^{125}$Sn, $^{91}$Sr, $^{173}$Ta, $^{154}$Tb, $^{127}$Te, $^{234}$Th, $^{45}$Ti, $^{166}$Tm, $^{230}$U, $^{237}$U, $^{240}$U, $^{48}$V, $^{178}$W, $^{181}$W, $^{188}$W, $^{125}$Xe, $^{127}$Xe, $^{133}$Xe, $^{133}$mXe, $^{135}$Xe, $^{85}$mY, $^{86}$Y, $^{90}$Y, $^{93}$Y, $^{169}$Yb, $^{175}$Yb, $^{65}$Zn, $^{71}$mZn, $^{86}$Zr, $^{95}$Zr, and/or $^{97}$Zr. Radioisotopes can be used as a type of detectable label called a radiolabel.

Antibody-detectable label conjugates include a single-domain antibody or HcAb linked to a detectable label. Detectable labels can include any suitable label or detectable group detectable by, for example, optical, spectroscopic, photochemical, biochemical, immunochemical, electrical, optical or chemical means. In particular embodiments, detectable labels can include radiolabels, chemiluminescent labels, spectral colorimetric labels, affinity tags, enzymatic labels, fluorescent labels, and contrast agents.

Chemiluminescent labels can include lucigenin, luminol, luciferin, isoluminol, theromatic acridinium ester, imidazole, acridinium salt, or oxalate ester.

Spectral colorimetric labels can include colloidal gold or colored glass or plastic (e.g., polystyrene, polypropylene, and latex) beads.

Affinity tags can include, for example, His tag (HHHHHH (SEQ ID NO: 98)), Flag tag (DYKDDDD (SEQ ID NO: 99), Xpress tag (DLYDDDDK (SEQ ID NO: 100)), Avi tag (GLNDIFEAQKIEWHE (SEQ ID NO: 101)), Calmodulin binding peptide (CBP) tag (KRRWKKNFIAVSAANRFK-KISSSGAL (SEQ ID NO: 102)), Polyglutamate tag (EE-EEEE (SEQ ID NO: 103)), HA tag (YPYDVPDYA (SEQ ID NO: 104)), Myc tag (EQKLISEEDL (SEQ ID NO: 105)), Strep tag (WRHPQFGG (SEQ ID NO: 106)), STREP® tag II (WSHPQFEK (SEQ ID NO: 107); IBA Institut fur Bioanalytik, Germany; see, e.g., U.S. Pat. No. 7,981,632), Softag 1 (SLAELLNAGLGGS (SEQ ID NO: 108)), Softag 3 (TQDPSRVG (SEQ ID NO: 109)), and V5 tag (GKPIPN-PLLGLDST (SEQ ID NO: 110)).

Enzymatic labels can produce, for example, a chemiluminescent signal, a color signal, or a fluorescent signal. Enzymes can include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Fluorescent labels can be particularly useful in cell staining, identification, imaging, and isolation uses. Exemplary fluorescent labels include blue fluorescent proteins (e.g. eBFP, eBFP2, Azurite, mKalama1, GFPuv, Sapphire, T-sapphire); cyan fluorescent proteins (e.g. eCFP, Cerulean, CyPet, AmCyan1, Midoriishi-Cyan, mTurquoise); green fluorescent proteins (e.g. GFP, GFP-2, tagGFP, turboGFP, EGFP, Emerald, Azami Green, Monomeric Azami Green (mAzamigreen)), CopGFP, AceGFP, avGFP, ZsGreenl, Oregon Green™ (Thermo Fisher Scientific)); Luciferase; orange fluorescent proteins (mOrange, mKO, Kusabira-Orange, Monomeric Kusabira-Orange, mTangerine, tdTomato); red fluorescent proteins (mKate, mKate2, mPlum, DsRed monomer, mCherry, mRuby, mRFP1, DsRed-Express, DsRed2, DsRed-Monomer, HcRed-Tandem, HcRedl, AsRed2, eqFP611, mRaspberry, mStrawberry, Jred, Texas Red™ (Thermo Fisher Scientific)); far red fluorescent proteins (e.g., mPlum and mNeptune); yellow fluorescent proteins (e.g., YFP, eYFP, Citrine, SYFP2, Venus, YPet, PhiYFP, ZsYellowl); and tandem conjugates.

Contrast agents for magnetic source imaging include paramagnetic or superparamagnetic ions, iron oxide particles, and water-soluble contrast agents. Paramagnetic and superparamagnetic ions can be selected from the group of metals including iron, copper, manganese, chromium, erbium, europium, dysprosium, holmium, and gadolinium.

Antibody-particle conjugates include an antibody linked to a particle. In particular embodiments, particles include microparticles, nanoparticles, nanoshells, nanobeads, microbeads, or nanodots. Particles can include, for example, latex beads, polystyrene beads, fluorescent beads, and/or colored beads, and can be made from organic matter and/or inorganic matter. They can be made of any suitable materials that allow for the conjugation of capture proteins, such as VHH/HcAb to their surface. Examples of suitable materials include: ceramics, glass, polymers, and magnetic materials. Suitable polymers include polystyrene, poly-(methyl methacrylate), poly-(lactic acid), (poly-(lactic-co-glycolic acid)), polyesters, polyethers, polyolefins, polyalkylene oxides, polyamides, polyurethanes, polysaccharides, celluloses, polyisoprenes, methylstyrene, acrylic polymers, thoria sol, latex, nylon, Teflon cross-linked dextrans (e.g., Sepharose), chitosan, agarose, and cross-linked micelles. Additional examples include carbon graphited, titanium dioxide, and paramagnetic materials. See, e.g., "Microsphere Detection Guide" from Bangs Laboratories, Fishers Ind. In particular embodiments, microparticles can be made of one or more materials. In particular embodiments, microparticles are paramagnetic microparticles. Particular embodiments utilize carboxy-modified polystyrene latex (CML) flow cytometry beads and/or magnetic MagPlex® (Luminex, Austin, TX) flow cytometry beads. In particular embodiments, particles can carry a payload.

(vi) Recombinant Receptors. Single-domain antibodies or HcAb disclosed herein can be utilized within recombinant receptors. In particular embodiments, a recombinant receptor includes a chimeric antigen receptor (CAR) or an engineered T cell receptor (eTCR).

Figure 7:
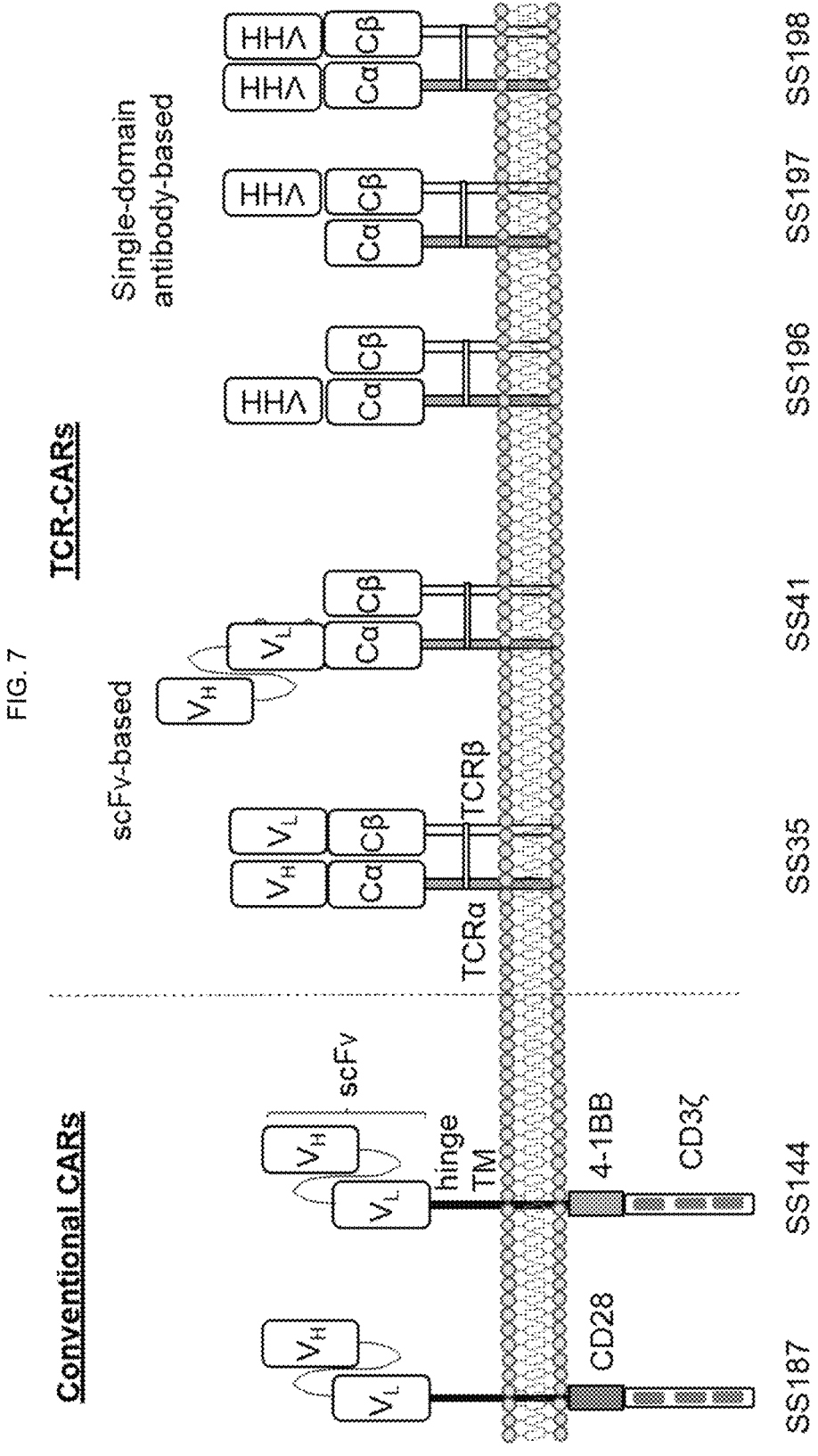
FIG. 7. Schematic of single-domain antibody (Nb)-based engineered T cell receptor (eTCR)-chimeric antigen receptors (CARs) and conventional CARs.
Figure 8A:
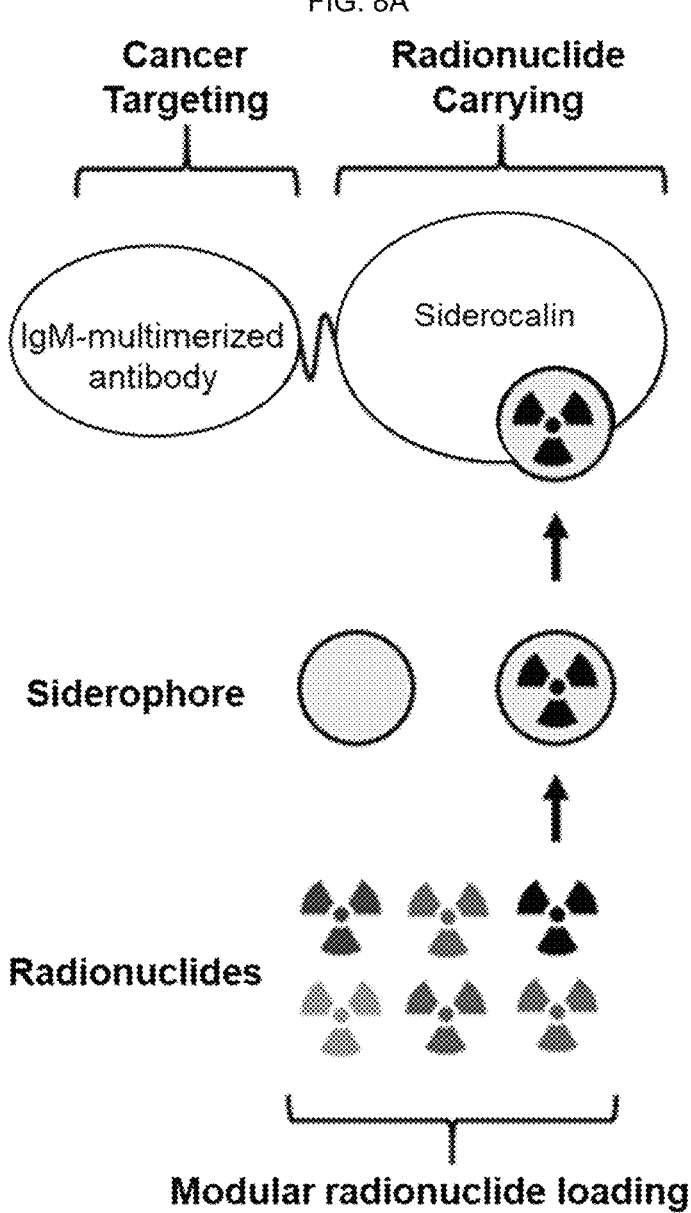
FIGS. 8A, 8B. Radionuclide conjugated single-domain antibodies (ScnAbs). (8A) Schematic of cancer targeted single-domain antibody attached to siderocalin carrying a siderophore. (8B) Characterization. Theoretical molecular weight of the mature peptide is 47313.43 kDa. Purification was conducted with HiLoad 16/600 Superdex 200 pg; OD280: 0.953 mg/ml; total yield: 22.9 mg; Endo Pass <0.500 EU/mg; and Buffer: phosphate buffered saline (PBS) with 5% glycerol. Only half of the Ni-NTA eluate was run over the SEC column.
Figure 8B:
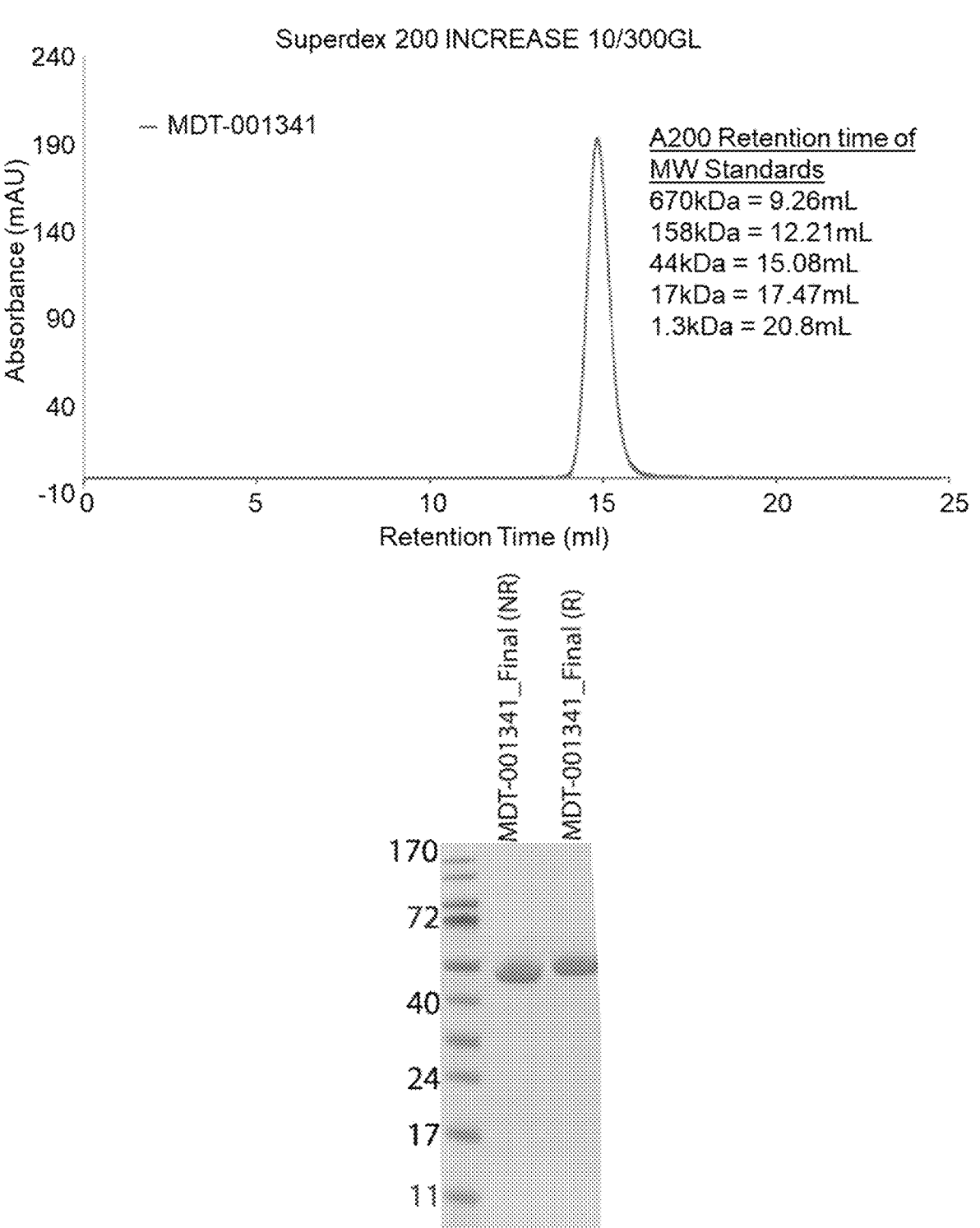
Figure 9:
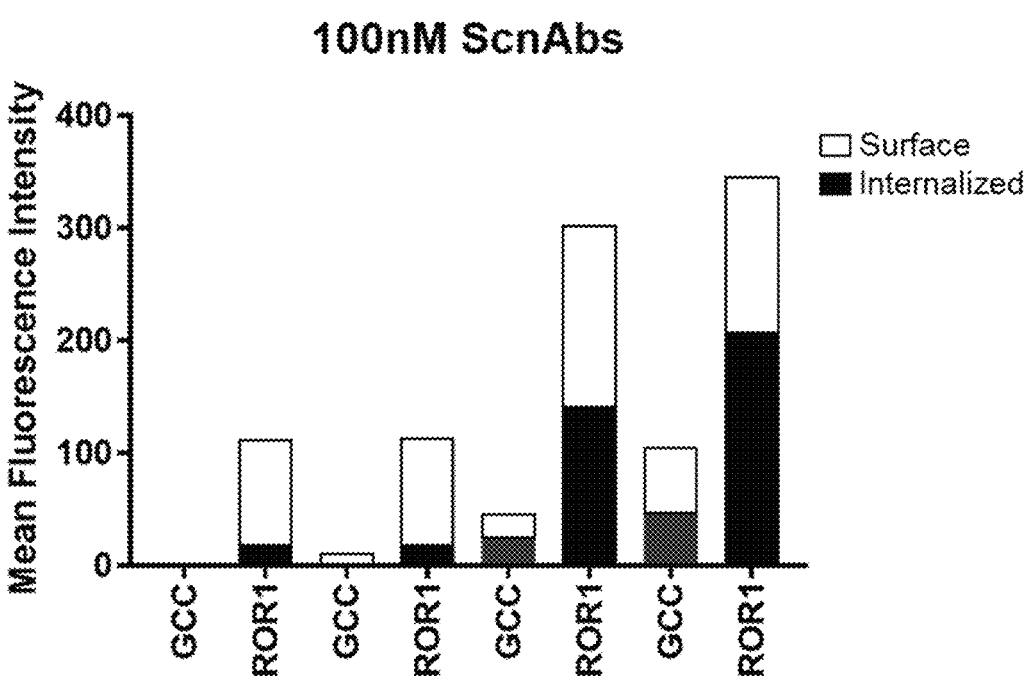
FIG. 9. Mean fluorescence intensity of surface and internalized ScnAbs on ROR1 and GCC.
Figure 10A:
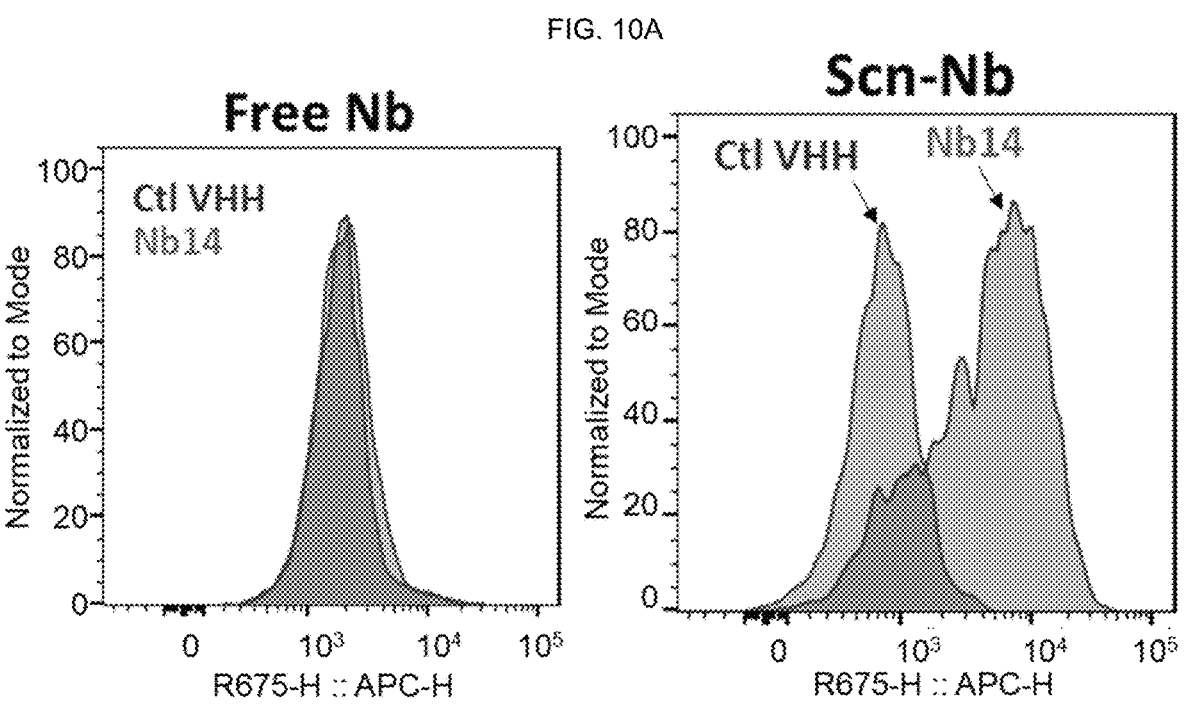
FIGS. 10A, 10B. Impact of valency on cancer targeting for (10A) colon cancer (Caco-2) which has high ROR1 expression and for (10B) neuroblastoma (LAN-1) which has low ROR1 expression. Constructs were conjugated with Alexafluor-A647.
Figure 10B:
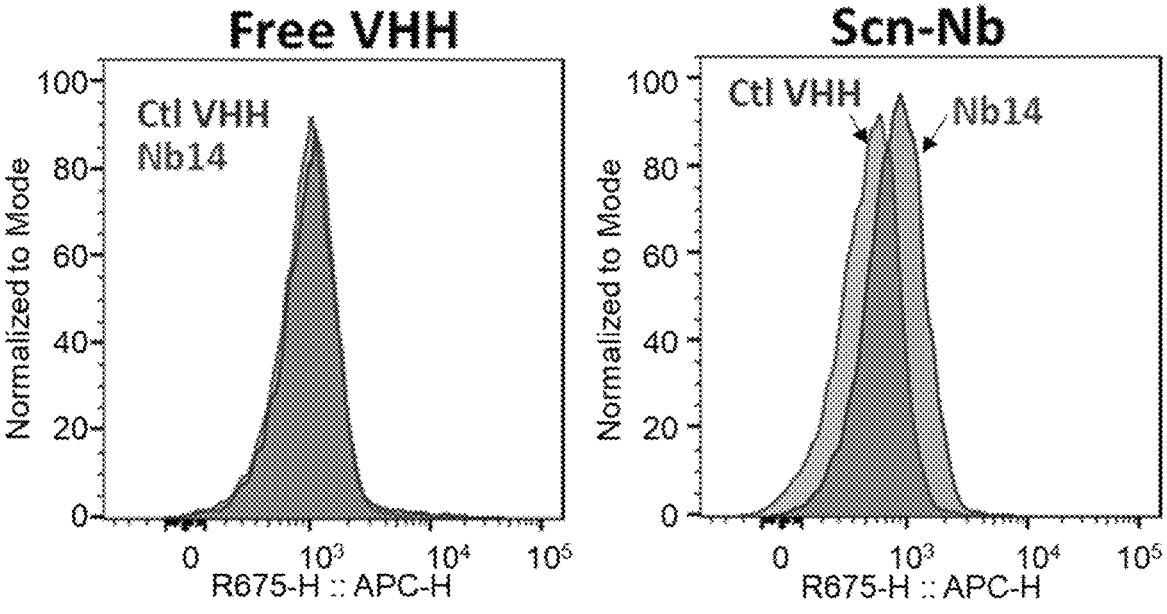

CAR include several distinct subcomponents that allow genetically modified cells (e.g., regulatory T cells) to recognize and kill cells expressing ROR1. The subcomponents include at least an extracellular component and an intracellular component. The extracellular component includes a binding domain that specifically binds an ROR1 epitope that is preferentially present on the surface of cells or in the area thereof. When the binding domain binds such epitopes, the intracellular component activates the cell to destroy the bound cell. CAR additionally include a transmembrane domain that directly or indirectly links the extracellular component to the intracellular component, and other subcomponents that can increase the CAR's function. For example, the inclusion of a spacer region and/or one or more linker sequences can allow the CAR to have additional conformational flexibility, often increasing the binding domain's ability to bind the targeted epitope.

eTCR disclosed herein include a single-domain antibody disclosed herein linked to the Cα and/or C$_\beta$ chains of a TCR (see, e.g., FIG. 7). A TCR is a heterodimeric fusion protein that typically includes an α and β chain. Each chain includes a variable region (V$_\alpha$ and V$_\beta$) and a constant region (C$_\alpha$ and C$_\beta$). In particular embodiments, an eTCR does not include the native TCR variable region but does include the native TCR constant region. In particular embodiments, the eTCR includes a single-domain antibody as the variable region of either the α and β chain. In particular embodiments, the eTCR includes a single-domain antibody as the variable region of both the α and β chain. In particular embodiments, eTCR include a C$_\alpha$ and/or C$_\beta$ chain sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a known or identified TCR Cα or Cβ.

Particular embodiments of binding domains include a VHH domain or single-domain antibody and/or the CDRs thereof as disclosed herein, such as those provided in SEQ ID NOs: 1-5 and 6-37.

Recombinant receptors can additionally include spacer regions, transmembrane domains, intracellular effector domains, transduction markers, and tags.

Spacer regions are used to create appropriate distances and/or flexibility between subcomponents of a protein. Spacer regions typically include 10 to 250 amino acids, 10 to 200 amino acids, 10 to 150 amino acids, 10 to 100 amino acids, 10 to 50 amino acids, or 10 to 25 amino acids. Exemplary spacer regions include all or a portion of an immunoglobulin hinge region.

Transmembrane domains typically have a three-dimensional structure that is thermodynamically stable in a cell membrane, and generally ranges in length from 15 to 30 amino acids. The structure of a transmembrane domain can include an α helix, a β barrel, a β sheet, a β helix, or any combination thereof. Transmembrane domains can include at least the transmembrane region(s) of the α, β or ζ chain of a T-cell receptor, CD28, CD27, CD3, CD45, CD4, CD5, CD8, CD9, CD16, CD22; CD33, CD37, CD64, CD80, CD86, CD134, CD137 and CD154.

A transmembrane domain can include one or more additional amino acids adjacent to the transmembrane region, e.g., one or more amino acid within the extracellular region of the expressed protein (e.g., up to 15 amino acids of the extracellular region) and/or one or more additional amino acids within the intracellular region of the expressed protein (e.g., up to 15 amino acids of the intracellular components).

Intracellular effector domains activate the expressing cell when the binding domain binds antigen (ROR1). The term "effector domain" is thus meant to include any portion of the intracellular domain sufficient to transduce an activation signal.

An effector domain can include one, two, three or more intracellular signaling components (e.g., receptor signaling domains, cytoplasmic signaling sequences), co-stimulatory domains, or combinations thereof. Exemplary effector domains include signaling and stimulatory domains selected from: 4-1BB (CD137), CD3γ, CD3δ, CD3ε, CD3ζ, CD27, CD28, DAP10, ICOS, LAG3, NKG2D, NOTCH1, OX40, ROR2, SLAMF1, TCRα, TCRβ, TRIM, Wnt, Zap70, or any combination thereof. In particular embodiments, exemplary effector domains include signaling and co-stimulatory domains selected from: CD86, FcγRIIa, DAP12, CD30, CD40, PD-1, lymphocyte function-associated antigen-1 (LFA-1), LIGHT, NKG2C, B7-H3, a ligand that specifically binds with CD83, CDS, ICAM-1, GITR, BAFFR, SLAMF7, NKp80 (KLRF1), CD127, CD19, CD4, CD8α, CD8β, IL2Rβ, IL2Rγ, IL7Rα, ITGA4, VLA1, CD49a, IA4, CD49D, ITGA6, VLA-6, CD49f, ITGAD, CD11d, ITGAE, CD103, ITGAL, CD11a, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), PSGL1, CD100 (SEMA4D), CD69, SLAMF6 (NTB-A, Ly108), SLAM (CD150, IPO-3), BLAME (SLAMF8), SELPLG (CD162), LTBR, GADS, PAG/Cbp, NKp44, NKp30, or NKp46.

Intracellular signaling component sequences that act in a stimulatory manner may include iTAMs. Examples of iTAMs including primary cytoplasmic signaling sequences include those derived from CD3γ, CD3δ, CD3ε, CD3ζ, CD5, CD22, CD66d, CD79a, CD79b, and common FcRγ (FCER1G), FcγRIIa, FcRβ (Fcε Rib), DAP10, and DAP12. In particular embodiments, variants of CD3ζ retain at least one, two, three, or all ITAM regions.

A co-stimulatory domain is a domain whose activation can be required for an efficient lymphocyte response to cellular marker binding. Some molecules are interchangeable as intracellular signaling components or co-stimulatory domains. Examples of costimulatory domains include CD27, CD28, 4-1BB (CD137), OX40, PD-1, ICOS, lymphocyte function-associated antigen-1 (LFA-1), NKG2C, and a ligand that specifically binds with CD83.

Transduction markers may be selected from, for example, at least one of a truncated CD19 (tCD19; see Budde et al., Blood 122: 1660, 2013); a truncated human EGFR (tEGFR; see Wang et al., Blood 118: 1255, 2011); an extracellular domain of human CD34; and/or RQR8 which combines target epitopes from CD34 (see Fehse et al, Mol. Therapy 1(5 Pt 1); 448-456, 2000) and CD20 antigens (see Philip et al, Blood 124: 1277-1278). Methods to genetically modify cells to express CAR are well-known in the art.

Recombinant receptors can additionally include tags, such as the tags described as affinity tags elsewhere herein.

(vii) Compositions and Formulations. Any of the antibodies described herein (e.g., single-domain antibodies, HcAbs, multi-domain binding molecules, antibody conjugates) in any exemplary format can be formulated alone or in combination into compositions for administration to subjects. Additionally, nucleic acids encoding the antibodies can also be formulated into compositions for administration (e.g., nucleic acids encapsulated within nanoparticles (e.g., liposomes or polymer-based nanoparticles) and/or as part of a vector delivery system (e.g., a viral vector or plasmid). Antibodies and/or nucleic acids encoding antibodies are collectively referred to herein as "active ingredients".

Salts and/or pro-drugs of the active ingredients can also be used.

A pharmaceutically acceptable salt includes any salt that retains the activity of the active ingredient and is acceptable for pharmaceutical use. A pharmaceutically acceptable salt also refers to any salt which may form in vivo as a result of administration of an acid, another salt, or a prodrug which is converted into an acid or salt.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable pharmaceutically acceptable base addition salts include metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine.

A prodrug includes an active ingredient which is converted to a therapeutically active compound after administration, such as by cleavage or by hydrolysis of a biologically labile group.

In particular embodiments, the compositions include active ingredients of at least 0.1% w/v or w/w of the composition; at least 1% w/v or w/w of composition; at least 10% w/v or w/w of composition; at least 20% w/v or w/w of composition; at least 30% w/v or w/w of composition; at least 40% w/v or w/w of composition; at least 50% w/v or w/w of composition; at least 60% w/v or w/w of composition; at least 70% w/v or w/w of composition; at least 80% w/v or w/w of composition; at least 90% w/v or w/w of composition; at least 95% w/v or w/w of composition; or at least 99% w/v or w/w of composition.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and/or trimethylamine salts.

An exemplary chelating agent is EDTA (ethylene-diamine-tetra-acetic acid).

Exemplary isotonic agents include polyhydric sugar alcohols including trihydric or higher sugar alcohols, such as glycerin, erythritol, arabitol, xylitol, sorbitol, or mannitol.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Stabilizers refer to a broad category of excipients which can range in function from a bulking agent to an additive which solubilizes the antibodies or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, a-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on therapeutic weight.

The compositions disclosed herein can be formulated for administration by, for example, injection, inhalation, infusion, perfusion, lavage, or ingestion. The compositions disclosed herein can further be formulated for intravenous, intradermal, intraarterial, intranodal, intralymphatic, intraperitoneal, intralesional, intraprostatic, intravaginal, intrarectal, topical, intrathecal, intratumoral, intramuscular, intravesicular, oral, sublingual, and/or subcutaneous administration.

For injection, compositions can be formulated as aqueous solutions, such as in buffers including Hanks' solution, Ringer's solution, or physiological saline. The aqueous solutions can include formulatory agents such as suspending, stabilizing, and/or dispersing agents. Alternatively, the composition can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid compositions such as powders, capsules and tablets, suitable excipients include binders (gum tragacanth, acacia, cornstarch, gelatin), fillers such as sugars, e.g., lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

Compositions can be formulated as an aerosol. In particular embodiments, the aerosol is provided as part of an anhydrous, liquid or dry powder inhaler. Aerosol sprays from pressurized packs or nebulizers can also be used with a suitable propellant, e.g., dichlorodifluoromethane, trichlorofluoromethane, dichlorotetrafluoroethane, carbon dioxide or other suitable gas. In the case of a pressurized aerosol, a dosage unit may be determined by providing a valve to deliver a metered amount. Capsules and cartridges of gelatin for use in an inhaler or insufflator may also be formulated including a powder mix of the composition and a suitable powder base such as lactose or starch.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salt.

Additionally, compositions can be formulated as sustained-release systems utilizing semipermeable matrices of solid polymers including at least one type of antibody. Various sustained-release materials have been established and are well known by those of ordinary skill in the art. Sustained-release systems may, depending on their chemical nature, release one or more antibodies following administration for a few weeks up to over 100 days. Depot preparations can be administered by injection; parenteral injection; instillation; or implantation into soft tissues, a body cavity, or occasionally into a blood vessel with injection through fine needles.

Depot compositions can include a variety of bioerodible polymers including poly(lactide), poly(glycolide), poly(caprolactone) and poly(lactide)-co(glycolide) (PLG) of desirable lactide:glycolide ratios, average molecular weights, polydispersities, and terminal group chemistries. Blending different polymer types in different ratios using various grades can result in characteristics that borrow from each of the contributing polymers.

The use of different solvents (for example, dichloromethane, chloroform, ethyl acetate, triacetin, N-methyl pyrrolidone, tetrahydrofuran, phenol, or combinations thereof) can alter microparticle size and structure in order to modulate release characteristics. Other useful solvents include water, ethanol, dimethyl sulfoxide (DMSO), N-methyl-2-pyrrolidone (NMP), acetone, methanol, isopropyl alcohol (IPA), ethyl benzoate, and benzyl benzoate.

Exemplary release modifiers can include surfactants, detergents, internal phase viscosity enhancers, complexing agents, surface active molecules, co-solvents, chelators, stabilizers, derivatives of cellulose, (hydroxypropyl)methyl cellulose (HPMC), HPMC acetate, cellulose acetate, pluronics (e.g., F68/F127), polysorbates, Span® (Croda Americas, Wilmington, Delaware), poly(vinyl alcohol) (PVA), Brij® (Croda Americas, Wilmington, Delaware), sucrose acetate isobutyrate (SAIB), salts, and buffers.

Excipients that partition into the external phase boundary of nanoparticles such as surfactants including polysorbates, dioctylsulfosuccinates, poloxamers, PVA, can also alter properties including particle stability and erosion rates, hydration and channel structure, interfacial transport, and kinetics in a favorable manner.

Additional processing of the disclosed sustained release depot compositions can utilize stabilizing excipients including mannitol, sucrose, trehalose, and glycine with other components such as polysorbates, PVAs, and dioctylsulfosuccinates in buffers such as Tris, citrate, or histidine. A freeze-dry cycle can also be used to produce very low moisture powders that reconstitute to similar size and performance characteristics of the original suspension.

In particular embodiments, the compositions include active ingredients of at least 0.1% w/v or w/w of the composition; at least 1% w/v or w/w of composition; at least 10% w/v or w/w of composition; at least 20% w/v or w/w of composition; at least 30% w/v or w/w of composition; at least 40% w/v or w/w of composition; at least 50% w/v or w/w of composition; at least 60% w/v or w/w of composition; at least 70% w/v or w/w of composition; at least 80% w/v or w/w of composition; at least 90% w/v or w/w of composition; at least 95% w/v or w/w of composition; or at least 99% w/v or w/w of composition.

In certain examples, cells are genetically modified to express a protein including a disclosed binding domain (as part of, for example, a recombinant receptor (e.g., CAR or eTCR)). In these embodiments, genetically modified cells can be prepared as formulations for delivery in buffers such as Hanks' solution, Ringer's solution, or physiological saline.

Therapeutically effective amounts of cells within formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

In particular embodiments, cells are in a formulation volume of a liter or less, 500 ml or less, 250 ml or less, or 100 ml or less. Hence, the density of administered cells is typically greater than $10^4$ cells/ml, $10^5$ cells/ml, $10^6$ cells/ml, $10^7$ cells/ml, or $10^8$ cells/ml.

Any composition or formulation disclosed herein can advantageously include any other pharmaceutically acceptable carriers which include those that do not produce significantly adverse, allergic, or other untoward reactions that outweigh the benefit of administration. Exemplary pharmaceutically acceptable carriers are disclosed in Remington's Pharmaceutical Sciences, 18th Ed. Mack Printing Company, 1990. Moreover, compositions and formulations can be prepared to meet sterility, pyrogenicity, general safety, and purity standards as required by U.S. FDA Office of Biological Standards and/or other relevant foreign regulatory agencies.

(viii) Methods of Use. As indicated, there are numerous uses for the single-domain antibodies disclosed herein. Certain examples include treating subjects. Subjects include, e.g., humans, veterinary animals (dogs, cats, reptiles, birds) livestock (e.g., horses, cattle, goats, pigs, chickens) and research animals (e.g., monkeys, rats, mice, fish). Treating subjects includes delivering therapeutically effective amounts. Therapeutically effective amounts include those that provide effective amounts, prophylactic treatments and/or therapeutic treatments.

An "effective amount" is the amount of a composition or formulation necessary to result in a desired physiological change in the subject. Effective amounts are often administered for research purposes. Effective amounts disclosed herein can cause a statistically-significant effect in an animal model or in vitro assay relevant to the assessment of a condition's development, progression, and/or resolution. In particular embodiments, a condition is an ROR1-related condition.

A "prophylactic treatment" includes a treatment administered to a subject who does not display signs or symptoms of a condition or displays only early signs or symptoms of a condition such that treatment is administered for the purpose of diminishing or decreasing the risk of developing the condition further. Thus, a prophylactic treatment functions as a preventative treatment against a condition. In particular embodiments, prophylactic treatments reduce, delay, or prevent the worsening of a condition.

A "therapeutic treatment" includes a treatment administered to a subject who displays symptoms or signs of a condition and is administered to the subject for the purpose of diminishing or eliminating those signs or symptoms of the condition. The therapeutic treatment can reduce, control, or eliminate the presence or activity of the condition and/or reduce control or eliminate side effects of the condition.

Function as an effective amount, prophylactic treatment, or therapeutic treatment are not mutually exclusive, and in particular embodiments, administered dosages may accomplish more than one treatment type.

In particular embodiments, therapeutically effective amounts provide anti-cancer effects. Anti-cancer effects include a decrease in the number of cancer cells, decrease in the number of metastases, prevented or reduced metastases, a decrease in tumor volume, inhibited tumor growth, an increase in life expectancy, prolonged subject life, induced chemo- or radiosensitivity in cancer cells, inhibited cancer cell proliferation, reduced cancer-associated pain, and/or reduced relapse or re-occurrence of cancer following treatment.

A "tumor" is a swelling or lesion formed by an abnormal growth of cells (called neoplastic cells or tumor cells). A "tumor cell" is an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be benign, pre-malignant or malignant.

In particular embodiments, therapeutically effective amounts induce an immune response. The immune response can be against a cancer cell, such as a ROR1-expressing cancer cell.

Exemplary ROR1-related conditions include hematological cancers such as chronic lymphocytic leukemia (CLL), hairy cell leukemia (HCL), mantle cell lymphoma (MCL), marginal zone lymphoma (MZL), diffuse large B cell lymphoma (DLBCL), follicular lymphoma (FL), multiple myeloma (MM), acute lymphocytic leukemia (ALL), acute myeloid leukemia (AML), chronic myeloid leukemia (CML), and other cancers, such as breast cancer, ovarian cancer, pancreatic cancer, lung cancer, and neuroblastoma.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including target, body weight, severity of condition, type of condition, stage of condition, previous or concurrent therapeutic interventions, idiopathy of the subject and route of administration.

Useful doses can range from 0.1 to 5 µg/kg or from 0.5 to 1 µg/kg. In other examples, a dose can include 1 µg/kg, 15 µg/kg, 30 µg/kg, 50 µg/kg, 55 µg/kg, 70 µg/kg, 90 µg/kg, 150 µg/kg, 350 µg/kg, 500 µg/kg, 750 µg/kg, 1000 µg/kg, 0.1 to 5 mg/kg or from 0.5 to 1 mg/kg. In other examples, a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

Exemplary doses of cell-based compositions can include $10^4$ to $10^9$ cells/kg body weight, or $10^3$ to $10^{11}$ cells/kg body weight. Therapeutically effective amounts to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly). In particular embodiments, the treatment protocol may be dictated by a clinical trial protocol or an FDA-approved treatment protocol.

The compositions described herein can be administered by, for example, injection, inhalation, infusion, perfusion, lavage, or ingestion. Routes of administration can include intravenous, intradermal, intraarterial, intranodal, intravesicular, intrathecal, intraperitoneal, intraparenteral, intranasal, intralesional, intramuscular, oral, subcutaneous, and/or sublingual administration. Formulations are generally be administered by injection.

Antibodies described herein can also be used for in vivo, ex vivo, or in vitro detection of ROR1-expressing cells (e.g., cancerous cells). In particular embodiments, detection is for research, diagnostic, and/or prognostic uses. In particular embodiments, methods of detection include administering an effective amount of an antibody (e.g., single-domain antibody or HcAb) disclosed herein. The antibody can be, directly or indirectly, associated with or linked to a detectable label, and the composition can be suitable for detection of an ROR1-related condition or ROR1-expressing cell.

For detection applications, the antibodies of the presently disclosed subject matter can be labeled with a detectable label. The detectable label can be any label that is capable of producing, either directly or indirectly, a detectable signal. For example, detectable labels are described elsewhere herein and include radiolabels, chemiluminescent labels, spectral colorimetric labels, affinity tags, enzymatic labels, and fluorescent labels.

The term "diagnosis", as used herein, refers to evaluation of the presence or properties of pathological states or lack thereof. With respect to objects of the present disclosure, in particular embodiments, the diagnosis is to determine the incidence of an ROR1 related condition, such as cancer.

Detection and imaging of the antibody is tunable, such that imaging can be performed in under 1, 2, 4, 6, 12, or 18, 24, 36, or 48 hours, or any amount below, above, or between this amount. It has been demonstrated that PEGs/larger molecules increase serum half-life by 2, 3, 4, 5, 6, 7, 8, 9, 10, 15, 20, 25, 30, 35, 40, 45, 50, 55, 60, 65, 70, 75, 80, 85, 90, 95, or 100%, or 2, 3, 4, 5, 6, 7, 8, 9, or 10 or more times compared to a smaller molecule. This allows for imaging at different time points.

In particular embodiments, methods of diagnosis can include administering to a subject or biological sample, a composition of antibody conjugates; detecting and quanti-fying the antibody conjugates (e.g., by detecting the detect-able label) that remains in the subject or on the biological sample, and comparing the amount of antibody conjugates to a reference level. In particular embodiments, a reference level is an amount of antibody conjugate remaining in a subject or on a biological sample with or without an ROR1-related condition.

In particular embodiments, a composition of the presently disclosed subject matter includes a label that can be detected in vivo. The term "in vivo" as used herein to describe imaging or detection methods, refers to generally non-invasive methods such as fluorescence, scintigraphic meth-ods, magnetic resonance imaging, autoradiographic detec-tion, or radioimmunoguided systems, each described briefly herein below. The term "non-invasive methods" includes methods employing administration of a contrast agent to facilitate in vivo imaging. In vivo imaging can be useful in the staging and treatment of malignancies.

In particular embodiments, methods for detecting ROR1-expressing cells in subjects includes (a) administering to the subject a composition including the antibody detectable label conjugate; and (b) detecting the detectable label to thereby detect the ROR1-expressing cells.

In particular embodiments, methods for prognosing pro-gression of a cancer in a subject includes administering an antibody detectable label conjugate to a subject under con-ditions sufficient for the antibody to bind to an ROR1 epitope present on a tumor and/or a cancer cell, if present; and identifying in the subject one or more cells that bind to the antibody, whereby progression of a cancer is prognosed in the subject.

In particular embodiments, the detectable label can be conjugated or otherwise associated with an antibody dis-closed herein or the detectable label can associate with the antibody during the methods. Following administration of the labeled composition to a subject, and after a time sufficient for binding, the biodistribution of the composition can be visualized. The term "time sufficient for binding" refers to a temporal duration that permits binding of the labeled agent to a target molecule.

Scintigraphic Imaging. Scintigraphic imaging methods include SPECT (Single Photon Emission Computed Tomog-raphy). PET (Positron Emission Tomography), gamma cam-era imaging, and rectilinear scanning. A gamma camera and a rectilinear scanner each represent instruments that detect radioactivity in a single plane. Most SPECT systems are based on the use of one or more gamma cameras that are rotated about the subject of analysis, and thus integrate radioactivity in more than one dimension. PET systems include an array of detectors in a ring that also detect radioactivity in multiple dimensions.

Imaging instruments suitable for practicing the detection and/or imaging methods of the presently disclosed subject matter, and instruction for using the same, are readily available from commercial sources. For example, a SPECT scanner can be used with a CT scanner, with coregistration of images. As in PET/CT, this allows location of tumors or tissues which may be seen on SPECT scintigraphy but are difficult to precisely locate with regard to other anatomical structures. Both PET and SPECT systems are offered by ADAC of Milpitas, Calif., United States of America, and Siemens of Hoffman Estates, Ill., United States of America. Related devices for scintigraphic imaging can also be used, such as a radio-imaging device that includes a plurality of sensors with collimating structures having a common source focus.

When scintigraphic imaging is employed, the detectable label can include a radiolabel as described elsewhere herein. When the labeling moiety is a radionuclide, stabilizers to prevent or minimize radiolytic damage, such as ascorbic acid, gentisic acid, or other appropriate antioxidants, can be added to the composition including the labeled targeting molecule.

Magnetic Resonance Imaging (MRI). Magnetic reso-nance image-based techniques create images based on the relative relaxation rates of water protons in unique chemical environments. As used herein, the term "magnetic resonance imaging" refers to magnetic source techniques including conventional magnetic resonance imaging, magnetization transfer imaging (MTI), proton magnetic resonance spec-troscopy (MRS), diffusion-weighted imaging (DWI) and functional MR imaging.

Those skilled in the art of diagnostic labeling recognize that metal ions can be bound by chelating moieties, which in turn can be conjugated to a therapeutic agent in accordance with the methods of the presently disclosed subject matter. For example, gadolinium ions are chelated by diethylenetri-aminepentaacetic acid (DTPA). Lanthanide ions are chelated by tetraazacyclododocane compounds. See U.S. Pat. Nos. 5,738,837 and 5,707,605. Alternatively, a contrast agent can be carried in a liposome.

Images derived used a magnetic source can be acquired using, for example, a superconducting quantum interference device magnetometer (SQUID, available with instruction from Quantum Design of San Diego, Calif., United States of America; see also U.S. Pat. No. 5,738,837).

Autoradiographic Detection. In the case of a radioisotope (also referred to herein as radiolabel) detection can be accomplished by conventional autoradiography or by using a phosphorimager as is known to one of skill in the art. In particular embodiments, an autoradiographic method employs photostimulable luminescence imaging plates (Fuji Medical Systems of Stamford, Conn., United States of America). Briefly, photostimulable luminescence is the quantity of light emitted from irradiated phosphorous plates following stimulation with a laser during scanning. The luminescent response of the plates is linearly proportional to the activity.

Radioimmunoguided System (RIGS). Another applica-tion of the antibodies disclosed herein is in the radioimmu-noguided surgery (RIGS) system. This technique involves the intravenous administration of a radiolabeled antibody prior to surgery. After allowing for tumor uptake and blood clearance of radioactivity, the patient is taken to the oper-ating room where surgical exploration is affected with the aid of a hand-held gamma activity probe, e.g., Neo-probe®1000 (Neoprobe Corporation, Dublin, Ohio). This helps the surgeon identify the tumor metastases and improve the complications of excision. The RIGS system is advan-tageous because it allows for the detection of tumors not otherwise detectable by visual inspection and/or palpation. See, O'Dwyer et al, Arch. Surg., 121:1 391-1394 (1986). This technique is described in detail in Hinkle et al, Anti-body, Immunoconjugates and Radiopharmacouticals, 4:(3)

339-358 (1991). This technique is useful for cancers including colon cancer, breast cancer, pancreatic cancer, and ovarian cancer.

Ex vivo Imaging. In particular embodiments, a composition as disclosed herein can be used for ex vivo imaging. In particular embodiments, ex vivo imaging methods include detecting ROR1-expressing cells by (a) contacting a biological sample derived from a subject with an antibody detectable label conjugate; and detecting the detectable label to thereby detect the ROR1-expressing cell.

In particular embodiments, methods for prognosing progression of a cancer in a subject includes isolating a biological sample including cells from a subject with a cancer; contacting the biological sample with the antibody disclosed herein under conditions sufficient for the antibody to bind to an ROR1 epitope present on a tumor and/or a cancer cell, if present, in the biological sample; and identifying in the biological sample one or more cells that bind to the antibody, whereby progression of a cancer is prognosed in the subject.

Methods may be used to monitor disease progression, for example, using biopsy samples at different times or imaging the subject at different times. In such aspects, instead of comparing the expression of ROR1 against a control sample from, e.g., a different tissue source or subject known not to have enhanced ROR1 expression, the expression of the ROR1 is compared against a biological sample obtained from the same tissue or the same subject at an earlier time point, for example, from days, weeks or months earlier.

Any suitable biological sample may be used; the nature of the disease or condition may determine the nature of the sample which is to be used in the methods. The sample may be, for example, a sample from a tissue biopsy, tumor tissue biopsy, bone marrow biopsy, or circulating cells in, e.g., blood. Alternatively, e.g., where, for example, the methods are being used to diagnose or monitor a gastrointestinal tumor, tumor cells may be isolated from feces (stool) samples. Other sources of biological sample may include plasma, serum, cerebrospinal fluid, urine, interstitial fluid, ascites fluid or the like.

For example, solid tumor samples may be collected in complete tissue culture medium with antibiotics. Cells may be manually teased from the tumor specimen or, where necessary, are enzymatically disaggregated by incubation with collagenase/DNAse and suspended in appropriate media containing, for example, human or animal sera.

In other aspects, biopsy samples may be isolated and frozen or fixed in fixatives such as formalin. The samples may then be tested for expression levels of genes at a later stage.

The antibodies of the presently disclosed subject matter can also be employed in various ex vivo assay methods, such as ELISA, Immunohistochemistry, Electron Microscopy, Latex agglutination, lateral flow immunoassays, Immuno Blotting, and Dip Stick Immuno testing, competitive binding assays, direct and indirect sandwich assays, immunoprecipitation assays (see e.g., Zola, 1987; Harlow & Lane, 1988), and as affinity purification agents.

Detection of an Affinity Tag. If an affinity tag has been used, a protein or compound that binds the affinity tag can be used to detect the affinity tag. Representative affinity tags are described elsewhere herein. In particular embodiments, a protein or compound that binds the affinity tag can be conjugated to a detectable label. In particular embodiments, a protein or compound that binds the affinity tag is conjugated to an enzymatic label. In particular embodiments, a protein or compound that binds the affinity tag is conjugated to an enzymatic label and is detected by the production of a colorimetric or luminescent product that is measurable using a spectrophotometer or luminometer, respectively.

Immunohistochemistry. Disclosed herein are methods of using immunohistochemistry (IHC) utilizing the antibody disclosed herein to detect ROR1-expressing cells. IHC detects target molecules through antigen-antibody complexes in a pathological specimen using enzyme-linked antigens or antibodies. The presence of the target molecule can then be detected via an enzyme immunoassay.

A multitude of benefits are realized with IHC versus traditional immunofluorescence. For example, unlike immunofluorescence, IHC can be used with commonly used formalin-fixed paraffin-embedded tissue specimens. Pathological specimens, including histological tissue sections and/or other biological preparations such as tissue culture cells, are commonly used in diagnostic pathology and can be easily screened via IHC. Further, IHC staining is permanent and preserves cell morphology. A comparison of the cell morphology and antigen proliferation on two different slides can be useful in monitoring the progression of a disease.

Once an antibody detectable label conjugate has been attached, either directly or indirectly, to the specimen, a substrate, specific for the enzyme, is added to the specimen. When the substrate is added, the enzyme label converts the substrate causing a color change that can be seen with light microscopy. The presence of a color change indicates the presence of the target molecule and allows an observer to determine, assess, and diagnose the disease level and severity.

Fluorescence Imaging. Non-invasive imaging methods can also include detection of a fluorescent label. Examples of fluorescent labels are described elsewhere herein. Fluorescence imaging can be performed ex vivo or in vivo. For in vivo detection of a fluorescent label, an image is created using emission and absorbance spectra that are appropriate for the particular label used. The image can be visualized, for example, by diffuse optical spectroscopy. Additional methods and imaging systems are described in U.S. Pat. Nos. 5,865,754; 6,083,486; and 6,246,901, among other places.

As used herein, the phrase "prognosing progression of a cancer" refers to evaluating indicia of a cancer disease at a given time point and comparing the same to the indicia of the cancer disease taken at an earlier time point, wherein the comparison is indicative of a progression of the cancer in the subject. In some embodiments, progression of the cancer includes metastasis of the cancer in the subject.

(ix) Reference Levels Derived from Control Populations. Obtained values for parameters associated with a therapy described herein can be compared to a reference level derived from a control population, and this comparison can indicate whether a therapy described herein is effective for a subject in need thereof. Reference levels can be obtained from one or more relevant datasets from a control population. A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual data points; e.g., mean, median, median of the mean, etc. Alternatively, a reference level or dataset to create a reference level can be obtained from a service provider such as a laboratory, or from a database or a server on which the dataset has been stored.

A reference level from a dataset can be derived from previous measures derived from a control population. A "control population" is any grouping of subjects or samples of like specified characteristics. The grouping could be according to, for example, clinical parameters, clinical assessments, therapeutic regimens, disease status, severity of condition, etc. In particular embodiments, the grouping is based on age range (e.g., 60-65 years) and cancer status. In particular embodiments, a normal control population includes individuals that are age-matched to a test subject and do not have cancer. In particular embodiments, age-matched includes, e.g., 0-10 years old; 30-40 years old, 60-65 years old, 70-85 years old, etc., as is clinically relevant under the circumstances. In particular embodiments, a control population can include those that have a ROR1-related condition and have not been administered a therapeutically effective amount In particular embodiments, the relevant reference level for values of a particular parameter associated with a therapy described herein is obtained based on the value of a particular corresponding parameter associated with a therapy in a control population to determine whether a therapy disclosed herein has been therapeutically effective for a subject in need thereof.

In particular embodiments, conclusions are drawn based on whether a sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. An example of a commonly used measure of statistical significance is the p-value. The p-value represents the probability of obtaining a given result equivalent to a particular data point, where the data point is the result of random chance alone. A result is often considered significant (not random chance) at a p-value less than or equal to 0.05. In particular embodiments, a sample value is "comparable to" a reference level derived from a normal control population if the sample value and the reference level are not statistically significantly different.

(x) Kits. Also provided herein are kits including at least one single-domain antibody disclosed herein. Kits may be formed with components to practice, for example, the methods described herein. In particular embodiments, the kit includes a single-domain antibody, an HcAb, a multidomain binding molecule, or an antibody conjugate as described herein. In particular embodiments, the kit includes cells expressing CAR or eTCR or compositions to modify cells to express CAR or eTCR. The kit may include material(s), which may be desirable from a user standpoint, such as a buffer(s), a diluent(s), a standard(s), and/or other material useful in sample processing, washing, or conducting any other step of the method described herein.

In particular embodiments, a kit includes a first multi-domain binding molecule and a second multi-domain binding molecule. In particular embodiments, the first multi-domain binding molecule includes an antibody including a first binding domain including an anti-ROR1 single-domain antibody and a second binding domain including an anti-CD3 scFv. In particular embodiments, the second multi-domain binding molecule includes a bispecific antibody. In particular embodiments, the bispecific antibody includes a first binding domain that binds CD19 and a second binding domain that binds CD28. In particular embodiments, the bispecific antibody includes a first binding domain including an anti-CD19 scFv and a second binding domain including an anti-CD28 scFv.

In particular embodiments, a kit includes an antibody conjugate and any other materials needed for treatment, imaging, or diagnosis of ROR1-related conditions.

The kit according to the present disclosure may also include instructions for carrying out the method. Instructions included in the kit of the present disclosure may be affixed to packaging material or may be included as a package insert. While instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site which provides instructions.

(xi) Exemplary Embodiments. The Exemplary Embodiments below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

1. A single-domain antibody that binds receptor tyrosine kinase (ROR1), the single domain antibody including a set of complementarity determining regions (CDRs) including:

(i) a CDR1 having the sequence as set forth in SEQ ID NO: 6, a CDR2 having the sequence as set forth in SEQ ID NO: 7, and a CDR3 having the sequence as set forth in SEQ ID NO: 8 according to IMGT;

(ii) a CDR1 having the sequence as set forth in SEQ ID NO: 9, a CDR2 having the sequence as set forth in SEQ ID NO: 10, and a CDR3 having the sequence as set forth in SEQ ID NO: 11 according to Kabat;

(iii) a CDR1 having the sequence as set forth in SEQ ID NO: 12, a CDR2 having the sequence as set forth in SEQ ID NO: 13, and a CDR3 having the sequence as set forth in SEQ ID NO: 11 according to Chothia;

(iv) a CDR1 having the sequence as set forth in SEQ ID NO: 14, a CDR2 having the sequence as set forth in SEQ ID NO: 15, and a CDR3 having the sequence as set forth in SEQ ID NO: 8 according to North;

(v) a CDR1 having the sequence as set forth in SEQ ID NO: 16, a CDR2 having the sequence as set forth in SEQ ID NO: 17, and a CDR3 having the sequence as set forth in SEQ ID NO: 18 according to Contact;

(vi) a CDR1 having the sequence as set forth in SEQ ID NO: 19, a CDR2 having the sequence as set forth in SEQ ID NO: 20, and a CDR3 having the sequence as set forth in SEQ ID NO: 21 according to IMGT;

(vii) a CDR1 having the sequence as set forth in SEQ ID NO: 22, a CDR2 having the sequence as set forth in SEQ ID NO: 23, and a CDR3 having the sequence as set forth in SEQ ID NO: 24 according to Kabat;

(viii) a CDR1 having the sequence as set forth in SEQ ID NO: 25, a CDR2 having the sequence as set forth in SEQ ID NO: 26, and a CDR3 having the sequence as set forth in SEQ ID NO: 24 according to Chothia;

(ix) a CDR1 having the sequence as set forth in SEQ ID NO: 27, a CDR2 having the sequence as set forth in SEQ ID NO: 28, and a CDR3 having the sequence as set forth in SEQ ID NO: 21 according to North;

(x) a CDR1 having the sequence as set forth in SEQ ID NO: 29, a CDR2 having the sequence as set forth in SEQ ID NO: 30, and a CDR3 having the sequence as set forth in SEQ ID NO: 31 according to Contact;

(xi) a CDR1 having the sequence as set forth in SEQ ID NO: 32, a CDR2 having the sequence as set forth in SEQ ID NO: 20, and a CDR3 having the sequence as set forth in SEQ ID NO: 33 according to IMGT;

(xii) a CDR1 having the sequence as set forth in SEQ ID NO: 34, a CDR2 having the sequence as set forth in SEQ ID NO: 23, and a CDR3 having the sequence as set forth in SEQ ID NO: 24 according to Kabat;

(xiii) a CDR1 having the sequence as set forth in SEQ ID NO: 35, a CDR2 having the sequence as set forth in SEQ ID NO: 26, and a CDR3 having the sequence as set forth in SEQ ID NO: 33 according to Chothia;

(xiv) a CDR1 having the sequence as set forth in SEQ ID NO: 36, a CDR2 having the sequence as set forth in SEQ ID NO: 28, and a CDR3 having the sequence as set forth in SEQ ID NO: 33 according to North;

(xv) a CDR1 having the sequence as set forth in SEQ ID NO: 29, a CDR2 having the sequence as set forth in SEQ ID NO: 30, and a CDR3 having the sequence as set forth in SEQ ID NO: 37 according to Contact;

(xvi) a CDR1 having the sequence as set forth in SEQ ID NO: 32, a CDR2 having the sequence as set forth in SEQ ID NO: 20, and a CDR3 having the sequence as set forth in SEQ ID NO: 21 according to IMGT;

(xvii) a CDR1 having the sequence as set forth in SEQ ID NO: 35, a CDR2 having the sequence as set forth in SEQ ID NO: 26, and a CDR3 having the sequence as set forth in SEQ ID NO: 24 according to Chothia; or (xviii) a CDR1 having the sequence as set forth in SEQ ID NO: 36, a CDR2 having the sequence as set forth in SEQ ID NO: 28, and a CDR3 having the sequence as set forth in SEQ ID NO: 21 according to North wherein the single-domain antibody is not linked to an IgM Fc region or multimerizing fragment thereof.

2. The single-domain antibody of claim 1, wherein the single-domain antibody includes a sequence having at least 90% sequence identity to a sequence as set forth in SEQ ID NO: 1, SEQ ID NO: 2, SEQ ID NO: 3, SEQ ID NO: 4, or SEQ ID NO: 5.

3. The single-domain antibody of claim 1, wherein the single-domain antibody includes the sequence as set forth in SEQ ID NO: 1, SEQ ID NO: 2, SEQ ID NO: 3, SEQ ID NO: 4, or SEQ ID NO: 5.

4. A heavy chain only antibody (HcAb) including the single-domain antibody of any of embodiments 1-3 linked to an IgG, IgA, IgD, or IgE Fc region of an antibody.

5. The HcAb of embodiment 4, wherein the Fc region includes a multimerizing fragment of the IgA Fc region.

6. The HcAb of embodiment 5, wherein the multimerizing fragment of the IgA Fc region includes the IgA tailpiece.

7. The HcAb of any of embodiments 4-6, wherein the Fc region includes an IgG Fc region and a multimerizing fragment of the IgA Fc region.

8. The HcAb of embodiment 7, wherein the IgG is IgG1, IgG2, IgG3 or IgG4.

9. The HcAb of any of embodiments 4-8, including a J-chain.

10. The HcAb of embodiment 9, wherein the binding domain is introduced into the J-chain.

11. The HcAb of any of embodiments 4-10, formatted into a multimer.

12. The HcAb of embodiment 11, wherein the multimer is an IgA multimer, or an IgG multimer.

13. The HcAb of embodiment 12, wherein the multimer is an IgA dimer.

14. The HcAb of any of embodiments 4-13, wherein the Fc region includes a modification to produce an administration benefit.

15. The HcAb of embodiment 14, wherein the administration benefit includes reduced susceptibility to proteolysis, reduced susceptibility to oxidation, altered binding affinity for forming protein complexes, altered binding affinities, reduced immunogenicity, and/or extended half-life.

16. A multi-domain binding molecule including at least two binding domains wherein at least one binding domain includes a single-domain antibody of any of embodiments 1-3 or an HcAb of any of embodiments 4-15 and wherein the multi-domain binding molecule does not include an IgM Fc region or multimerizing fragment thereof.

17. The multi-domain binding molecule of embodiment 16, wherein the multi-domain binding molecule includes a CD19 binding domain.

18. The multi-domain binding molecule of embodiment 17, wherein the CD19 binding domain includes an anti-CD19 scFv.

19. The multi-domain binding molecule of embodiments 17 or 18, wherein the CD19 binding domain includes a variable heavy chain sequencing including a CDRH1 having the sequence as set forth in SEQ ID NO: 66, a CDRH2 having the sequence as set forth in SEQ ID NO: 67, and a CDRH3 having the sequence as set forth in SEQ ID NO: 68; and a variable light chain sequence including a CDRL1 having the sequence as set forth in SEQ ID NO: 63, a CDRL2 having the sequence as set forth in SEQ ID NO: 64, and a CDRL3 having the sequence as set forth in SEQ ID NO: 65; or a variable heavy chain sequence including a CDRH1 having the sequence as set forth in SEQ ID NO: 72, a CDRH2 having the sequence as set forth in SEQ ID NO: 73, and a CDRH3 having the sequence as set forth in SEQ ID NO: 74; and a variable light chain sequence including a CDRL1 having the sequence as set forth in SEQ ID NO: 69, a CDRL2 having the sequence as set forth in SEQ ID NO: 70, and a CDRL3 having the sequence as set forth in SEQ ID NO: 71.

20. The multi-domain binding molecule of any of embodiments 16-19, wherein the multi-domain binding molecule includes an immune cell engaging molecule.

21. The multi-domain binding molecule of embodiment 20, wherein the immune cell engaging molecule activates a B cell, T cell, natural killer (NK) cell, or macrophage.

22. The multi-domain binding molecule of embodiment 21, wherein the T cell is a CD3 T cell, a CD4 T cell, a CD8 T cell, a central memory T cell, an effector memory T cell, and/or a naïve T cell.

23. The multi-domain binding molecule of any of embodiments 20-22, wherein a binding domain of the immune cell engaging molecule binds CD3, CD28, CD8, NKG2D, CD8, CD16, KIR2DL4, KIR2DS1, KIR2DS2, KIR3DS1, NKG2C, NKG2E, NKG2D, NKp30, NKp44, NKp46, NKp80, DNAM-1, CD11b, CD11c, CD64, CD68, CD119, CD163, CD206, CD209, F4/80, IFGR2, Toll-like receptors 1-9, IL-4Rα, or MARCO.

24. The multi-domain binding molecule of any of embodiments 20-23, wherein a binding domain of the immune cell engaging molecule binds CD3.

25. The multi-domain binding molecule of embodiment 24, wherein immune cell engaging molecule that binds CD3 is derived from the OKT3 antibody.

26. The multi-domain binding molecule of embodiments 24 or 25, wherein the binding domain that binds CD3 has a variable heavy chain sequence including a CDRH1 having the sequence as set forth in SEQ ID NO: 82, a CDRH2 having the sequence as set forth in SEQ ID NO: 83, and a CDRH3 having the sequence as set forth in SEQ ID NO: 84; and a variable light chain sequence including a CDRL1 having the sequence as set forth in SEQ ID NO: 79, a CDRL2 having the sequence as set forth in SEQ ID NO: 80, and a CDRL3 having the sequence as set forth in SEQ ID NO: 81.

27. The multi-domain binding molecule of any of embodiments 20-23, wherein a binding domain of the immune cell engaging molecule binds CD28.

28. The multi-domain binding molecule of embodiment 27, wherein immune cell engaging molecule that binds CD28 is derived from the TGN1412 antibody.

29. The multi-domain binding molecule of any of embodiments 16-28, wherein the single-domain antibody of any of embodiments 1-3 is linked to a first Fc region of the multi-domain binding molecule and a binding domain that binds CD3 is linked to a second Fc region of the multi-domain binding molecule.

30. A conjugate including a single-domain antibody of any of embodiments 1-3 or an HcAb of any of embodiments 4-15 linked to an immunotoxin, a drug, a detectable label, a radioisotope, or a particle.

31. The conjugate of embodiment 30, wherein the immunotoxin includes a plant toxin or bacterial toxin.

32. The conjugate of embodiment 31, wherein the plant toxin includes ricin, abrin, mistletoe lectin, modeccin, pokeweed antiviral protein, saporin, Bryodin 1, bouganin, or gelonin.

33. The conjugate of embodiment 31, wherein the bacterial toxin includes diphtheria toxin or *Pseudomonas* exotoxin.

34. The conjugate of embodiment 30, wherein the drug includes a cytotoxic drug.

35. The conjugate of embodiment 34, wherein the cytotoxic drug includes actinomycin D, anthracycline, auristatin, calicheamicin, camptothecin, CC1065, colchicin, cytochalasin B, daunorubicin, 1-dehydrotestosterone, dihydroxy anthracinedione, dolastatin, doxorubicin, duocarmycin, elinafide, emetine, ethidium bromide, etoposide, gramicidin D, glucocorticoids, lidocaine, maytansinoid, mithramycin, mitomycin, mitoxantrone, nemorubicin, PNU-159682, procaine, propranolol, puromycin, pyrrolobenzodiazepine, taxane, taxol, tenoposide, tetracaine, trichothecene, vinblastine, vinca alkaloid, or vincristine.

36. The conjugate of embodiments 30, wherein the radioisotope includes $^{228}$Ac, $^{111}$Ag, $^{124}$Am, $^{74}$As, $^{211}$At, $^{209}$At, $^{194}$Au, $^{128}$Ba, $^{7}$Be, $^{206}$Bi, $^{245}$Bk, $^{246}$Bk, $^{76}$Br, $^{11}$C, $^{14}$C, $^{47}$Ca, $^{254}$Cf, $^{242}$Cm, $^{51}$Cr, $^{67}$Cu, $^{153}$Dy, $^{157}$Dy, $^{159}$Dy $^{165}$Dy, $^{166}$Dy $^{171}$Er, $^{250}$Es, $^{254}$Es, $^{147}$Eu, $^{157}$Eu, $^{52}$Fe, $^{59}$Fe, $^{251}$Fm, $^{252}$Fm, $^{253}$Fm, $^{66}$Ga, $^{72}$Ga, $^{146}$Gd, $^{153}$Gd, $^{68}$Ge, $^{3}$H, $^{170}$Hf, $^{171}$Hf, $^{193}$Hg, $^{193}$mHg, $^{160}$mHo, $^{130}$I, $^{131}$I, $^{135}$I, $^{114}$mIn, $^{185}$Ir, $^{42}$K, $^{43}$K, $^{76}$Kr, $^{79}$Kr, $^{81}$mKr, $^{132}$La, $^{262}$Lr, $^{169}$Lu, $^{174}$mLu, $^{176}$mLu, $^{257}$Md, $^{260}$Md, $^{28}$Mg, $^{52}$Mn, $^{90}$Mo, $^{24}$Na, $^{95}$Nb, $^{138}$Nd, $^{57}$Ni, $^{66}$Ni, $^{234}$Np, $^{15}$O, $^{182}$Os, $^{189}$mOs, $^{191}$Os, $^{32}$P, $^{201}$Pb, $^{101}$Pd, $^{143}$Pr, $^{191}$Pt, $^{243}$Pu, $^{225}$Ra, $^{81}$Rb, $^{188}$Re, $^{105}$Rh, $^{211}$Rn, $^{103}$Ru, $^{35}$S, $^{44}$Sc, $^{72}$Se, $^{153}$Sm, $^{125}$Sn, $^{91}$Sr, $^{173}$Ta, $^{154}$Tb, $^{127}$Te, $^{234}$Th, $^{45}$Ti, $^{166}$Tm, $^{230}$U, $^{237}$U, $^{240}$U, $^{48}$V, $^{178}$W, $^{181}$W, $^{188}$W, $^{125}$Xe, $^{127}$Xe, $^{133}$Xe, $^{133}$mXe, $^{135}$Xe, $^{85}$mY, $^{86}$Y, $^{90}$Y, $^{93}$Y, $^{169}$Yb, $^{175}$Yb, $^{65}$Zn, $^{71}$mZn, $^{86}$Zr, $^{95}$Zr, or $^{97}$Zr.

37. The conjugate of any of embodiments 30-36, wherein the single-domain antibody is linked to the radioisotope through siderocalin (Scn).

38. The conjugate of embodiment 37, wherein the Scn is human Scn.

39. The conjugate of embodiment 30, wherein the detectable label includes a chemiluminescent label, a spectral colorimetric label, an affinity tag, an enzymatic label, a fluorescent label, or a contrast agent.

40. The conjugate of embodiment 39, wherein the chemiluminescent label includes lucigenin, luminol, luciferin, isoluminol, theromatic acridinium ester, imidazole, acridinium salt, or oxalate ester.

41. The conjugate of embodiment 39, wherein the spectral colorimetric label includes colloidal gold.

42. The conjugate of embodiment 39, wherein the affinity tag includes a tag with a sequence as set forth in SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, or SEQ ID NO: 110.

43. The conjugate of embodiment 39, wherein the enzymatic label includes malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase, or acetylcholinesterase.

44. The conjugate of embodiment 39, wherein the fluorescent label includes blue fluorescent protein, cyan fluorescent protein, green fluorescent protein, luciferase, orange fluorescent protein, red fluorescent protein, far red fluorescent protein, or yellow fluorescent protein.

45. A chimeric antigen receptor (CAR) that, when expressed by a cell, includes an extracellular component linked to an intracellular component by a transmembrane domain, wherein the extracellular component includes a single-domain antibody of embodiments 1-3.

46. The CAR of embodiment 45, wherein the intracellular component includes an effector domain including: 4-1BB (CD137), CD3γ, CD3δ, CD3ε, CD3ζ, CD27, CD28, DAP10, ICOS, LAG3, NKG2D, NOTCH1, OX40, ROR2, SLAMF1, TCRα, TCRβ, TRIM, Wnt, Zap70, or a combination thereof.

47. The CAR of embodiments 45 or 46, wherein the transmembrane domain includes a transmembrane region of: the α, β or ζ chain of a T-cell receptor; CD28; CD27; CD3; CD45; CD4; CD5; CD8; CD9; CD16; CD22; CD33; CD37; CD64; CD80; CD86; CD134; CD137; CD154; or a combination thereof.

48. The CAR of any of embodiments 45-47, wherein the CAR further includes a spacer region.

49. An engineered T cell receptor (eTCR) including a constant alpha domain ($C_\alpha$), a constant beta domain ($C_\beta$), and a single-domain antibody of any of embodiments 1-3 linked to the Ca domain and/or the $C_\beta$ domain.

50. The eTCR of embodiment 49, wherein the single-domain antibody of any of embodiments 1-3 is linked to the Ca domain.

51. The eTCR of embodiments 49 or 50, wherein the single-domain antibody of any of embodiments 1-3 is linked to the $C_\beta$ domain.

52. The eTCR of any of embodiments 49-51, wherein one single-domain antibody of any of embodiments 1-3 is linked to the $C_\alpha$ domain and one single-domain antibody of any of embodiments 1-3 is linked to the $C_\beta$ domain.

53. A cell genetically modified to express the single-domain antibody of embo any of embodiments diment 1-3, the HcAb of any of embodiments 4-15, the CAR of any of embodiments 45-48 or the eTCR of any of embodiments 49-52.

54. The cell of embodiment 53, wherein the cell is an immune cell.

55. The cell of embodiment 54, wherein the immune cell is a T cell, B cell, natural killer cell, or macrophage.

56. A composition including the single-domain antibody of any of embodiments 1-3 or the HcAb of any of embodiments 4-15 and a pharmaceutically acceptable carrier.

57. A formulation including the cell of any of embodiments 53-55 and a pharmaceutically acceptable carrier.

58. A kit including a multi-domain binding molecule of any of embodiments 16-29 and a bispecific antibody.

59. The kit of embodiment 58, wherein the bispecific antibody includes a first scFv linked to a second scFv.

60. The kit of embodiment 59, wherein the first scFv includes an anti-CD19 scFv.

61. The kit of embodiment 60, wherein the anti-CD19 scFv includes a variable heavy chain sequencing including a CDRH1 having the sequence as set forth in SEQ ID NO: 66, a CDRH2 having the sequence as set forth in SEQ ID NO: 67, and a CDRH3 having the sequence as set forth in SEQ ID NO: 68; and a variable light chain sequence including a CDRL1 having the sequence as set forth in SEQ ID NO: 63, a CDRL2 having the sequence as set forth in SEQ ID NO: 64, and a CDRL3 having the sequence as set forth in SEQ ID NO: 65; or a variable heavy chain sequencing including a CDRH1 having the sequence as set forth in SEQ ID NO: 72, a CDRH2 having the sequence as set forth in SEQ ID NO: 73, and a CDRH3 having the sequence as set forth in SEQ ID NO: 74; and a variable light chain sequence including a CDRL1 having the sequence as set forth in SEQ ID NO: 69, a CDRL2 having the sequence as set forth in SEQ ID NO: 70, and a CDRL3 having the sequence as set forth in SEQ ID NO: 71.

62. The kit of any of embodiments 59-61, wherein the second scFv includes an anti-CD28 scFv.

63. The kit of embodiment 62, wherein the anti-CD28 scFv includes a variable heavy chain sequencing including a CDRH1 having the sequence as set forth in SEQ ID NO: 90, a CDRH2 having the sequence as set forth in SEQ ID NO: 91, and a CDRH3 having the sequence as set forth in SEQ ID NO: 92; and a variable light chain sequence including a CDRL1 having the sequence as set forth in SEQ ID NO: 87, a CDRL2 having the sequence as set forth in SEQ ID NO: 88, and a CDRL3 having the sequence as set forth in SEQ ID NO: 89.

64. The kit of any of embodiments 58-63, wherein the multi-domain binding molecule includes an IgG Fc region linked to a first binding domain and a second binding domain.

65. The kit of embodiment 64, wherein the first binding domain includes the single-domain antibody of any of embodiments 1-3.

66. The kit of embodiments 64 or 65, wherein the second binding domain includes an anti-CD3 scFv.

67. The kit of embodiment 66, wherein the anti-CD3 scFv includes a variable heavy chain sequencing including a CDRH1 having the sequence as set forth in SEQ ID NO: 82, a CDRH2 having the sequence as set forth in SEQ ID NO: 83, and a CDRH3 having the sequence as set forth in SEQ ID NO: 84; and a variable light chain sequence including a CDRL1 having the sequence as set forth in SEQ ID NO: 79, a CDRL2 having the sequence as set forth in SEQ ID NO: 80, and a CDRL3 having the sequence as set forth in SEQ ID NO: 81.

68. A method of treating a subject in need thereof including administering a therapeutically effective amount of the composition of embodiment 56 and/or the formulation of embodiment 57 thereby treating the subject in need thereof.

69. The method of embodiment 68, wherein the therapeutically effective amount provides a prophylactic or a therapeutic treatment against an ROR1-related condition.

70. The method of embodiment 69, wherein the ROR1-related condition is cancer.

71. The method of embodiment 70, wherein the cancer includes chronic lymphocytic leukemia (CLL), hairy cell leukemia (HCL), mantle cell lymphoma (MCL), marginal zone lymphoma (MZL), diffuse large B cell lymphoma (DLBCL), follicular lymphoma (FL), multiple myeloma (MM), acute lymphocytic leukemia (ALL), acute myeloid leukemia (AML), chronic myeloid leukemia (CML), breast cancer, ovarian cancer, pancreatic cancer, lung cancer, or neuroblastoma.

72. The method of any of embodiments 68-71, wherein the administering is through intravenous, intradermal, intraarterial, intranodal, intravesicular, intrathecal, intraperitoneal, intraparenteral, intranasal, intralesional, intramuscular, oral, intrapulmonary, subcutaneous, or sublingual administering.

73. A method of detecting ROR1-expressing cells including administering to a subject or a biological sample derived from the subject a conjugate of any of embodiments 30-44 and detecting the detectable label.

74. The method of embodiment 73, wherein the detecting includes imaging.

75. The method of embodiment 74, further including diagnosing the subject based on the detecting.

76. The method of embodiment 75, wherein the diagnosing includes determining the level of expression of the ROR1 based on a signal from the detectable label and comparing the level of expression of the detectable label to a reference level.

77. The method of embodiment 76, wherein the reference level is the level of the signal from a tissue without an ROR1-related condition.

78. The method of embodiment 76, wherein the reference level is the level of the signal from the subject or the biological sample derived from the subject at a different time point.

79. The method of any of embodiments 73-78, wherein the biological sample derived from the subject includes a tissue biopsy, a tumor tissue biopsy, blood, bone marrow biopsy, or stool from the subject.

(xii) Closing Paragraphs. The nucleic acid and amino acid sequences provided herein are shown using letter abbreviations for nucleotide bases and amino acid residues, as defined in 37 C.F.R. § 1.831-1.835 and set forth in WIPO Standard ST.26 (implemented on Jul. 1, 2022). Only one strand of each nucleic acid sequence is shown, but the complementary strand is understood as included in embodiments where it would be appropriate.

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in nonessential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (lie), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, lie, Phe, Met, and Trp; Group 11 (aliphatic): Gly, Ala, Val, Leu, and lie; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3);

Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like. As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridize under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH2PO4; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

"Specifically binds" refers to an association of a binding domain (of, for example, a single-domain antibody) to its cognate binding molecule with an affinity or $K_a$ (i.e., an equilibrium association constant of a particular binding interaction with units of 1/M) equal to or greater than $10^5$ $M^{-1}$, while not significantly associating with any other molecules or components in a relevant environment sample. Binding domains may be classified as "high affinity" or "low affinity". In particular embodiments, "high affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. In particular embodiments, "low affinity" binding domains refer to those binding domains with a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domains with stronger binding to a cognate binding molecule than a wild type (or parent) binding domain. For example, enhanced affinity may be due to a $K_a$ (equilibrium association constant) for the cognate binding molecule that is higher than the reference binding domain or due to a $K_d$ (dissociation constant) for the cognate binding molecule that is less than that of the reference binding domain, or due to an off-rate ($K_{off}$) for the cognate binding molecule that is less than that of the reference binding domain. A variety of assays are known for detecting binding domains that specifically bind a particular cognate binding molecule as well as determining binding affinities, such as Western blot, ELISA, and BIACORE® analysis (see also, e.g., Scatchard, et al., 1949, Ann. N. Y. Acad. Sci. 51:660; and U.S. Pat. Nos. 5,283,173, 5,468,614, or the equivalent).

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant increase in ROR1-expressing cells.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. A single-domain antibody that binds receptor tyrosine kinase (ROR1), the single domain antibody comprising a set of complementarity determining regions (CDRs) comprising:

(i) a CDR1 having the sequence as set forth in SEQ ID NO: 6, a CDR2 having the sequence as set forth in SEQ ID NO: 7, and a CDR3 having the sequence as set forth in SEQ ID NO: 8 according to IMGT;

(ii) a CDR1 having the sequence as set forth in SEQ ID NO: 9, a CDR2 having the sequence as set forth in SEQ ID NO: 10, and a CDR3 having the sequence as set forth in SEQ ID NO: 11 according to Kabat;

(iii) a CDR1 having the sequence as set forth in SEQ ID NO: 12, a CDR2 having the sequence as set forth in SEQ ID NO: 13, and a CDR3 having the sequence as set forth in SEQ ID NO: 11 according to Chothia;

(iv) a CDR1 having the sequence as set forth in SEQ ID NO: 14, a CDR2 having the sequence as set forth in SEQ ID NO: 15, and a CDR3 having the sequence as set forth in SEQ ID NO: 8 according to North;

(v) a CDR1 having the sequence as set forth in SEQ ID NO: 16, a CDR2 having the sequence as set forth in SEQ ID NO: 17, and a CDR3 having the sequence as set forth in SEQ ID NO: 18 according to Contact;

(vi) a CDR1 having the sequence as set forth in SEQ ID NO: 19, a CDR2 having the sequence as set forth in SEQ ID NO: 20, and a CDR3 having the sequence as set forth in SEQ ID NO: 21 according to IMGT;

(vii) a CDR1 having the sequence as set forth in SEQ ID NO: 22, a CDR2 having the sequence as set forth in SEQ ID NO: 23, and a CDR3 having the sequence as set forth in SEQ ID NO: 24 according to Kabat;

(viii) a CDR1 having the sequence as set forth in SEQ ID NO: 25, a CDR2 having the sequence as set forth in SEQ ID NO: 26, and a CDR3 having the sequence as set forth in SEQ ID NO: 24 according to Chothia;

(ix) a CDR1 having the sequence as set forth in SEQ ID NO: 27, a CDR2 having the sequence as set forth in SEQ ID NO: 28, and a CDR3 having the sequence as set forth in SEQ ID NO: 21 according to North;

(x) a CDR1 having the sequence as set forth in SEQ ID NO: 29, a CDR2 having the sequence as set forth in SEQ ID NO: 30, and a CDR3 having the sequence as set forth in SEQ ID NO: 31 according to Contact;

(xi) a CDR1 having the sequence as set forth in SEQ ID NO: 32, a CDR2 having the sequence as set forth in SEQ ID NO: 20, and a CDR3 having the sequence as set forth in SEQ ID NO: 33 according to IMGT;

(xii) a CDR1 having the sequence as set forth in SEQ ID NO: 34, a CDR2 having the sequence as set forth in SEQ ID NO: 23, and a CDR3 having the sequence as set forth in SEQ ID NO: 24 according to Kabat;

(xiii) a CDR1 having the sequence as set forth in SEQ ID NO: 35, a CDR2 having the sequence as set forth in SEQ ID NO: 26, and a CDR3 having the sequence as set forth in SEQ ID NO: 33 according to Chothia;

(xiv) a CDR1 having the sequence as set forth in SEQ ID NO: 36, a CDR2 having the sequence as set forth in SEQ ID NO: 28, and a CDR3 having the sequence as set forth in SEQ ID NO: 33 according to North;

(XV) a CDR1 having the sequence as set forth in SEQ ID NO: 29, a CDR2 having the sequence as set forth in SEQ ID NO: 30, and a CDR3 having the sequence as set forth in SEQ ID NO: 37 according to Contact;

(xvi) a CDR1 having the sequence as set forth in SEQ ID NO: 32, a CDR2 having the sequence as set forth in SEQ ID NO: 20, and a CDR3 having the sequence as set forth in SEQ ID NO: 21 according to IMGT;

(xvii) a CDR1 having the sequence as set forth in SEQ ID NO: 35, a CDR2 having the sequence as set forth in SEQ ID NO: 26, and a CDR3 having the sequence as set forth in SEQ ID NO: 24 according to Chothia; or (xviii) a CDR1 having the sequence as set forth in SEQ ID NO: 36, a CDR2 having the sequence as set forth in SEQ ID NO: 28, and a CDR3 having the sequence as set forth in SEQ ID NO: 21 according to North wherein the single-domain antibody is not linked to an IgM Fc region or multimerizing fragment thereof.

2. The single-domain antibody of claim 1, wherein the single-domain antibody comprises a sequence having at least 90% sequence identity to the sequence as set forth in SEQ ID NO: 1, SEQ ID NO: 2, SEQ ID NO: 3, SEQ ID NO: 4, or SEQ ID NO: 5.

3. The single-domain antibody of claim 1, wherein the single-domain antibody comprises the sequence as set forth in SEQ ID NO: 1, SEQ ID NO: 2, SEQ ID NO: 3, SEQ ID NO: 4, or SEQ ID NO: 5.

4. A heavy chain only antibody (HcAb) comprising the single-domain antibody of claim 1 linked to an IgG, IgA, IgD, or IgE Fc region of an antibody.

5. A multi-domain binding molecule comprising at least two binding domains wherein at least one binding domain comprises a single-domain antibody of claim 1 and wherein the multi-domain binding molecule does not comprise an IgM Fc region or multimerizing fragment thereof.

6. The multi-domain binding molecule of claim 5, wherein the multi-domain binding molecule comprises a CD19 binding domain.

7. The multi-domain binding molecule of claim 6, wherein the CD19 binding domain comprises an anti-CD19 scFv.

8. The multi-domain binding molecule of claim 6, wherein the CD19 binding domain comprises a variable heavy chain sequencing comprising a CDRH1 having the sequence as set forth in SEQ ID NO: 66, a CDRH2 having the sequence as set forth in SEQ ID NO: 67, and a CDRH3 having the sequence as set forth in SEQ ID NO: 68; and a variable light chain sequence comprising a CDRL1 having the sequence as set forth in SEQ ID NO: 63, a CDRL2 having the sequence as set forth in SEQ ID NO: 64, and a CDRL3 having the sequence as set forth in SEQ ID NO: 65; or a variable heavy chain sequence comprising a CDRH1 having the sequence as set forth in SEQ ID NO: 72, a CDRH2 having the sequence as set forth in SEQ ID NO: 73, and a CDRH3 having the sequence as set forth in SEQ ID NO: 74; and a variable light chain sequence comprising a CDRL1 having the sequence as set forth in SEQ ID NO: 69, a CDRL2 having the sequence as set forth in SEQ ID NO: 70, and a CDRL3 having the sequence as set forth in SEQ ID NO: 71.

9. The multi-domain binding molecule of claim 5, wherein the multi-domain binding molecule comprises an immune cell engaging molecule.

10. The multi-domain binding molecule of claim 9, wherein the immune cell engaging molecule activates a B cell, T cell, natural killer (NK) cell, or macrophage.

11. The multi-domain binding molecule of claim 10, wherein the T cell is a CD3 T cell, a CD4 T cell, a CD8 T cell, a central memory T cell, an effector memory T cell, and/or a naïve T cell.

12. The multi-domain binding molecule of claim 9, wherein a binding domain of the immune cell engaging molecule binds CD3, CD28, CD8, NKG2D, CD8, CD16, KIR2DL4, KIR2DS1, KIR2DS2, KIR3DS1, NKG2C, NKG2E, NKG2D, NKp30, NKp44, NKp46, NKp80, DNAM-1, CD11b, CD11c, CD64, CD68, CD119, CD163, CD206, CD209, F4/80, IFGR2, Toll-like receptors 1-9, IL-4Rα, or MARCO.

13. The multi-domain binding molecule of claim 9, wherein a binding domain of the immune cell engaging molecule binds CD3.

14. The multi-domain binding molecule of claim 13, wherein the CD3 binding domain is derived from the OKT3 antibody.

15. The multi-domain binding molecule of claim 13, wherein the binding domain that binds CD3 has a variable heavy chain sequence comprising a CDRH1 having the sequence as set forth in SEQ ID NO: 82, a CDRH2 having the sequence as set forth in SEQ ID NO: 83, and a CDRH3 having the sequence as set forth in SEQ ID NO: 84; and a variable light chain sequence comprising a CDRL1 having the sequence as set forth in SEQ ID NO: 79, a CDRL2 having the sequence as set forth in SEQ ID NO: 80, and a CDRL3 having the sequence as set forth in SEQ ID NO: 81.

16. The multi-domain binding molecule of claim 9, wherein a binding domain of the immune cell engaging molecule binds CD28.

17. The multi-domain binding molecule of claim 16, wherein the CD28 binding domain is derived from the TGN1412 antibody.

18. The multi-domain binding molecule of claim 5, wherein the single-domain antibody is linked to a first Fc region of the multi-domain binding molecule and a binding domain that binds CD3 is linked to the second Fc region of the multi-domain binding molecule.

19. A method of treating a subject in need thereof having an ROR1-related cancer, the method comprising administering a therapeutically effective amount of the single-domain antibody of claim 1 to the subject thereby treating the subject in need thereof having the ROR1-related cancer.

20. The method of claim 19, wherein the ROR1-related cancer comprises chronic lymphocytic leukemia (CLL), hairy cell leukemia (HCL), mantle cell lymphoma (MCL), marginal zone lymphoma (MZL), diffuse large B cell lymphoma (DLBCL), follicular lymphoma (FL), multiple myeloma (MM), acute lymphocytic leukemia (ALL), acute myeloid leukemia (AML), chronic myeloid leukemia (CML), breast cancer, ovarian cancer, pancreatic cancer, lung cancer, or neuroblastoma.

\* \* \* \* \*